United States Patent
Yoshida et al.

(10) Patent No.: US 11,566,017 B2
(45) Date of Patent: *Jan. 31, 2023

(54) DIHYDROQUINAZOLINONE COMPOUND OR PHARMACOLOGICALLY ACCEPTABLE SALT, AND CELL GROWTH INHIBITOR

(71) Applicants: RIKEN, Wako (JP); JAPANESE FOUNDATION FOR CANCER RESEARCH, Koto-ku (JP); KABUSHIKI KAISHA YAKULT HONSHA, Minato-ku (JP)

(72) Inventors: Minoru Yoshida, Wako (JP); Hiroyuki Seimiya, Koto-ku (JP); Yoko Yashiroda, Wako (JP); Kenichi Washizuka, Wako (JP); Fumiyuki Shirai, Wako (JP); Nobuko Yoshimoto, Wako (JP); Junichi Kazami, Wako (JP)

(73) Assignees: RIKEN, Wako (JP); JAPANESE FOUNDATION FOR CANCER RESEARCH, Koto-ku (JP); KABUSHIKI KAISHA YAKULT HONSHA, Minato-ku (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/958,066

(22) PCT Filed: Dec. 26, 2018

(86) PCT No.: PCT/JP2018/047944
§ 371 (c)(1),
(2) Date: Jun. 25, 2020

(87) PCT Pub. No.: WO2019/131798
PCT Pub. Date: Jul. 4, 2019

(65) Prior Publication Data
US 2021/0061789 A1    Mar. 4, 2021

(30) Foreign Application Priority Data
Dec. 27, 2017 (JP) .............................. JP2017-252179

(51) Int. Cl.
*C07D 403/04* (2006.01)
*C07D 498/06* (2006.01)

(52) U.S. Cl.
CPC .......... *C07D 403/04* (2013.01); *C07D 498/06* (2013.01)

(58) Field of Classification Search
CPC ..................... C07D 403/04; C07D 498/06
See application file for complete search history.

(56) References Cited

U.S. PATENT DOCUMENTS

| | | |
|---|---|---|
| 2004/0077667 A1 | 4/2004 | Matsuoka et al. |
| 2005/0124607 A1 | 6/2005 | Chin et al. |
| 2015/0239850 A1 | 8/2015 | Dorsch et al. |
| 2021/0060016 A1* | 3/2021 | Seimiya ................. A61P 35/00 |

FOREIGN PATENT DOCUMENTS

| | | |
|---|---|---|
| JP | 2004-515544 A | 5/2004 |
| JP | 2009-513504 A | 4/2009 |
| JP | 2015-535831 A | 12/2015 |
| WO | WO 2010/056758 A1 | 5/2010 |
| WO | WO 2012/076898 A1 | 6/2012 |

(Continued)

OTHER PUBLICATIONS

CAS Registry No. 1006996-95-7, which entered STN on Mar. 7, 2008 (Year: 2008).*
Zhang et al. European Journal of Medicinal Chemistry 2018, 152, 235-252 (Year: 2018).*
CAS Registry No. 1011419-04-7, which entered STN on Apr. 1, 2008 (Year: 2008).*
CAS Registry No. 1186616-13-6, which entered STN on Sep. 30, 2009 (Year: 2009).*
CAS Registry No. 1311504-77-4, which entered STN on Jul. 6, 2011 (Year: 2011).*

(Continued)

*Primary Examiner* — Matthew P Coughlin
(74) *Attorney, Agent, or Firm* — Oblon, McClelland, Maier & Neustadt, L.L.P.

(57) ABSTRACT

Provided is a cell proliferation inhibitor comprising a compound of the formula (1) or a pharmacologically acceptable salt thereof:

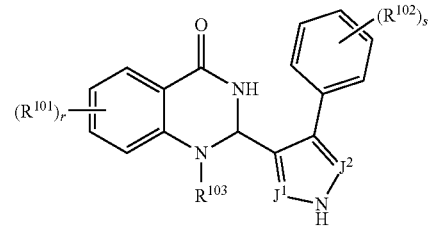

wherein $J^1$ and $J^2$ each represent CH or N, with the proviso that $J^1$ and $J^2$ are not simultaneously CH; r represents 0 to 4; each $R^{101}$ is the same or different when r is 2 or more, and $R^{101}$ represents a $C_{1-6}$ alkyl group optionally substituted with a halogen atom or the like; s represents 0 to 5; each $R^{102}$ is the same or different when s is 2 or more, and $R^{102}$ represents a halogen atom or the like; $R^{103}$ represents a hydrogen atom, a $C_{1-6}$ alkyl group, a $C_{3-6}$ cycloalkyl group, or a $C_{3-6}$ cycloalkyl $C_{1-6}$ alkyl group; and $R^{101}$ and $R^{103}$ are optionally linked together to form a five- to seven-membered ring hetero ring when $R^{101}$ is present at the 8-position.

24 Claims, 1 Drawing Sheet

(56) References Cited

FOREIGN PATENT DOCUMENTS

| WO | WO 2013/117288 A1 | 8/2013 | |
| --- | --- | --- | --- |
| WO | WO 2013/182580 A1 | 12/2013 | |
| WO | WO-2019131794 A1 * | 7/2019 | ............ A61K 45/06 |

OTHER PUBLICATIONS

International Search Report dated Mar. 26, 2019 in PCT/Jp2018/047944 filed on Dec. 26, 2018, 3 pages.
Huang et al., "Tankyrase inhibition stabilizes axin and antagonizes Wnt signalling", NATURE, 2009, vol. 461, pp. 614-620.
Shultz et al., "Identification of NVP-TNKS656: The Use of Structure-Efficiency Relationships To Generate a Highly Potent, Selective, and Orally Active Tankyrase Inhibitor", Journal of Medicinal Chemistry, 2013, vol. 56, pp. 6495-6511.
Voronkov et al., "Structural Basis and SAR for G007-LK, a Lead Stage 1,2,4-Triazole Based Specific Tankyrase 1/2 Inhibitor", Journal of Medicinal Chemistry, 2013, vol. 56, pp. 3012-3023.
Johannes et al., "Pyrimidinone Nicotinamide Mimetics as Selective Tankyrase and Wnt Pathway Inhibitors Suitable for in Vivo Pharmacology", ACS Medicinal Chemistry Letters, 2015, vol. 6, pp. 254-259.
Haikarainen et al., "para-Substituted 2-Phenyl-3,4-dihydroquinazolin-4-ones As Potent and Selective Tankyrase Inhibitors", ChemMedChem, 2013, vol. 8, pp. 1978-1985.
Shultz et al., "[1,2,4]Triazol-3-ylsulfanylmethyl)-3-phenyl-[1,2,4]oxadiazoles: Antagonists of the Wnt Pathway That Inhibit Tankyrases 1 and 2 via Novel Adenosine Pocket Binding", Journal of Medicinal Chemistry, 2012, vol. 55, pp. 1127-1136.

* cited by examiner

DIHYDROQUINAZOLINONE COMPOUND OR PHARMACOLOGICALLY ACCEPTABLE SALT, AND CELL GROWTH INHIBITOR

TECHNICAL FIELD

The present invention relates to a novel compound or a pharmacologically acceptable salt thereof and a cell proliferation inhibitor, specifically to a novel dihydroquinazolinone-based compound which has tankyrase inhibitory activity and/or microtubule inhibitory activity, a pharmacologically acceptable salt thereof, and a tankyrase inhibitor, a microtubule inhibitor and a pharmaceutical composition comprising the dihydroquinazolinone-based compound or pharmacologically acceptable salt thereof.

BACKGROUND ART

Poly(ADP-ribosyl)ation is a biochemical reaction which is a chain addition of ADP-ribose to glutamic acid or aspartic acid residues of a protein, with nicotinamide adenine dinucleotide as a substrate. A produced poly(ADP-ribose) chain is composed of about 200 ADP-riboses at longest. A poly(ADP-ribose) polymerase (PARP) family is known as an enzyme which catalyzes the poly(ADP-ribosyl)ation reaction.

Of the PARP family, PARP-5a and PARP-5b are called tankyrase-1 and tankyrase-2, respectively. Normally, in many cases, both enzymes are simply called tankyrase collectively. The tankyrase is composed of an ankyrin region which recognizes a protein which is to be poly(ADP-ribosyl)ated; a sterile alpha motif (SAM) region which is involved in self-multimerization; and a PARP catalytic domain which controls the poly(ADP-ribosyl)ation reaction.

The tankyrase binds to various proteins through the ankyrin region in the molecule to poly(ADP-ribosyl)ates these proteins. Examples of tankyrase-bound proteins include TRF1, NuMA, Plk1, Miki, Axin, TNKS1BP1, IRAP, McI-1 and 3BP2. The tankyrase poly(ADP-ribosyl)ates these proteins to regulate the physiological functions of the proteins. Hence, inhibition of tankyrase is considered to be effective for the control of cell proliferation, cell differentiation, tissue formation and the like which are the physiological functions of the proteins.

Examples of known tankyrase inhibitory compounds having tankyrase inhibitory activity include the compound XAV939 described in Non Patent Literature 1 (Huang SM. et al., Nature, Vol. 461, pp. 614-620, 2009), the compounds described in Patent Literature 1 (WO 2013/117288) and Patent Literature 2 (WO 2013/182580), NVP-TNKS656 described in Non Patent Literature 2 (Michael D. Shultz et al., Journal of Medicinal Chemistry, 56, pp. 6495-6511, 2013), and G007-LK described in Non Patent Literature 3 (Andrew Voronkov. et al., Journal of Medicinal Chemistry, 56, pp. 3012-3023, 2013) and Patent Literature 3 (WO 2012/076898).

A microtubule is a protein forming a cytoskeleton, and is involved in formation of a spindle in the phase of cell division period, formation and maintenance of cellular morphology, arrangement of intracellular organelles and transport of substances to the organs, axonal transport in nerve cells, and the like. The microtubule is composed of tubulin dimers each composed of an α-subunit and a β-subunit. A process in which the dimers aggregate to form a microtubule is referred to as polymerization, and a process in which a microtubule reverts to a tubulin is referred to as depolymerization.

As microtubule inhibitors which inhibit microtubules, microtubule depolymerization inhibitors for promoting the polymerization to stabilize and excessively form microtubules, and microtubule polymerization inhibitors for inhibiting the polymerization are known, and these microtubule inhibitors each suppress cell proliferation by disrupting the state of dynamic equilibrium of microtubule polymerization to arrest the cell cycle in the M phase. As such microtubule inhibitors, paclitaxel, vinblastine, vincristine, vindesine, vinorelbine, docetaxel, cabazitaxel, eribulin and the like are known. These microtubule inhibitors are commercially available as agents having an antitumor effect on leukemia, malignant lymphoma and malignant tumors.

Such tankyrase inhibitors and microtubule inhibitors are considered to have an effect against fibrosarcoma, ovary cancer, glioblastoma, pancreatic cancer, breast cancer, astrocytoma, lung cancer, gastric cancer, hepatocyte cancer, multiple myeloma, colorectal cancer, bladder cancer, leukemia, infections with a Herpes simplex virus, an Epstein-Barr virus and the like, fibroses such as pulmonary fibrosis, cherubism, multiple sclerosis, amyotrophic lateral sclerosis, skin and cartilage injuries, metabolic diseases and the like, and a suppressive effect on cancer metastasis. Development of a new pharmaceutical product for preventing and/or treating the above-mentioned diseases is desired.

CITATION LIST

Patent Literature

Patent Literature 1: WO 2013/117288
Patent Literature 2: WO 2013/182580
Patent Literature 3: WO 2012/076898

Non Patent Literature

Non Patent Literature 1: Huang SM. et al., Nature, Vol. 461, pp. 614-620, 2009
Non Patent Literature 2: Michael D. Shultz et al., Journal of Medicinal Chemistry, 56, pp. 6495-6511, 2013
Non Patent Literature 3: Andrew Voronkov. et al., Journal of Medicinal Chemistry, 56, pp. 3012-3023, 2013

SUMMARY OF INVENTION

Technical Problem

The present invention has been made in view of the problems of the conventional techniques, and an object of the present invention is to provide a novel compound which has excellent tankyrase inhibitory activity and/or microtubule inhibitory activity and which is useful for treatment and/or prevention of, for example, proliferative diseases such as cancer, and also useful for treatment of Herpes virus infection, multiple sclerosis, sugar metabolism disease, skin and cartilage damages, pulmonary fibrosis and the like; a pharmacologically acceptable salt thereof; and a cell proliferation inhibitor, a tankyrase inhibitor, a microtubule inhibitor and a pharmaceutical composition which have excellent tankyrase inhibitory activity and/or microtubule inhibitory activity. Another object of the present invention is to provide a method for producing the novel compound or a pharmacologically acceptable salt thereof, and an intermediate compound useful for the production thereof.

Solution to Problem

The present inventors have extensively conducted studies for solving the above-described problems, and resultantly found that a dihydroquinazolinone-based compound having a specific structure, and a pharmacologically acceptable salt thereof have excellent tankyrase inhibitory activity and/or microtubule inhibitory activity. Accordingly, the present invention has been completed.

That is, the present invention includes the following.
A cell proliferation inhibitor, comprising a compound of the formula (1) or a pharmacologically acceptable salt thereof as an active ingredient:

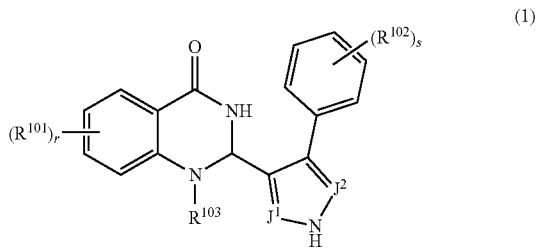

wherein $J^1$ and $J^2$ each represent CH or N, with the proviso that $J^1$ and $J^2$ are not simultaneously CH;

r represents 0 to 4;

each $R^{101}$ is the same or different when r is 2 or more, and represents a halogen atom, a $C_{1-6}$ alkyl group optionally substituted with a halogen atom, $OR^{111}$, or a group represented by the formula: $-N(R^{112a})-R^{112b}$, where $R^{111}$, $R^{112a}$ and $R^{112b}$ are each independently a hydrogen atom or a $C_{1-6}$ alkyl group;

s represents 0 to 5;

each $R^{102}$ is the same or different when s is 2 or more, and represents a halogen atom, a $C_{1-6}$ alkyl group, $OR^{113}$, a group represented by the formula: $-N(R^{114a})-R^{114b}$, a group represented by the formula: $-NH-C(=O)-R^{115}$, a group represented by the formula: $-C(=O)-R^{116}$, an optionally substituted aryl group, an optionally substituted heteroaryl group, a nitro group, or a cyano group, where $R^{113}$ is a hydrogen atom, an optionally substituted alkyl group, an optionally substituted aryl group, an optionally substituted arylalkyl group, or an optionally substituted heteroaryl group, $R^{114a}$ and $R^{114b}$ are each independently a hydrogen atom or a $C_{1-6}$ alkyl group, $R^{115}$ is an optionally substituted alkyl group, an optionally substituted aryl group, an optionally substituted heteroaryl group, or a group represented by the formula: $-NH-R^{121}$, $R^{116}$ is an optionally substituted alkyl group, an optionally substituted aryl group, an optionally substituted heteroaryl group, $OR^{122}$, or a group represented by the formula: $-N(R^{123a})-R^{123b}$, $R^{121}$ is an optionally substituted alkyl group, an optionally substituted aryl group, or an optionally substituted heteroaryl group, $R^{122}$ is a hydrogen atom, an optionally substituted alkyl group, an optionally substituted aryl group, or an optionally substituted heteroaryl group, and $R^{123a}$ and $R^{123b}$ are each independently a hydrogen atom, an optionally substituted alkyl group, an optionally substituted aryl group, or an optionally substituted heteroaryl group, or $R^{123a}$ and $R^{123b}$ are linked together to form a cyclic amine;

$R^{103}$ represents a hydrogen atom, a $C_{1-6}$ alkyl group, a $C_{3-6}$ cycloalkyl group, or a $C_{3-6}$ cycloalkyl $C_{1-6}$ alkyl group; and $R^{101}$ and $R^{103}$ are optionally linked together to form a five- to seven-membered ring hetero ring when $R^{101}$ is present at the 8-position.

[2] The cell proliferation inhibitor according to [1], wherein in the formula (1), r is 0; or r is 1, $R^{101}$ is present at the 7-position or the 8-position and $R^{101}$ represents a $C_{1-3}$ alkyl group optionally substituted with a halogen atom, or a hydroxy group; or r is 1, $R^{101}$ is present at the 8-position and $R^{101}$ and $R^{103}$ are linked together to form a five- or six-membered ring hetero ring.

[3] The cell proliferation inhibitor according to [1] or [2], wherein in the formula (1), $R^{103}$ represents a hydrogen atom, a $C_{1-3}$ alkyl group or a $C_{3-6}$ cycloalkyl $C_{1-3}$ alky group; or r is 1, $R^{101}$ is present at the 8-position and $R^{101}$ and $R^{103}$ are linked together to form a five- or six-membered ring hetero ring.

[4] The cell proliferation inhibitor according to any one of [1] to [3], wherein in the formula (1), s is 0; or s is 1 and $R^{102}$ represents a halogen atom, $OR^{113}$ in which $R^{113}$ is an optionally substituted $C_{1-3}$ alkyl group, or an optionally substituted aryl group.

[5] The cell proliferation inhibitor according to any one of [1] to [4], wherein in the formula (1), $J^1$ and $J^2$ each represent N.

[6] The cell proliferation inhibitor according to any one of [1] to [5], wherein the cell proliferation inhibitor is a tankyrase inhibitor.

[7] The cell proliferation inhibitor according to any one of [1] to [6], wherein the cell proliferation inhibitor is a microtubule inhibitor.

[8] The cell proliferation inhibitor according to any one of [1] to [7], wherein the cell proliferation inhibitor is a pharmaceutical composition.

[9] The cell proliferation inhibitor according to [8], wherein the cell proliferation inhibitor is a prophylactic and/or therapeutic agent for at least one selected from the group consisting of malignant tumor, Herpes simplex virus infection, Epstein-Barr virus infection, pulmonary fibrosis, multiple sclerosis and amyotrophic lateral sclerosis.

[10] A compound of the formula (1a) or a pharmacologically acceptable salt thereof:

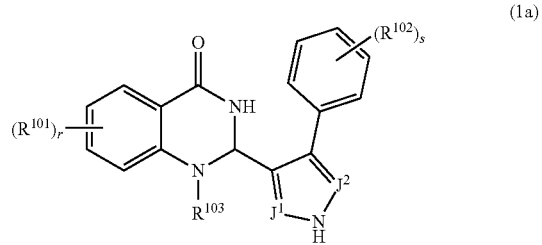

wherein $J^1$ and $J^2$ each represent CH or N, with the proviso that $J^1$ and $J^2$ are not simultaneously CH;

r represents 0 to 4;

each $R^{101}$ is the same or different when r is 2 or more, and represents a halogen atom, a $C_{1-6}$ alkyl group optionally substituted with a halogen atom, $OR^{111}$, or a group represented by the formula: $-N(R^{112a})-R^{112b}$, where $R^{111}$, $R^{112a}$ and $R^{112b}$ are each independently a hydrogen atom or a $C_{1-6}$ alkyl group;

s represents 0 to 5;

each $R^{102}$ is the same or different when s is 2 or more, and represents a halogen atom, a $C_{1-6}$ alkyl group, $OR^{113}$, a group represented by the formula: $-N(R^{114a})-R^{114b}$, a group represented by the formula: —NH—C(=O)—$R^{115}$, a group represented by the formula: —C(=O)—$R^{116}$, an optionally substituted aryl group, an optionally substituted heteroaryl group, a nitro group, or a cyano group, where $R^{113}$ is a hydrogen atom, an optionally substituted alkyl group, an optionally substituted aryl group, an optionally substituted arylalkyl group, or an optionally substituted heteroaryl group, $R^{114a}$ and $R^{114b}$ are each independently a hydrogen atom or a $C_{1-6}$ alkyl group, $R^{115}$ is an optionally substituted alkyl group, an optionally substituted aryl group, an optionally substituted heteroaryl group, or a group represented by the formula: —NH—$R^{121}$, $R^{116}$ is an optionally substituted alkyl group, an optionally substituted aryl group, an optionally substituted heteroaryl group, $OR^{122}$, or a group represented by the formula: —N($R^{123a}$)—$R^{123b}$, $R^{121}$ is an optionally substituted alkyl group, an optionally substituted aryl group, or an optionally substituted heteroaryl group, $R^{122}$ is a hydrogen atom, an optionally substituted alkyl group, an optionally substituted aryl group, or an optionally substituted heteroaryl group, and $R^{123a}$ and $R^{123b}$ are each independently a hydrogen atom, an optionally substituted alkyl group, an optionally substituted aryl group, or an optionally substituted heteroaryl group, or $R^{123a}$ and $R^{123b}$ are linked together to form a cyclic amine;

$R^{103}$ represents a hydrogen atom, a $C_{1-6}$ alkyl group, a $C_{3-6}$ cycloalkyl group, or a $C_{3-6}$ cycloalkyl $C_{1-6}$ alkyl group; and $R^{101}$ and $R^{103}$ are optionally linked together to form a five- to seven-membered ring hetero ring when $R^{101}$ is present at the 8-position, with the exception of cases where $J^1$ represents CH, $J^2$ represents N, r is 0, $R^{103}$ is a hydrogen atom or a methyl group, $R^{102}$ is present at the p-position, and $R^{102}$ is a methoxy group.

[11] The compound according to [10] or a pharmacologically acceptable salt thereof, wherein in the formula (1a), r is 0; or r is 1, $R^{101}$ is present at the 7-position or the 8-position and $R^{101}$ represents a $C_{1-3}$ alkyl group optionally substituted with a halogen atom, or a hydroxy group; or r is 1, $R^{101}$ is present at the 8-position and $R^{101}$ and $R^{103}$ are linked together to form a five- or six-membered ring hetero ring.

[12] The compound according to [10] or [11] or a pharmacologically acceptable salt thereof, wherein in the formula (1a), $R^{103}$ represents a hydrogen atom, a $C_{1-3}$ alkyl group or a $C_{3-6}$ cycloalkyl $C_{1-3}$ alky group; or r is 1, $R^{101}$ is present at the 8-position and $R^{101}$ and $R^{103}$ are linked together to form a five- or six-membered ring hetero ring.

[13] The compound according to any one of [10] to [12] or a pharmacologically acceptable salt thereof, wherein in the formula (1a), s is 0; or s is 1 and $R^{102}$ represents a halogen atom, $OR^{113}$ in which $R^{113}$ is an optionally substituted $C_{1-3}$ alkyl group, or an optionally substituted aryl group.

[14] A tankyrase inhibitor comprising the compound according to any one of [10] to [13] or a pharmacologically acceptable salt thereof as an active ingredient.

[15] A microtubule inhibitor comprising the compound according to any one of [10] to [13] or a pharmacologically acceptable salt thereof as an active ingredient.

[16] A pharmaceutical composition comprising the compound according to any one of [10] to [13] or a pharmacologically acceptable salt thereof as an active ingredient.

[17] A prophylactic and/or therapeutic agent for a disease attributable to tankyrase and/or microtubules, comprising at least one compound selected from the group consisting of a compound of the formula (1), a compound of the formula (1a) and a pharmacologically acceptable salt thereof as an active ingredient.

[18] A method for inhibiting tankyrase, comprising administering to a patient at least one compound selected from the group consisting of a compound of the formula (1), a compound of the formula (1a) and a pharmacologically acceptable salt thereof, or the cell proliferation inhibitor according to [1].

[19] A method for inhibiting microtubules, comprising administering to a patient at least one compound selected from the group consisting of a compound of the formula (1), a compound of the formula (1a) and a pharmacologically acceptable salt thereof, or the cell proliferation inhibitor according to [1].

[20] A method for treating a disease attributable to tankyrase and/or microtubules, comprising administering to a patient at least one compound selected from the group consisting of a compound of the formula (1), a compound of the formula (1a) and a pharmacologically acceptable salt thereof, or the cell proliferation inhibitor according to [1].

[21] A compound of the formula (1) or a pharmacologically acceptable salt thereof, for use in inhibiting tankyrase and/or inhibiting microtubules.

[22] A compound of the formula (1) or a pharmacologically acceptable salt thereof, for use in treating a disease attributable to tankyrase and/or microtubules.

Advantageous Effects of Invention

According to the present invention, it is possible to provide a novel compound which has excellent tankyrase inhibitory activity and/or microtubule inhibitory activity and which is effective against diseases related to tankyrase and/or microtubules; a pharmacologically acceptable salt thereof; and a cell proliferation inhibitor, a tankyrase inhibitor, a microtubule inhibitor and a pharmaceutical composition which have excellent tankyrase inhibitory activity and/or microtubule inhibitory activity. It is also possible to provide a method for producing the novel compound or a pharmacologically acceptable salt thereof, and an intermediate compound useful for the production thereof.

Examples of the diseases related to tankyrase and/or microtubules include, but are not limited to, various solid tumors and blood tumors, for example, malignant tumors such as fibrosarcoma, ovary cancer, glioblastoma, pancreatic cancer, breast cancer, astrocytoma, lung cancer, gastric cancer, liver cancer, colorectal cancer, bladder cancer and leukemia; infections such as Herpes simplex virus infection and Epstein-Barr virus infection; fibroses such as pulmonary fibrosis; neurodegenerative diseases such as multiple sclerosis and amyotrophic lateral sclerosis; and various types of inflammatory diseases such as skin and cartilage damages.

DESCRIPTION OF EMBODIMENTS

Figure 1A:
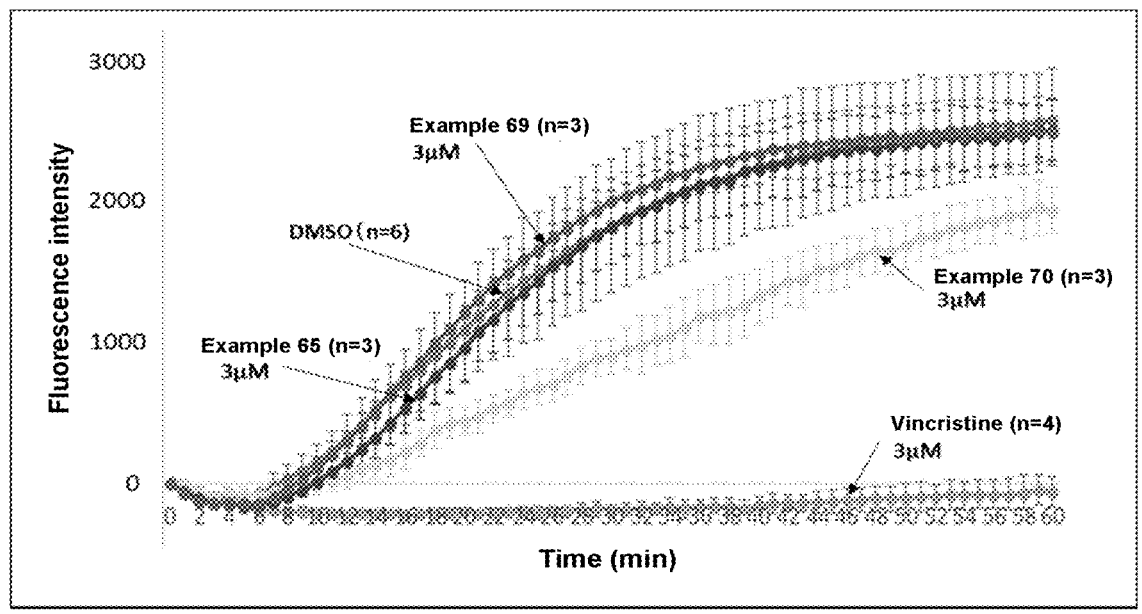
FIG. 1A shows the results of conducting a microtubule polymerization inhibition test of compounds prepared in Examples 65, 69 and 70 (compound concentration: 3 µM).

The present invention provides a cell proliferation inhibitor comprising a compound of the formula (1) or a pharmacologically acceptable salt thereof as an active ingredient:

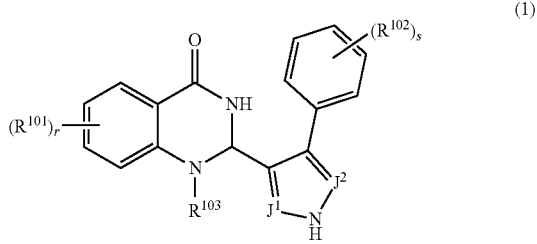

(1)

wherein $J^1$ and $J^1$ each represent CH or N, with the proviso that $J^1$ and $J^2$ are not simultaneously CH;

r represents 0 to 4;

each $R^{101}$ is the same or different when r is 2 or more, and represents a halogen atom, a $C_{1-6}$ alkyl group optionally substituted with a halogen atom, $OR^{111}$, or a group represented by the formula: $-N(R^{112a})-R^{112b}$, where $R^{111}$, $R^{111a}$ and $R^{112b}$ are each independently a hydrogen atom or a $C_{1-6}$ alkyl group;

s represents 0 to 5;

each $R^{102}$ is the same or different when s is 2 or more, and represents a halogen atom, a $C_{1-6}$ alkyl group, $OR^{113}$, a group represented by the formula: $-N(R^{114a})-R^{114b}$, a group represented by the formula: $-NH-C(=O)-R^{115}$, a group represented by the formula: $-C(=O)-R^{116}$, an optionally substituted aryl group, an optionally substituted heteroaryl group, a nitro group, or a cyano group, where $R^{113}$ is a hydrogen atom, an optionally substituted alkyl group, an optionally substituted aryl group, an optionally substituted arylalkyl group, or an optionally substituted heteroaryl group, $R^{114a}$ and $R^{114b}$ are each independently a hydrogen atom or a $C_{1-6}$ alkyl group, $R^{115}$ is an optionally substituted alkyl group, an optionally substituted aryl group, an optionally substituted heteroaryl group, or a group represented by the formula: $-NH-R^{121}$, $R^{116}$ is an optionally substituted alkyl group, an optionally substituted aryl group, an optionally substituted heteroaryl group, $OR^{122}$, or a group represented by the formula: $-N(R^{123a})-R^{123b}$, $R^{121}$ is an optionally substituted alkyl group, an optionally substituted aryl group, or an optionally substituted heteroaryl group, $R^{122}$ is a hydrogen atom, an optionally substituted alkyl group, an optionally substituted aryl group, or an optionally substituted heteroaryl group, and $R^{123a}$ and $R^{123b}$ are each independently a hydrogen atom, an optionally substituted alkyl group, an optionally substituted aryl group, or an optionally substituted heteroaryl group, or $R^{123a}$ and $R^{123b}$ are linked together to form a cyclic amine;

$R^{103}$ represents a hydrogen atom, a $C_{1-6}$ alkyl group, a $C_{3-6}$ cycloalkyl group, or a $C_{3-6}$ cycloalkyl $C_{1-6}$ alkyl group; and $R^{101}$ and $R^{103}$ are optionally linked together to form a five- to seven-membered ring hetero ring when $R^{101}$ is present at the 8-position. The present invention also provides a compound of the formula (1a) or a pharmacologically acceptable salt thereof:

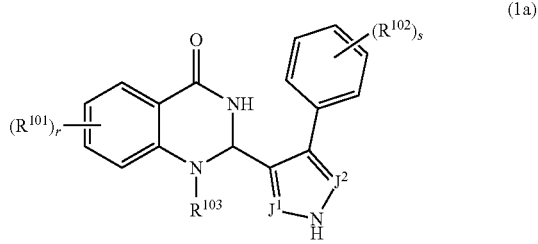

(1a)

wherein $J^1$, $J^2$, r, $R^{101}$, s, $R^{102}$ and $R^{103}$ are each independently the same as $J^1$, $J^2$, r, $R^{101}$, s, $R^{102}$ and $R^{103}$ in the formula (1), respectively, with the exception of cases where $J^1$ represents CH, $J^2$ represents N, r is 0, $R^{103}$ is a hydrogen atom or a methyl group, $R^{102}$ is present at the p-position, and $R^{102}$ is a methoxy group.

In the present invention, the "dihydroquinazolinone-based compound" refers to a compound in which a hydrogen atom or a substituent is partially added at the 1-position and the 2-position of quinazolinone; or a salt thereof. In the present invention, unless otherwise specified, the number associated with "position" in the formulas (1) and (1a) indicates a position number at which $R^{101}$ is substituted in the dihydroquinazolinone-based compound, and a position number of quinazolinone is directly applied to the position number. Further, in the present invention, unless otherwise specified, the alphabet (o, m or p) associated with "position" in the formulas (1) and (1a) indicates a position number of a benzene substituent with which $R^{10}$ is substituted.

In the formulas (1) and (1a), the "hydrogen atoms" include deuterium atoms (D). In the formulas (1) and (1a), the "halogen atoms" include fluorine atoms, chlorine atoms, bromine atoms and iodine atoms.

In the formulas (1) and (1a), the "alkyl group" refers to a linear or branched saturated hydrocarbon group having 1 to 8 carbon atoms. Examples of the linear or branched saturated hydrocarbon group generally include, but are not particularly limited to, groups such as methyl, ethyl, n-propyl, isopropyl, n-butyl, sec-butyl, isobutyl, tert-butyl, n-pentyl, isopentyl, neopentyl and n-hexyl groups. Of these, "$C_{1-6}$ alkyl groups" having 1 to 6 carbon atoms are preferable, and "$C_{1-3}$ alkyl groups" having 1 to 3 carbon atoms are more preferable, as the "alkyl group" according to the present invention.

In the formulas (1) and (1a), the "aryl group" refers to a six-membered ring monocyclic aromatic hydrocarbon group consisting of only carbon atoms, or a fused-ring aromatic hydrocarbon group in which two or more such six-membered ring monocyclic aromatic hydrocarbon groups are fused. Examples of the aryl group generally include, but are not particularly limited to, groups such as phenyl and naphthyl groups. Of these, monocyclic aromatic hydrocarbon groups (phenyl groups) are preferable as the "aryl group" according to the present invention.

In the formulas (1) and (1a), the "heteroaryl group" refers to a group derived from a five- or six-membered ring monocyclic aromatic heterocycle having 1 to 4 hetero atoms selected from the group consisting of a nitrogen atom, an oxygen atom and a sulfur atom; a group derived from a fused-ring aromatic heterocycle in which a five- or six-membered ring monocyclic aromatic heterocycle having 1 to 4 hetero atoms is fused with a six-membered ring monocyclic aromatic ring consisting of only carbon atoms; or a group derived from a fused-ring aromatic heterocycle in which a five- or six-membered ring monocyclic aromatic heterocycle having 1 to 4 hetero atoms is fused with a five- or six-membered ring monocyclic aromatic heterocycle having 1 to 4 hetero atoms. Examples of the heteroaryl group generally include, but are not particularly limited to, groups such as pyrrolyl, pyrazolyl, furyl, thienyl, oxazolyl, imidazolyl, isoxazolyl, thiazolyl, isothiazolyl, 1,2,3-oxadiazolyl, 1,2,4-oxadiazolyl, 1,2,3-thiadiazolyl, 1,2,4-thiadiazolyl, tetrazolyl, 1,2,4-triazolyl, 1,2,3-triazolyl, pyridyl, pyridazinyl, pyrazyl, pyrimidyl, benzothienyl, benzofuryl, indolyl, isoindolyl, benzimidazolyl, benzopyrazolyl, benzothiazolyl, benzoxazolyl, benzotriazolyl, quinolyl, isoquinolyl, quinoxalinyl, quinazolinyl, phthalazinyl, imidazo[5,1-b]thiazolyl and 1H-pyrrolo[2,3-b]pyridinyl groups, each of which has a binding site at any possible position. Of these, quinolyl, isoquinolyl and 1H-pyrrolo[2,3-b]pyridinyl, each of which has a binding site at any possible position, are preferable as the "heteroaryl group" according to the present invention.

In the general formulas (1) and (1a), the "cycloalkyl group" refers to a saturated hydrocarbon group (cyclic hydrocarbon group) having 3 to 8 carbon atoms, and the cyclic hydrocarbon group may be a monocyclic ring, or may form a fused ring, a crosslinked ring or a spiro ring. Examples of the cyclic saturated hydrocarbon group generally include, but are not particularly limited to, groups such as cyclopropyl, cyclobutyl, cyclopentyl, cyclohexyl, cycloheptyl, cyclooctyl, bicyclo[3.1.0]hexyl, bicyclo[3.2.0]heptyl, bicyclo[4.1.0]heptyl, bicyclo[4.2.0]octyl, bicyclo[3.3.0]octyl, bicyclo[1.1.1]pentyl, bicyclo[2.1.1]hexyl, bicyclo[3.1.1]heptyl, bicyclo[2.2.1]heptyl, bicyclo[3.2.1]octyl, bicyclo[2.2.2]octyl, spiro[2.3]hexyl, spiro[2.4]heptyl, spiro[2.5]octyl, spiro[3.3]heptyl and spiro[3.4]octyl groups, each of which has a binding site at any possible position. Of these, monocyclic cycloalkyl groups are preferable, "$C_{3-8}$ cycloalkyl groups" having 3 to 8 carbon atoms are more preferable, and $C_{3-6}$ cycloalkyl groups" having 3 to 6 carbon atoms are still more preferable, as the "cycloalkyl group" according to the present invention.

In the formulas (1) and (1a), the "hetero ring" refers to an unsaturated heterocycle other than an aromatic ring, which has 1 to 4 hetero atoms selected from the group consisting of a nitrogen atom, an oxygen atom and a sulfur atom, and the hetero ring is preferably five- to seven-membered ring ring, more preferably five- or six-membered ring ring. The heterocycle may be a monocyclic ring, or may form a crosslinked ring or a spiro ring. Examples of the "five- to seven-membered ring heterocycle" include, but are not particularly limited to, rings such as 2,3-dihydro-1H-pyrrole, 2,3-dihydrooxazole, 2,3-dihydro-1H-imidazole, 1,2,3,4-tetrahydropyridine, 2,3,4,5-tetrahydro-1H-azepine, 3,4-dihydro-2H-1,4-oxazine, 1,2,3,4-tetrahydropyrazine, 3,4-dihydro-2H-1,4-thiazine and 4,5,6,7-tetrahydro-1,4-oxazepine rings, each of which has a binding site at any possible position. Of these, 2,3-dihydro-1H-pyrrole, 1,2,3,4-tetrahydropyrazine and 3,4-dihydro-2H-1,4-oxazine, each of which has a binding site at any possible position, are preferable as the "five- to seven-membered ring hetero ring" according to the present invention.

In the present invention, the "heterocycloalkyl group" refers to a three- to seven-membered ring saturated heterocycle or unsaturated heterocycle other than an aromatic ring, which has 1 to 4 hetero atoms selected from the group consisting of a nitrogen atom, an oxygen atom and a sulfur atom, and the heterocycle may be a monocyclic ring, or may form a crosslinked ring or a spiro ring. Examples of the heterocycloalkyl group include, but are not particularly limited to, groups such as oxetanyl, tetrahydrofuryl, dihydrofuryl, dihydropyranyl, tetrahydropyranyl, 1,3-dioxanyl, 1,4-dioxanyl, aziridinyl, azetidinyl, pyrrolidinyl, piperidinyl, piperazinyl, 1,1-dioxide thiomorphorinyl, dioxopiperazinyl, diazepanyl, morphorinyl, 1,3-dioxolanyl, imidazolidinyl, imidazolinyl, pyrrolinyl, oxathiolanyl, dithiolanyl, 1,3-dithianyl, 1,4-dithianyl, oxathianyl, thiomorphorinyl, 3,6-diazabicylo[3.1.1]heptyl, 8-oxa-3-azabicyclo[3.2.1]octyl, 3,8-diazabicyclo[3.2.1]octyl, 3,9-diazabicyclo[3.3.1]nonyl and 2-oxa-7-azaspiro[3.5]nonyl groups, each of which has a binding site at any possible position. Of these, piperazinyl, pyrrolidinyl and morpholinyl, each of which has a binding site at any possible position, are preferable as the "heterocycloalkyl group" according to the present invention.

In the formulas (1) and (1a), the "arylalkyl group", the "cycloalkylalkyl group" or the "heterocycloalkylalkyl group" refers to a group (a group represented by -Ak$^1$-Ar$^1$) in which an aryl group, a cycloalkyl group or a heterocycloalkyl group (represented by the formula: —Ar$^1$) as defined herein is bonded at a binding site at any possible position to a binding site at any possible position in an alkyl group (represented by the formula: -Ak$^1$) as defined herein. Of these, "aryl $C_{1-6}$ alkyl groups (aryl $C_{1-6}$ alkylene groups)" in which the alkyl group has 1 to 6 carbon atoms are preferable, and "aryl $C_{1-3}$ alkyl groups (aryl $C_{1-3}$ alkylene groups)" in which the alkyl group has 1 to 3 carbon atoms are preferable, as the "arylalkyl group" according to the present invention. The "cycloalkylalkyl group" according to the present invention is preferably a "cycloalkyl $C_{1-6}$ alkyl group (cycloalkyl $C_{1-6}$ alkylene group)" in which the alkyl group has 1 to 6 carbon atoms; more preferably a "cycloalkyl $C_{1-3}$ alkyl group (cycloalkyl $C_{1-3}$ alkylene group)" in which the alkyl group has 1 to 3 carbon atoms; preferably a "$C_{3-6}$ cycloalkyl $C_{1-6}$ alkyl group ($C_{3-6}$ cycloalkyl $C_{1-6}$ alkylene group)" or a "$C_{3-6}$ cycloalkyl $C_{1-3}$ alkyl group ($C_{3-6}$ cycloalkyl $C_{1-3}$ alkylene group)" in which the cycloalkyl group has 3 to 6 carbon atoms. Further, the "heterocycloalkylalkyl group" according to the present invention is preferably a "heterocycloalkyl $C_{1-6}$ alkyl group (heterocycloalkyl $C_{1-6}$ alkylene group)" in which the alkyl group has 1 to 6 carbon atoms; more preferably a "heterocycloalkyl $C_{1-3}$ alkyl group (heterocycloalkyl $C_{1-3}$ alkylene group)" in which the alkyl group has 1 to 3 carbon atoms.

Further, in the present invention, the "cyclic amine" refers to a nitrogen-containing heterocycle having 3 to 8 atoms, and the nitrogen-containing heterocycle may be a monocyclic ring, or may form a fused ring, a crosslinked ring or a spiro ring. Examples of the cyclic amine include, but are not particularly limited to, azetidine, pyrrolidine, piperidine, piperazine, morpholine, thiomorpholine, pyrazole, imidazole, triazole, azepane and azocane. Of these, pyrrolidine, piperidine, piperazine and morpholine are preferable as the "cyclic amine" according to the present invention.

In the present invention, the term "optionally substituted" means that unless otherwise specified, any hydrogen atom bonded to a group described as being optionally substituted is substituted with a substituent (atom or group) selected from the group consisting of other atoms or groups, and the number of positions at which the hydrogen atom is substituted may be 1 or 2 or more. When the number of positions at which the hydrogen atom is substituted is 2 or more, the substituents are the same or different.

In the present invention, examples of the substituents include substituents such as halogen atoms (fluorine atom, chlorine atom, bromine atom and iodine atom), a cyano group, a hydroxyl group, a thiol group, a nitro group, $C_{1-6}$ alkyl groups (preferably $C_{1-3}$ alkyl groups), aryl groups, heteroaryl groups, cycloalkyl groups (preferably $C_{3-6}$ cycloalkyl groups), heterocycloalkyl groups, arylalkyl groups (preferably aryl $C_{1-3}$ alkyl groups), heteroarylalkyl groups (preferably heteroaryl $C_{1-3}$ alkyl groups), cycloalkylalkyl groups (preferably $C_{3-6}$ cycloalkyl $C_{1-3}$ alkyl groups), heterocycloalkylalkyl groups (preferably heterocycloalkyl $C_{1-3}$ alkyl groups); groups represented by the formula: —N($R^{133a}$)—$R^{133b}$ [where $R^{133a}$ and $R^{133b}$ are each independently a hydrogen atom, a $C_{1-6}$ alkyl group (preferably a $C_{1-3}$ alkyl group), a cycloalkyl group (preferably a $C_{3-6}$ cycloalkyl group), an aryl group, a heteroaryl group, or a group represented by the formula: —C(=O)—$R^{133c}$ [where $R^{133c}$ represents a $C_{1-6}$ alkyl group (preferably a $C_{1-3}$ alkyl group), a cycloalkyl group (preferably a $C_{3-6}$ cycloalkyl group), an aryl group or a heteroaryl group], or $R^{133a}$ and $R^{133b}$ are linked together to form a four- to seven-membered ring cyclic amine]; groups represented by the formula: —$R^{134}$—C(=O)—$R^{135}$ [where $R^{134}$ represents a single bond or an alkylene group having 1 to 3 carbon atoms, and $R^{135}$ represents a hydrogen atom, a $C_{1-6}$ alkyl group (preferably a $C_{1-3}$ alkyl group), a cycloalkyl group (preferably a $C_{3-6}$ cycloalkyl group), an aryl group or a heteroaryl group]; groups represented by the formula: —$R^{136}$—C(=O)—O—$R^{137}$ [where $R^{136}$ represents a single bond or an alkylene group having 1 to 3 carbon atoms, and $R^{137}$ represents a hydrogen atom, a $C_{1-6}$ alkyl group (preferably a $C_{1-3}$ alkyl group), a cycloalkyl group (preferably a $C_{3-6}$ cycloalkyl group), an aryl group or a heteroaryl group]; and groups represented by the formula: —$OR^{138}$ [where $R^{138}$ represents a $C_{1-6}$ alkyl group (preferably a $C_{1-3}$ alkyl group), a cycloalkyl group (preferably a $C_{3-6}$ cycloalkyl group), a heterocycloalkyl group, an aryl group, a heteroaryl group, a cycloalkylalkyl group (preferably a $C_{3-6}$ cycloalkyl $C_{1-3}$ alkyl group), a heterocycloalkylalkyl group (preferably a heterocycloalkyl $C_{1-3}$ alkyl group), an arylalkyl group (preferably an aryl $C_{1-3}$ alkyl group) or a heteroarylalkyl group (preferably a heteroaryl $C_{1-3}$ alkyl group)]. Of the substituents and groups involved in formation of the substituents, alkyl groups, aryl groups, heteroaryl groups, cycloalkyl groups and heterocycloalkyl groups may be further substituted with any substituent as in the definition described above.

Among them, when the group substituted is an aryl group or a heteroaryl group which is represented by $R^{102}$, the substituent is particularly preferably a halogen atom, a cyano group, a hydroxyl group, an optionally substituted piperazinyl group (more preferably a piperazinyl group optionally substituted with a $C_{1-6}$ alkyl group), an piperazinyl $C_{1-6}$ alkyl group such as a piperazinylmethyl group which is optionally substituted (more preferably a piperazinyl $C_{1-6}$ alkyl group such as a piperazinylmethyl group which is optionally substituted with a $C_{1-6}$ alkyl group), a morpholinyl group; a group represented by the formula: —N($R^{133a}$)—$R^{133b}$ [where preferably, $R^{133a}$ and $R^{133b}$ each independently represent a hydrogen atom or a $C_{1-3}$ alkyl group]; or a group represented by the formula: —$R^{136}$—C(=O)—O—$R^{137}$ [where preferably, $R^{136}$ represents an alkylene group having 1 to 3 carbon atoms and $R^{137}$ represents a hydrogen atom or a $C_{1-3}$ alkyl group].

When the group substituted is an arylalkylene group which is represented by $R^{113}$; or an alkyl group, an aryl group or a heteroaryl group which is represented by $R^{113}$ or $R^{122}$, the substituent is particularly preferably a halogen atom, a hydroxyl group, a $C_{1-3}$ alkyl group; a group represented by the formula: —N($R^{133a}$)—$R^{133b}$ [where preferably, $R^{133a}$ and $R^{133b}$ each independently represent a hydrogen atom or a $C_{1-3}$ alkyl group]; or a group represented by the formula: —$OR^{13}$ [where preferably, $R^{13}$ represents a $C_{1-3}$ alkyl group].

When the group substituted is an alkyl group, an aryl group or a heteroaryl group which is represented by $R^{115}$ or $R^{116}$, the substituent is particularly preferably a halogen atom, a hydroxyl group, a $C_{1-3}$ alkyl group; a group represented by the formula: —N($R^{133a}$)—$R^{133b}$ [where preferably, $R^{133a}$ and $R^{133b}$ each independently represent a hydrogen atom or a $C_{1-3}$ alkyl group]; or a group represented by the formula: —$OR^{138}$ [where preferably, $R^{138}$ represents a $C_{1-3}$ alkyl group].

When the group substituted is an alkyl group, an aryl group, an arylalkylene group or a heteroaryl group which is represented by $R^{121}$, $R^{123a}$ or $R^{123b}$, the substituent is particularly preferably a halogen atom, a hydroxyl group, a $C_{1-3}$ alkyl group; a group represented by the formula: —N($R^{133a}$)—$R^{133b}$ [where preferably, $R^{133a}$ and $R^{133b}$ each independently represent a hydrogen atom or $C_{1-3}$ alkyl group]; or a group represented by the formula: —$OR^{138}$ [where preferably, $R^{138}$ represents a $C_{1-3}$ alkyl group].

In the formulas (1) and (1a), r represents the number of $R^{101}$, and is 0 to 4. r is preferably 0 (i.e. all the four groups corresponding to $R^{101}$ are hydrogen atoms), or 1 or 2. The position of $R^{101}$ is preferably the 7-position or the 8-position when r is 1 or 2.

In the formulas (1) and (1a), each $R^{101}$ is the same or different when r is 2 or more, and represents a $C_{1-6}$ alkyl group optionally substituted with a halogen atom, $OR^{111}$, or a group represented by the formula: —N($R^{112a}$)—$R^{112b}$. Here, $R^{111}$, $R^{112a}$ and $R^{112b}$ are each independently a hydrogen atom or a $C_{1-6}$ alkyl group.

$R^{101}$ is preferably an unsubstituted $C_{1-6}$ alkyl group; a $C_{1-6}$ alkyl group substituted with a halogen atom; or $OR^{11}$ in which $R^{111}$ is a hydrogen atom or a $C_{1-3}$ alkyl group. More specifically, $R^{101}$ is more preferably a methyl group, an ethyl group, a hydroxyl group or a trifluoromethyl group.

In the formulas (1) and (1a), s represents the number of $R^{102}$, and is 0 to 5. s is preferably 0 (i.e. all the five groups corresponding to $R^{102}$ are hydrogen atoms), or 1 to 3. The position of $R^{o2}$ is preferably the m-position and/or the p-position when r is 1 to 3. The position of $R^{10}$ is preferably the p-position when r is 1.

In the formulas (1) and (1a), each $R^{102}$ is the same or different when s is 2 or more, and represents a halogen atom, $OR^{113}$, a group represented by the formula: —N($R^{114a}$)—$R^{114b}$, a group represented by the formula: —NH—C(=O)—$R^{115}$, a group represented by the formula: —C(=O)—$R^{116}$, an optionally substituted aryl group, an optionally substituted heteroaryl group, a nitro group or a cyano group.

Here, $R^{113}$ is a hydrogen atom, an optionally substituted alkyl group, an optionally substituted aryl group, an optionally substituted arylalkyl group, or an optionally substituted heteroaryl group; $R^{114a}$ and $R^{114b}$ each are independently a hydrogen atom or a $C_{1-6}$ alkyl group; $R^{115}$ is an optionally substituted alkyl group, an optionally substituted aryl group, an optionally substituted heteroaryl group, or a group represented by the formula: —NH—$R^{121}$; and $R^{116}$ is an optionally substituted alkyl group, an optionally substituted aryl group, an optionally substituted heteroaryl group, $OR^{122}$, or a group represented by the formula: —N($R^{123a}$)—$R^{123b}$.

Further, $R^{121}$ is an optionally substituted alkyl group, an optionally substituted aryl group, or an optionally substituted heteroaryl group; $R^{122}$ is a hydrogen atom, an optionally substituted alkyl group, an optionally substituted aryl group, or an optionally substituted heteroaryl group; and $R^{1233}$ and $R^{123b}$ are each independently a hydrogen atom, an optionally substituted alkyl group, an optionally substituted aryl group, or an optionally substituted heteroaryl group, or $R^{123a}$ and $R^{123b}$ are linked together to form a cyclic amine.

$R^{102}$ is preferably a halogen atom; $OR^{113}$ in which $R^{113}$ is an optionally substituted alkyl group, an optionally substituted aryl group or an optionally substituted arylalkyl group; a group represented by the formula: —N($R^{114a}$)—$R^{114b}$ in which $R^{114a}$ and $R^{114b}$ are each independently a hydrogen atom or a $C_{1-3}$ alkyl group; a group represented by the formula: —C(=O)—$R^{16}$ in which $R^{116}$ is $OR^{122}$; an optionally substituted aryl group; an optionally substituted heteroaryl group; a nitro group; or a cyano group, preferably a halogen atom; $OR^{113}$ in which $R^{113}$ is an optionally substituted alkyl group; an optionally substituted aryl group; or an optionally substituted heteroaryl group. More specifically, $R^{102}$ is more preferably a halogen atom; a methoxy group; an ethoxy group; or a phenyl group optionally substituted with a hydroxyl group, a 4-methylpiperazin-1-yl group, a (4-methylpiperazin-1-yl)methyl group, a 4-morpholin-4-yl group or a dimethylamino group.

In the formulas (1) and (1a), $R^{103}$ is a hydrogen atom, a $C_{1-6}$ alkyl group, a $C_{3-6}$ cycloalkyl group, or a $C_{3-6}$ cycloalkyl $C_{1-6}$ alkyl group.

$R^{103}$ is preferably a hydrogen atom, a $C_{1-3}$ alkyl group, $C_{3-6}$ cycloalkyl $C_{1-3}$ alkyl group. More specifically, $R^{103}$ is more preferably a hydrogen atom, a methyl group, or a cyclopropylmethyl group.

In the formulas (1) and (1a), when $R^{101}$ is present at the 8-position, $R^{101}$ and $R^{103}$ present at the 1-position are optionally linked together to form a five- to seven-membered ring hetero ring. The five- to seven-membered ring hetero ring is preferably pyrrolidinyl, piperidinyl or morpholinyl, more preferably pyrrolidinyl or morpholinyl.

Compounds of the formula (1a) do not include compounds of the formula (1) in which $J^1$ represents CH, $J^2$ represents N, r is 0, $R^{103}$ is a hydrogen atom or a methyl group, $R^{10}$ is present at the p-position, and $R^{102}$ is a methoxy group. Such compounds of the formula (1a) and salts thereof are novel dihydroquinazolinone-based compounds.

Examples of preferred aspects of compounds of the formula (1) and (1a) according to the present invention include, but are not limited to, the following aspects (I) to (III), and combinations of two or three of the aspects.

(I) A compound of the above formula (1) or (1a) in which r is 0; or r is 1, $R^{101}$ is present at the 7-position or the 8-position, and $R^{101}$ represents a $C_{1-3}$ alkyl group optionally substituted with a halogen atom or a hydroxy group; or r is 1, $R^{101}$ is present at the 8-position, and $R^{101}$ and $R^{103}$ are linked together to form a five- or six-membered ring hetero ring.

(II) A compound of the above formula (1) or (1a) in which $R^{103}$ represents a hydrogen atom, a $C_{1-3}$ alkyl group or a $C_{3-6}$ cycloalkyl $C_{1-3}$ alkyl group; or r is 1, $R^{101}$ is present at the 8-position, and $R^{101}$ and $R^{103}$ are linked together to form a five- or six-membered ring hetero ring.

(III) A compound of the above formula (1) or (1a) in which s is 0; or S is 1 and $R^{102}$ is a halogen atom, $OR^{113}$ in which $R^{113}$ is an optionally substituted $C_{1-3}$ alkyl group, or an optionally substituted aryl group.

The compounds of the formula (1) and the compounds of the formula (1a) according to the present invention include compounds having microtubule inhibitory activity. Examples the compounds having microtubule inhibitory activity include compounds of the above formulas (1) and (1a) in which each of $J^1$ and $J^2$ is N. Examples thereof include compounds in which r is 1, $R^{101}$ is present at the 8-position, and $R^{103}$ is a hydrogen atom; and compounds in which r is 1, $R^{101}$ is present at the 8-position, and $R^{101}$ and $R^{o3}$ are linked together to form a five- or six-membered ring hetero ring.

Examples of the compounds of the formula (1) according to the present invention include compounds of Examples 1 to 87 shown below, and examples of the compounds of the formula (1a) according to the present invention include compounds of Examples 1 to 81 and 84 to 87 shown below.

In the present invention, the term "pharmacologically acceptable" means being suitable for pharmacological use, and pharmacologically acceptable salts according to the present invention include, but are not particularly limited to, salts of alkali metals or alkali earth metals such as sodium, potassium and calcium; salts of hydrohalic acids such as hydrofluoric acid, hydrochloric acid, hydrobromic acid and hydroiodic acid; salts of inorganic acids such as sulfuric acid, nitric acid, phosphoric acid, perchloric acid and carbonic acid; salts of organic carboxylic acids such as formic acid, acetic acid, trifluoroacetic acid, trichloroacetic acid, hydroxyacetic acid, propionic acid, lactic acid, citric acid, tartaric acid, oxalic acid, benzoic acid, mandelic acid, butyric acid, fumaric acid, succinic acid, maleic acid and malic acid; salts of acidic amino acids such as aspartic acid and glutamic acid; salts of sulfonic acids such as methanesulfonic acid, ethanesulfonic acid, benzenesulfonic acid and toluenesulfonic acid; and solvates such as hydrates and alcoholates.

The compounds of the above formulas (1) and (1a) and salts thereof may have one or more asymmetric carbon atoms depending on the types of substituents and the like, and optically active substances, enantiomers, any mixtures thereof, racemates and the like based on the one or more asymmetric carbon atoms are all within the scope of the present invention. The group having an unsaturated double bond can be present in a cis- or trans-form. Further, the compounds of the above formulas (1) and (1a) and salts thereof express a form of one of possible isomers (rotational isomers, atropisomers and tautomers) in addition to the above-described isomers, and these isomers may be present singly, or present as a mixture thereof. Herein, a compound which has any of the above-described isomers and isotopes and whose name is not particularly specified may be one of the isomers and isotopes, or a mixture or a racemate of two or more of the isomers and isotopes.

The compounds of the formulas (1) and (1a) and pharmacologically acceptable salts thereof according to the present invention (hereinafter, sometimes referred to as "dihydroquinazolinone-based compounds") can be produced through the methods shown below. The method for producing a dihydroquinazolinone-based compound according to the present invention is not limited to the methods shown below, and a scope of the compounds according to the present invention is not limited to compounds produced by the following production methods.

The method for producing a dihydroquinazolinone-based compound according to the present invention can be carried out by combining a wide range of various kinds of synthesis methods known to persons skilled in the art, methods obtained by making a modification or the like to the synthesis methods if necessary, and the like while using starting raw materials, precursors, reagents and solvents which are commercially available or can be synthesized through methods known to persons skilled in the art.

A method for introducing, modifying or converting any substituent or the like can be carried out by introducing, modifying or converting an intended substituent itself or a group convertible to the substituent in a raw material stage, an intermediate material stage or a final-form material stage by combining a wide range of various kinds of synthesis methods known to persons skilled in the art, methods obtained by making a modification or the like to the synthesis methods if necessary, and the like. The method can also be carried out by appropriately changing the order of reaction steps, etc. The method can also be carried out by appropriately employing general means such as protection and deprotection of functional groups which are commonly used in organic synthesis chemistry if necessary for convenience of the reaction (e.g., methods described in, for example, Green Wuts, PROTECTIVE GROUPS in ORGANIC SYNTHESIS THIRD EDITION, John Wiley & Sons, Inc.).

Reaction apparatuses usable in production of the compound include common glass reaction vessels, optionally glass-lined metallic reaction baths, and flow reactors. Examples of cooling or heating at the time of carrying out the reaction include air cooling, water cooling, ice cooling, combination of a cryogen and a cooling medium, and cooling of a reaction vessel or a reaction mixture through a cooling medium cooled by a freezing machine, or heating with hot water or steam, heating of a reaction vessel directly by an electric heater or through a heating medium, and heating by application of an ultrashort electromagnetic wave (i.e. microwave heating). Further, cooling or heating using a Peltier device, etc. can also be performed.

The dihydroquinazolinone-based compound according to the present invention can be prepared through, for example, the following method.
(Production Method)

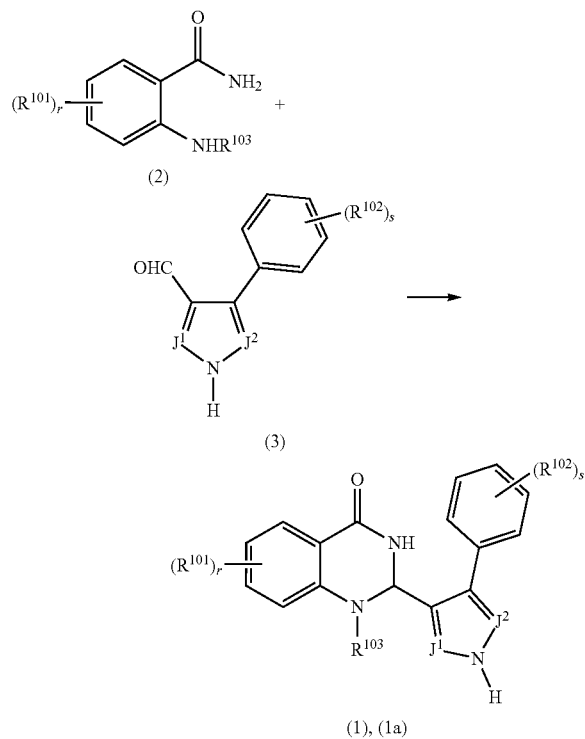

In the above formulas (2) and (3), $J^1$, $J^2$, r, $R^{101}$, s, $R^{102}$ and $R^{103}$ are each independently the same as $J^1$, $J^2$, r, $R^{101}$, s, $R^{102}$ and $R^{103}$ in the above formula (1) or (1a), respectively.

The compound of the formula (2) (hereinafter, referred to as a "raw material (2)" and the compound of the formula (3) (hereinafter, referred to as a "raw material (3)") in the above production method can be obtained as commercially available reagents, or can be synthesized through known methods or methods based on the known methods.

In the above production method according to the present invention, the raw material (2) and the raw material (3) are dissolved or suspended in an appropriate solvent, and reacted in the presence or non-presence of an acid catalyst to produce a dihydroquinazolinone-based compound according to the present invention (a compound of the formula (1) or a salt thereof, or a compound of the formula (1a) or a salt thereof, which is hereinafter sometimes referred to as a "compound (1)" or a "compound (1a)").

In the above production method, the raw material (2) and the raw material (3) are used normally at a molar ratio in the range of 1:1 to 3, preferably at a molar ratio in the range of 1:1 to 1.2.

Examples of the solvent to be used in the above production method include protic solvents such as water, methanol, ethanol, n-propanol, 2-propanol, n-butanol, 2-butanol and tert-butyl alcohol; hydrocarbon-based solvents such as petroleum ether, n-pentane, n-hexane, n-heptane, cyclohexane, benzene, toluene and xylene; halogen-based solvents such as carbon tetrachloride, dichloromethane, chloroform, 1,2-dichloroethane, chlorobenzene and trifluoromethylbenzene; ether-based solvents such as diethyl ether, diisopropyl ether, methyl tert-butyl ether, methyl cyclopentyl ether, tetrahydrofuran, 2-methyltetrahydrofuran, 1,4-dioxane, 1,2-dimethoxyethane and diphenyl ether; ester-based solvents such as methyl acetate, ethyl acetate, n-propyl acetate, isopropyl acetate, n-butyl acetate, isobutyl acetate, tert-butyl acetate, benzyl acetate, methyl propionate, ethyl propionate, n-propyl propionate, isopropyl propionate, n-butyl propionate, isobutyl propionate and tert-butyl propionate; and aprotic polar solvents such as acetone, 2-butanone, methylisobutylketone, cyclohexanone, acetonitrile, propionitrile, N,N-dimethylformamide, N,N-dimethylacetamide, dimethyl sulfoxide and N-methyl-2-pyrrolidone. One of these solvents can be used alone, or two or more thereof can be mixed at an appropriate ratio and used. Of these, at least one of methanol, ethanol, n-propanol and N,N-dimethylformamide is preferably used as the solvent.

Examples of the acid to be used at the time of carrying out the reaction in the presence of the acid catalyst in the above production method include mineral acids such as hydrochloric acid, hydrobromic acid, hydroiodic acid, sulfuric acid, phosphoric acid and nitric acid; carboxylic acids such as formic acid, acetic acid, propionic acid and trifluoroacetic acid; and Lewis acids such as boron trifluoride-diethyl ether complexes, boron trichloride, boron tribromide, zinc chloride, stannic chloride, ferric chloride, aluminum chloride, titanium tetrachloride and zirconium tetrachloride. Of these, at least one of hydrochloric acid, formic acid, acetic acid and propionic acid is preferable, with acetic acid being more preferable, as the acid. The amount of the acid used is in the range of 0.01 to 20 equivalents, preferably in the range of 0.05 to 5 equivalents, more preferably in the range of 0.1 to 1 equivalents, based on the amount of the raw material (2). Alternatively, the amount is in the range of 0.01 to 20 equivalents, preferably in the range of 0.1 to 10 equivalents, more preferably in the range of 1 to 5 equivalents.

In the above production method, the reaction temperature is in the range of 0 to 250° C., preferably 30 to 200° C., more preferably 60 to 160° C. In the above production method, the reaction time is in the range of 1 minute to 2 days, preferably 5 minutes to 12 hours, more preferably 10 minutes to 6 hours.

In the above production method, optional substituents with which $R^{102}$ is substituted may have intended substituents in the stage of the raw material (3). In this case, the resulting compound (1) or compound (1a) has the intended substituents. By introducing, modifying or converting precursor groups for intended substituents in the raw material (3) by combining a wide range of various kinds of synthesis methods known to persons skilled in the art, the compound (1) or compound (1a) having the intended substituents can be produced. These synthesis methods can be arbitrarily combined, and protection, deprotection and the like may be appropriately performed if necessary.

The raw material (3) in the production method according to the present invention can be produced through, for example, methods shown in the following schemes 1 and 2.

(Scheme 1)

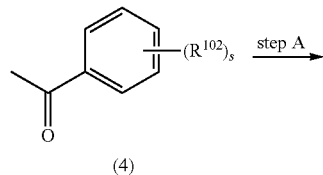

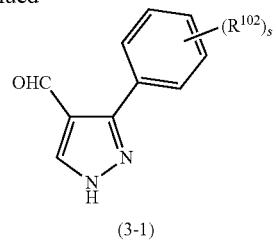

In the above formulas (4), (5) and (3-1), s and $R^{102}$ are each independently the same as s and $R^{102}$ in the above formula (1) or (1a), respectively.

The compound of the formula (4) (hereinafter, referred to as a "raw material (4)") in the scheme 1 can be obtained as a commercially available reagent, or can be synthesized through a known method or a method based on the known method.

The compound of the formula (3-1) (hereinafter, referred to as a "raw material (3-1)") in the scheme 1 is a type of raw material (3). By using a known method such as the method described in Synthesis, 1998, 10, 1140., the raw material (3-1) can be produced from the compound of the formula (5) (compound (5)) which can be synthesized through a condensation reaction of the raw material (4) and semicarbazide hydrochloride. A series of all these synthesis methods are based on methodologies extensively described in general documents of organic chemistry, and the syntheses can be performed through the described methods themselves or modifications thereof.

(Scheme 2)

In the above formulas (6), (7), (8), (9) and (3-2), s and $R^{102}$ are each independently the same as s and $R^{102}$ in the above formula (1) or (1a), respectively.

The compound of the formula (6) (hereinafter, referred to as a "raw material (6)") and the compound of the formula (9) (hereinafter, referred to as a "raw material (9)") in the scheme 2 can be obtained as commercially available reagents, or can be synthesized through known methods or methods based on the known methods.

The compound of the formula (3-2) (hereinafter, referred to as a "raw material (3-2)") in the scheme 2 is a type of raw material (3). The raw material (3-2) can be synthesized by adding sodium azide to the compound of the formula (8)

(compound (8)) (step C: Tetrahedron Letters, 2001, 42, 9117.), and the compound (8) can be synthesized in two steps (step A and step B) from the raw material (6) or in one step (step D) from the raw material (9) (steps A and B: method described in Bioorganic & Medicinal Chemistry Letters, 2008, 184932., etc.; and step D: method described in Tetrahedron Letters, 2001, 42, 9117., etc.). A series of all these synthesis methods are based on methodologies extensively described in general documents of organic chemistry, and the syntheses can be performed through the described methods themselves or modifications thereof.

The dihydroquinazolinone-based compound synthesized through the above production method, the intermediate, the raw material and the like may be used in the next step in a state of a reaction solution or a crude product, or used after being isolated through a common purification method known to persons skilled in the art. Examples of the purification method associated with isolation include methods obtained by appropriately selecting or combining various types of chromatography (column or thin-layer and normal phase or reversed phase chromatography; gel permeation chromatography (GPC) and the like), distillation, sublimation, precipitation, crystallization and centrifugation.

The dihydroquinazolinone-based compounds of the present invention, tautomers and stereoisomers thereof, and mixtures of these compounds at any ratios have an excellent tankyrase inhibitory action and/or microtubule inhibitory action, and thus can be administered alone or in combination with at least one of conventionally known methods for treating a disease including conventional operative treatments, radiation treatments and anticancer agent treatments in treatment of diseases such as various solid tumors and blood tumors as diseases attributable to tankyrase and/or microtubules or intracellular molecular reactions related to the tankyrase and/or microtubules (e.g., fibrosarcoma, ovary cancer, glioblastoma, pancreatic cancer, breast cancer, astrocytoma, lung cancer, gastric cancer, liver cancer, colorectal cancer, bladder cancer and leukemia); infections such as Herpes simplex virus infection and Epstein-Barr virus infection; fibroses such as pulmonary fibrosis; neurodegenerative diseases such as cherubism, multiple sclerosis and amyotrophic lateral sclerosis; various types of inflammatory diseases such as skin and cartilage damages; and metabolic diseases such as obesity.

The cell proliferation inhibitor of the present invention contains the dihydroquinazolinone-based compound of the present invention as an active ingredient. Therefore, the cell proliferation inhibitor of the present invention can be used as a tankyrase inhibitor, a microtubule inhibitor (preferably a microtubule polymerization inhibitor or a microtubule depolymerization inhibitor, more preferably a microtubule polymerization inhibitor), or a pharmaceutical composition (more specifically a prophylactic or therapeutic agent for a disease attributable to tankyrase and/or microtubules), and such an agent can be used as a proliferation suppressive agent or a prophylactic or therapeutic agent for the solid tumors and blood tumors; or a prophylactic or therapeutic agent for the infections, pulmonary fibroses, multiple sclerosis or amyotrophic lateral sclerosis.

In the present invention, the cell proliferation inhibitors include cell proliferation inhibitors in a broad sense, i.e. cell proliferation inhibitors for direct suppression of proliferation of cells of the solid tumors, blood tumors and the like, suppression of invasion and metastasis of the cells, and suppression of tumor angiogenesis, and the cell proliferation inhibitor refers to an agent for suppression, prevention or retardation of proliferation and metastasis of the cells.

The cell proliferation inhibitor of the present invention may further contain therapeutic agents other than the dihydroquinazolinone-based compound of the present invention, or may be used in combination with other therapeutic agents simultaneously or intertemporally. Examples of the other therapeutic agents include other anticancer agents (antiproliferative agents, antineoplastic agents, DNA-damaging agents and combinations thereof). More specifically, alkylating agents (e.g., temozolomide and melphalan); antimetabolites (e.g., gemcitabine, cytarabine (Ara-C), fluorouracil (5-FU), pemetrexed, mercaptopurine and methotrexate); plant alkaloids (e.g., irinotecan (SN-38) and etoposide (VP-16)); anticancer antibiotics (e.g., actinomycin D, daunorubicin, doxorubicin, bleomycin and mitoxantrone); platinating agents (e.g., oxaliplatin, carboplatin and cisplatin); other microtubule inhibitors (e.g., paclitaxel, vinblastine, vincristine, vindesine, vinorelbine, docetaxel, cabazitaxel, eribulin and pharmacologically acceptable salts thereof); mitosis inhibitors; topoisomerase inhibitors; cell division inhibitors; growth factor function inhibitors such as EGFR antibodies; angiogenesis inhibition agonists such as VEGFR antibodies; cancer cell metastasis suppression agonists such as metalloprotease inhibitors; antisense therapeutic drugs such as Ras antisense; and immunotherapeutic drugs with anti-PD-1 antibodies and T-cells. One of these therapeutic agents may be used alone, or two or more thereof may be used in combination.

The cell proliferation inhibitor of the present invention may be administered through any of oral and parenteral administration routs such as routs of inhalation administration, nasal administration, ophthalmic administration, subcutaneous administration, intravenous administration, intramuscular administration, rectal administration and transdermal administration, and can be administered to humans or animals other than humans. Therefore, the cell proliferation inhibitor of the present invention may take an appropriate dosage form depending on an administration route.

Specific examples of the dosage form of the cell proliferation inhibitor of the present invention include oral agents such as tablets, pills, capsules, granules, powders, fine granules, troches, elixirs, suspensions, emulsions and syrups; solutions for external use such as inhalations, nasal solutions and ophthalmic solutions; injections such as intravenous injections and intramuscular injections; and parenteral agents such as rectal administration agents, suppositories, lotions, sprays, ointments, creams and patches.

The cell proliferation inhibitor of the present invention may further contain, depending on the dosage form, excipients such as diluents, extenders, humectants, surfactants, disintegrants, binders, lubricating agents, dispersants, buffering agents, preservatives, solubilizing agents, antiseptics, correctives, soothing agents, stabilizers, lubricants and colorants which are commonly used in the area of pharmaceuticals. Production can be performed through conventional methods using these additives. Examples of the additives include lactose, fructose, glucose, starch, gelatin, magnesium carbonate, synthetic magnesium silicate, talc, magnesium stearate, methylcellulose, carboxymethylcellulose or salts thereof, gum arabic, olive oil, propylene glycol, polyethylene glycol, syrup, vaseline, glycerin, ethanol, citric acid, sodium chloride, sodium sulfite and sodium phosphate.

In cell proliferation inhibitor of the present invention, the content of the dihydroquinazolinone-based compound of the present invention (in the case where the dihydroquinazolinone-based compound is a mixture of a compound of the above formula (1) or (1a), a pharmacologically acceptable salt thereof, a tautomer and a stereoisomer thereof, and the like, the total content of these components is regarded as the content of the dihydroquinazolinone-based compound) is appropriately adjusted depending on a dosage form of the agent, and therefore may vary, and the content of the dihydroquinazolinone-based compound is typically 0.01 to 70 mass %, preferably 0.05 to 50 mass %, in terms of a free form, based on the total mass of the cell proliferation inhibitor. The dosage of the dihydroquinazolinone-based compound of the present invention (in the case where the dihydroquinazolinone-based compound is a mixture of a compound of the above formula (1) or (1a), a pharmacologically acceptable salt thereof, a tautomer and a stereoisomer thereof, and the like, the total amount of these components is regarded as the amount of the dihydroquinazolinone-based compound) is appropriately adjusted depending on an individual case with consideration given to the dose regimen and the age, the body weight, the sex, the type of disease and the severity of a symptom of a patient, and the like, and therefore may vary, and the dosage of the dihydroquinazolinone-based compound is typically 0.1 to 2,000 mg, preferably 1 to 1,000 mg, in terms of a free form, per day per adult. This amount of the dihydroquinazolinone-based compound is administered once or in several divided doses a day.

EXAMPLES

Hereinafter, the present invention will be described in more detail on the basis of Examples, which should not be construed as limiting the scope of the present invention. Various applications, changes, modifications and the like can be made without departing from the scope of the present invention. Further, methods for producing intermediates and raw materials used in Examples will be described in Reference Examples, which are examples shown for explaining implementation of the present invention in detail, and are should not be construed as limiting the scope of the present invention. Various applications, changes, modifications and the like can be made without departing from the scope of the present invention.

Abbreviations used in Examples and Reference Examples below have the following meanings.

M: mol/L $^1$H-NMR: proton nuclear magnetic resonance spectrum (270 MHz or 500 MHz)

MS (ESI): mass spectrum (electrospray ionization method)

DMSO: dimethyl sulfoxide

Bn: benzyl

TFA: trifluoroacetic acid

Reference Example 1

Methyl 4-(4-formyl-1H-pyrazol-3-yl)benzoate

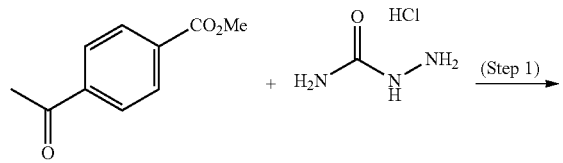

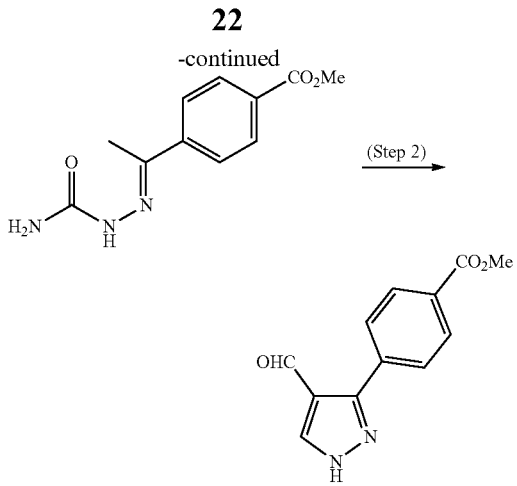

<Step 1>

Methyl 4-acetylbenzoate (2.08 g) was suspended in methanol (40 mL). To this, an aqueous solution (40 mL) of sodium acetate (1.24 g) and semicarbazide hydrochloride (1.43 g) was added. The mixture was refluxed under heating for 5 hours, and allowed to cool to room temperature, water (20 mL) was then added, and the mixture was stirred for several minutes. The precipitated solid was taken by filtration, washed with 100 mL of water, and then air-dried to give methyl (E)-4-(1-2-carbamoylhydrazono)ethylbenzoate (2.66 g) as a white solid.

MS(ESI) m/z: 236.12 [M+H]$^+$

<Step 2>

Methyl (E)-4-(1-2-carbamoylhydrazono)ethylbenzoate (5.05 g) was dissolved in N,N-dimethylformamide (50 mL), and the solution was cooled in an ice bath. Phosphorus oxychloride (17.5 mL) was added dropwise while an internal temperature of 5 to 10° C. was maintained. The mixture was stirred at 5° C. for 30 minutes, then heated to an internal temperature of 65° C., stirred for 4.5 hours, and cooled to room temperature. Thereafter, the reaction mixture was added little by little to ice water (200 mL) to terminate the reaction. A 25% sodium hydroxide aqueous solution was added dropwise to adjust the pH to 7.0. The precipitated solid was taken by filtration, washed with water (30 mL×3), and then dried by heating under reduced pressure (50° C.) to give the title compound (3.80 g) as a light brown solid.

$^1$H-NMR (270 MHz, DMSO-d$_6$) δ: 3.89 (s, 3H), 8.05 (brs, 4H), 8.66 (brs, 1H), 9.95 (s, 1H), 13.88 (brs, 1H).

MS (ESI) m/z: 231.12 [M+H]$^+$.

Reference Example 2

5-(4-(2,2,2-Trifluoroethoxy)phenyl)-2H-1,2,3-triazole-4-carbaldehyde

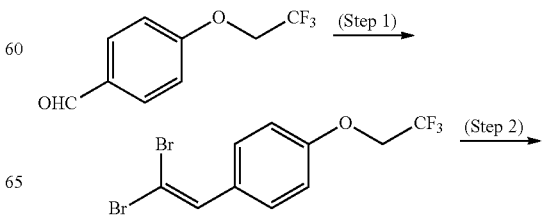

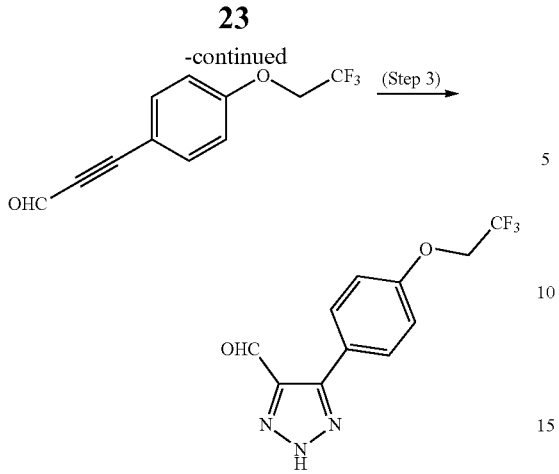

<Step 1>

Carbon tetrabromide (6.5 g) was dissolved in dichloromethane (35 mL), and the solution was cooled to −20° C. To this, a dichloromethane solution (35 mL) of triphenylphosphine (5.14 g) was added dropwise at −20° C. The mixture was stirred for 1 hour, and a solution obtained by dissolving 4-(2,2,2-trifluoroethoxy)benzaldehyde (2.00 g) and triethylamine (1.37 mL) in dichloromethane (20 mL) was then added dropwise at −20° C. The mixture was heated to room temperature, and stirred for 4 hours, and petroleum ether (100 mL) was then added dropwise. The insoluble matter was separated by filtration, and washed with a dichloromethane/petroleum ether mixed solvent (1/1). The filtrate was concentrated, and the brown oil thus obtained was purified by silica gel chromatography (hexane/ethyl acetate=100/0 to 90/10) to give 1-(2,2-dibromovinyl)-4-(2,2,2-trifluoroethoxy)benzene (2.21 g) as a colorless and transparent oil.

$^1$H-NMR (270 MHz, CDCl$_3$) δ: 4.36 (q, J=7.9 Hz, 2H), 6.89-6.98 (m, 2H), 7.42 (s, 1H), 7.49-7.58 (m, 2H).

<Step 2>

1-(2,2-Dibromovinyl)-4-(2,2,2-trifluoroethoxy)benzene (2.05 g) was dissolved in tetrahydrofuran (40 mL), and the solution was cooled to −78° C. A hexane solution of n-butyllithium (1.6 M solution; 7.47 mL) was added dropwise at −78° C., and the mixture was stirred at −78° C. for 2 hours. Subsequently, N,N-dimethylformamide (661 μL) was then added dropwise at −78° C., and the mixture was then heated to room temperature, and stirred for 2.5 hours. The reaction mixture was added dropwise to a mixed solution of a 10% potassium dihydrogenphosphate aqueous solution (40 mL) and methyl tert-butyl ether (40 mL) to terminate the reaction. The organic layer was separated, washed with water (80 mL×2), washed with brine (80 mL), dried over magnesium sulfate, and concentrated. The residue thus obtained was purified by silica gel column chromatography (hexane/ethyl acetate=100/0 to 70/30) to give 3-(4-(2,2,2-trifluoroethoxy)phenyl)propiolaldehyde (283 mg) as a yellow crystalline solid.

$^1$H-NMR (270 MHz, DMSO-d$_6$) δ: 4.40 (q, J=7.9 Hz, 2H), 6.94-7.01 (m, 2H), 7.57-7.64 (m, 2H), 9.41 (s, 1H).

<Step 3>

A dimethyl sulfoxide solution (1 mL) of 3-(4-(2,2,2-trifluoroethoxy)phenyl)propiolaldehyde (275 mg) was added dropwise to a dimethyl sulfoxide solution (2.6 mL) of sodium azide (86.2 mg) at room temperature, and the reaction mixture was stirred at room temperature for 1 hour. The reaction mixture was added dropwise to a mixed solution of a 15% potassium dihydrogenphosphate aqueous solution (10 mL) and methyl tert-butyl ether (10 mL) to terminate the reaction. The organic layer was separated, washed with water (10 mL×2), washed with brine (10 mL), and dried over magnesium sulfate. The solvent was concentrated to give the title compound (315 mg) as a light yellow solid.

$^1$H-NMR (270 MHz, DMSO-d$_6$) δ: 4.87 (q, J=8.9 Hz, 2H), 7.20-7.27 (m, 2H), 7.96-8.03 (m, 2H), 10.17 (s, 1H).

MS (ESI) m/z: 272.13 [M+H]$^+$.

Reference Example 3

5-(4-Propoxyphenyl)-2H-1,2,3-triazole-4-carbaldehyde

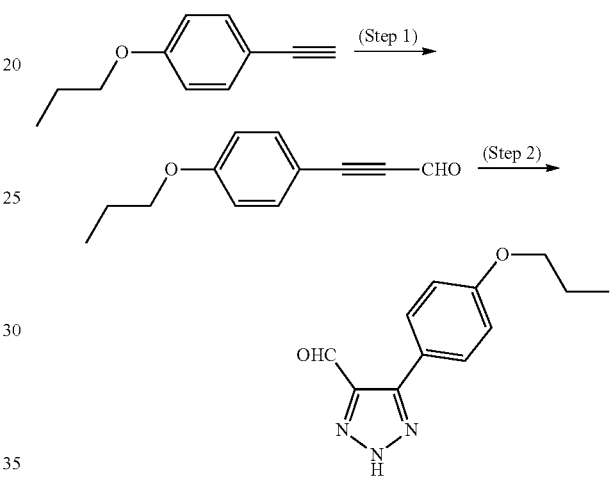

<Step 1>

1-Ethynyl-4-propoxybenzene (5.00 g) was dissolved in tetrahydrofuran (35 mL), and the solution was cooled to −40° C. A hexane solution of n-butyllithium (1.6 M solution; 23.4 mL) was added dropwise at −40° C., and the mixture was stirred at −40° C. for 20 minutes. Subsequently, N,N-dimethylformamide (4.83 mL) was added dropwise at −40° C., and the mixture was then heated to room temperature, and stirred for 1 hour. The reaction mixture was added dropwise to a mixed solution of a 10% potassium dihydrogenphosphate aqueous solution (200 mL) and methyl tert-butyl ether (200 mL) to terminate the reaction. The organic layer was separated, washed with water (100 mL×2), washed with brine (100 mL), dried over magnesium sulfate, and concentrated. The residue thus obtained was purified by silica gel column chromatography (hexane/ethyl acetate=100/0 to 90/10) to give 3-(4-propoxyphenyl)propiolaldehyde (4.60 g) as a yellow crystalline solid.

$^1$H-NMR (270 MHz, CDCl$_3$) δ: 1.04 (t, J=7.4 Hz, 3H), 1.74-1.90 (m, 2H), 3.96 (t, J=6.9 Hz, 2H), 6.85-6.93 (m, 2H), 7.49-7.59 (m, 2H), 9.40 (brs, 1H).

<Step 2>

The title compound (5.12 g) was prepared from 3-(4-propoxyphenyl)propiolaldehyde (4.30 g) in a manner similar to that of <Step 3> of Reference Example 2.

$^1$H-NMR (270 MHz, DMSO-d$_6$) δ: 1.00 (t, J=7.4 Hz, 3H), 1.68-1.84 (m, 2H), 4.01 (t, J=6.6 Hz, 2H), 7.06-7.13 (m, 2H), 7.92-7.99 (m, 2H), 10.16 (s, 1H).

MS (ESI) m/z: 232.14 [M+H]$^+$.

Reference Example 4

5-(4-(2,2-Difluoroethoxy)phenyl)-2H-1,2,3-triazole-4-carbaldehyde

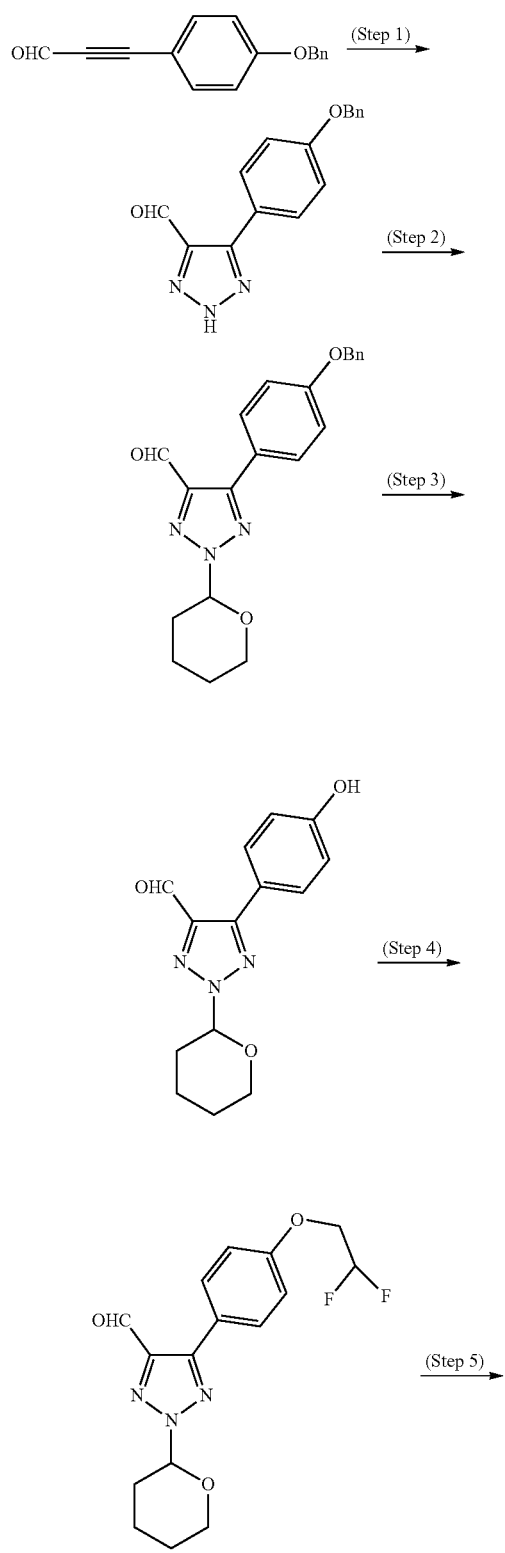

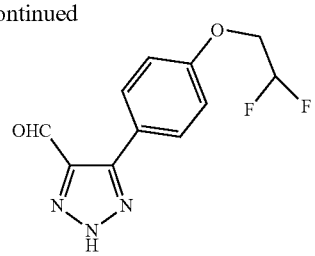

<Step 1>

5-(4-(Benzyloxy)phenyl)-2H-1,2,3-triazole-4-carbaldehyde (1.16 g) was prepared from 3-(4-benzyloxy)phenyl-propiolaldehyde (1.00 g) in a manner similar to that of <Step 3> of Reference Example 2.

$^1$H-NMR (270 MHz, DMSO-$d_6$) δ: 5.20 (s, 2H), 7.15-7.22 (m, 2H), 7.31-7.52 (m, 5H), 7.92-7.99 (m, 2H), 10.16 (s, 1H).

MS (ESI) m/z: 280.19 [M+H]$^+$.

<Step 2>

5-(4-(Benzyloxy)phenyl)-2H-1,2,3-triazole-4-carbaldehyde (200 mg) was dissolved in tetrahydrofuran (2 mL), 3,4-dihydro-2H-pyran (196 μL) and p-toluenesulfonic acid monohydrate (13.6 mg) were added, and the mixture was stirred at room temperature for 2.5 hours. The reaction mixture was diluted with ethyl acetate (10 mL), and then washed with saturated sodium bicarbonate water (10 mL), and then with brine (10 mL), and dried over magnesium sulfate. The solvent was concentrated, and the residue thus obtained was purified by silica gel column chromatography (hexane/ethyl acetate=92/8 to 71/29) to give 5-(4-(benzyloxy)phenyl-2-(tetrahydro-2H-pyran-2-yl)-2H-1,2,3-triazole-4-carbaldehyde (261 mg) as a white solid.

$^1$H-NMR (270 MHz, CDCl$_3$) δ: 1.67-1.84 (m, 3H), 2.09-2.21 (m, 2H), 2.39-2.54 (m, 1H), 3.74-3.89 (m, 1H), 4.03-4.13 (m, 1H), 5.13 (s, 2H), 5.81 (dd, J=8.6, 2.6 Hz, 1H), 7.03-7.09 (m, 2H), 7.30-7.48 (m, 5H), 8.02-8.12 (m, 2H), 10.24 (s, 1H).

<Step 3>

5-(4-(Benzyloxy)phenyl)-2-(tetrahydro-2H-pyran-2-yl)-2H-1,2,3-triazole-4-carbaldehyde (244 mg) was dissolved in tetrahydrofuran (5 mL), 20% palladium hydroxide-carbon (containing about 50% of water; 50 mg) was added, and the mixture was vigorously stirred at room temperature for 80 minutes in a hydrogen atmosphere. A mixed solvent (10 mL) of chloroform/methanol (9/1) was added, the mixture was filtered through Celite, and the filtrate was concentrated. The residue was purified by silica gel column chromatography (hexane/ethyl acetate=80/20 to 50/50) to give 5-(4-hydroxyphenyl)-2-(tetrahydro-2H-pyran-2-yl)-2H-1,2,3-triazole-4-carbaldehyde (147 mg) as a white solid.

$^1$H-NMR (270 MHz, CDCl$_3$) δ: 1.65-1.86 (m, 3H), 2.07-2.22 (m, 2H), 2.39-2.57 (m, 1H), 3.75-3.87 (m, 1H), 4.03-4.16 (m, 1H), 5.22 (brs, 1H), 5.82 (dd, J=8.6, 2.6 Hz, 1H), 6.87-6.97 (m, 2H), 7.99-8.07 (m, 2H), 10.24 (s, 1H).

<Step 4>

5-(4-Hydroxyphenyl)-2-(tetrahydro-2H-pyran-2-yl)-2H-1,2,3-triazole-4-carbaldehyde (61.6 mg) was dissolved in N,N-dimethylformamide (2 mL), cesium carbonate (147 mg) was added, and the mixture was stirred at room temperature for 5 minutes. To this, 1,1-difluoro-2-iodoethane (29.8 μL) was added, and the mixture was stirred at 50° C. for 3 hours, and cooled to room temperature. Thereafter, water (10 mL) and ethyl acetate (10 mL) were added, and the mixture was separated. The aqueous layer was extracted with ethyl acetate (5 mL). The organic layers were combined, washed with water (10 mL×2), and then with brine (10 mL), dried over magnesium sulfate, and concentrated. The residue thus obtained was purified by silica gel column chromatography (hexane/ethyl acetate=90/10 to 70/30) to give 5-(4-(2,2-difluoroethoxy)phenyl)-2-(tetrahydro-2H-pyran-2-yl)-2H-1,2,3-triazole-4-carbaldehyde (71.5 mg) as a colorless and transparent oil.

$^1$H-NMR (270 MHz, CDCl$_3$) δ: 1.66-1.85 (m, 3H), 2.08-2.23 (m, 2H), 2.39-2.55 (m, 1H), 3.74-3.87 (m, 1H), 4.06-4.17 Cm, 1H), 4.24 (td, J=13.0, 4.0 Hz, 2H), 5.82 (dd, J=8.6, 2.6 Hz, 1H), 6.12 (tt, J=55.1, 4.1 Hz, 1H), 6.97-7.04 (m, 2H), 8.07-8.14 (m, 2H), 10.24 (s, 1H).

<Step 5>

5-(4-(2,2-Difluoroethoxy)phenyl)-2-(tetrahydro-2H-pyran-2-yl)-2H-1,2,3-triazole-4-carbaldehyde (64.1 mg) was dissolved in 1,4-dioxane (1 mL), a 4 M hydrogen chloride/1,4-dioxane solution (1 mL) was added at room temperature, and the mixture was stirred. After 1 hour, methanol (1 mL) and a 4 M hydrogen chloride/1,4-dioxane solution (1 mL) were added, and the mixture was further stirred for 1 hour. The solvent was concentrated, and the residue was diluted with ethyl acetate (5 mL), and washed with saturated sodium bicarbonate water (5 mL). The aqueous layer was extracted with ethyl acetate (5 mL). The organic layers were combined, washed with brine (10 mL), and dried over magnesium sulfate. The solvent was concentrated to give the title compound (31.2 mg) as a white solid.

$^1$H-NMR (270 MHz, DMSO-d$_6$) δ: 4.33-4.50 (m, 2H), 6.43 (tt, J=54.4, 3.6 Hz, 1H), 7.14-7.24 (m, 2H), 7.94-8.03 (m, 2H), 10.16 (s, 1H).

MS (ESI) m/z: 254.11 [M+H]$^+$.

Reference Example 5

3,4-Dihydro-2H-benzo[b][1,4]oxazine-5-carboxamide

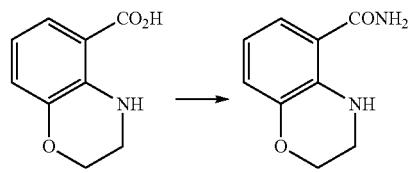 [SMILES: O=C(O)c1cccc2c1NCCO2 ; NC(=O)c1cccc2c1NCCO2]

3,4-Dihydro-2H-benzo[b][1,4]oxazine-5-carboxylic acid (150 mg) and 1-hydroxybenzotriazole (170 mg) were dissolved in N,N-dimethylformamide (1 mL), 1-ethyl-3-(3-dimethylaminopropyl)carbodiimide hydrochloride (241 mg) was added, and the mixture was stirred for 5 minutes. The reaction mixture was cooled with ice, aqueous ammonia (28%; 1 mL) was added dropwise, and the mixture was then stirred for 1 hour. To this, water (4 mL) was added, the mixture was stirred, and the precipitated solid was taken by filtration. The solid was washed with water, and dried by heating under reduced pressure to give the title compound (98.6 mg) as a white solid.

$^1$H-NMR (270 MHz, CDCl$_3$) δ: 3.51 (td, J=4.5, 2.6 Hz, 2H), 4.22 (t, J=4.0 Hz, 2H), 5.72 (brs, 2H), 6.50 (t, J=7.6 Hz, 1H), 6.84-6.90 (m, 1H), 6.98 (dd, J=7.9, 1.3 Hz, 1H), 7.64 (brs, 1H).

MS (ESI) m/z: 179.06 [M+H]$^+$.

The compounds of Reference Examples 6 to 19 shown in Tables 1 and 2 below were prepared using the methods of Reference Examples 1 to 5 and methods based thereon, and methods disclosed in literatures and methods based thereon.

TABLE 1

| Reference Example | Compound name | Structural Formula | $^1$H NMR (270 MHz) δ ppm | Solvent | ESI MS m/z |
|---|---|---|---|---|---|
| 6 | (E)-2-(1-(4-(Benzyloxy)-3-fluorophenyl)ethylidene)hydrazine-1-carboxamide | | | | 302.27 [M + H]+ |
| 7 | 3-(4-(Benzyloxy)-3-fluorophenyl)-1H-pyrazole-4-carbaldehyde | | 5.22 (s, 2 H), 7.05-7.16 (m, 1 H), 7.32-7.55 (m, 7 H), 8.16 (s, 1 H), 9.98 (s, 1 H) | CDC13 | 297.23 [M + H]+ |

TABLE 1-continued

| Reference Example | Compound name | Structural Formula | ¹H NMR (270 MHz) δ ppm | Solvent | ESI MS m/z |
|---|---|---|---|---|---|
| 8 | (E)-2-(1-(3,5-Difluoro-4-methoxyphenyl)ethylidene)hydrazine-1-carboxamide | | | | 244.21 [M + H]+ |
| 9 | 3-(3,5-Difluoro-4-methoxyphenyl)-1H-pyrazole-4-carbaldehyde | | 3.99 (s, 3 H), 7.73-7.84 (m, 2 H), 8.55 (s, 1 H), 9.90 (s, 1 H) | DMSO-d6 | 239.22 [M + H]+ |
| 10 | 5-(4-Ethoxyphenyl)-2H-1,2,3-triazole-4-carbaldehyde | | 1.36 (t, J = 7.0 Hz, 3 H), 4.11 (q, J = 7.0 Hz, 2 H), 7.09 (d, J = 8.6 Hz, 2 H), 7.96 (d, J = 8.6 Hz, 2 H), 10.16 (s, 1 H) | DMSO-d6 | 218.13 [M + H]+ |
| 11 | 1-(2,2-Dibromovinyl)-4-(difluoromethoxy)benzene | | 6.54 (t, J = 72.9 Hz, 1 H), 7.12 (d, J = 8.9 Hz, 2 H), 7.45 (s, 1 H), 7.54 (d, J = 8.9 Hz, 2 H) | CDCl3 | |
| 12 | 3-(4-(Difluoromethoxy)phenyl)propiolaldehyde | | 6.58 (t, J = 72.5 Hz, 1 H), 7.12-7.20 (m, 2 H), 7.57-7.68 (m, 2 H), 9.42 (s, 1 H) | CDCl3 | |

TABLE 2

| Reference Example | Compound name | Structural Formula | ¹H NMR (270 MHz) δ ppm | Solvent | ESI MS m/z |
|---|---|---|---|---|---|
| 13 | 5-(4-(Difluoromethoxy)phenyl)-2H-1,2,3-triazole-4-carbaldehyde | | 7.00-7.72 (m, 3 H), 8.05 (br d, J = 8.6 Hz, 2 H), 10.18 (s, 1 H) | DMSO-d6 | 240.08 [M + H]+ |
| 14 | 3-(4-Isopropoxyphenyl)propiolaldehyde | | 1.36 (d, J = 6.3 Hz, 6 H), 4.61 (spt, J = 6.0 Hz, 1 H), 6.84-6.92 (m, 2 H), 7.50-7.58 (m, 2 H), 9.40 (s, 1 H) | CDCl3 | |

TABLE 2-continued

| Reference Example | Compound name | Structural Formula | $^1$H NMR (270 MHz) δ ppm | Solvent | ESI MS m/z |
|---|---|---|---|---|---|
| 15 | 5-(4-Isopropoxyphenyl)-2H-1,2,3-triazole-4-carbaldehyde | | 1.30 (d, J = 5.9 Hz, 6 H), 4.73 (spt, J = 5.9 Hz, 1 H), 7.08 (d, J = 8.9 Hz, 2 H), 7.91 (d, J = 8.6 Hz, 2 H), 10.16 (s, 1 H) | DMSO-d6 | 232.14 [M + H]+ |
| 16 | 3-(4-(Methoxy-d$_3$)phenyl)propiolaldehyde | | 6.87-6.95 (m, 2 H), 7.54-7.60 (m, 2 H), 9.40 (s, 1 H) | CDCl3 | |
| 17 | 5-(4-(Methoxy-d$_3$)phenyl)-2H-1,2,3-triazole-4-carbaldehyde | | 7.11 (m, J = 8.9 Hz, 2 H), 7.96 (m, J = 8.9 Hz, 2 H). 10.16 (s. 1 H) | DMSO-d6 | 207.15 [M + H]+ |
| 18 | Ethyl 2-(4-(5-formyl-2-(tetrahydro-2H-pyran-2-yl)-2H-1,2,3-triazol-4-yl)phenoxyacetate | | 1.31 (t, J = 7.3 Hz, 3 H), 1.66-1.86 (m, 3 H), 2.09-2.22 (m, 2 H), 2.39-2.55 (m, 1 H), 3.74-3.87 (m, 1 H), 4.04-4.16 (m, 1 H), 4.29 (q, J = 7.1 Hz, 2 H), 4.67 (s, 2 H), 5.82 (dd, J = 8.6, 2.6 Hz, 1 H), 6.95-7.04 (m, 2 H), 8.06-8.13 (m, 2 H), 10.24 (s, 1 H) | CDCl3 | |
| 19 | Ethyl 2-(4-(5-formyl-2H-1,2,3-triazol-4-yl)phenoxyacetate | | 1.23 (t, J = 7.0 Hz, 3 H), 4.19 (q, J = 7.0 Hz, 2 H), 4.88 (s, 2 H), 7.06-7.14 (m, 2 H), 7.91-7.99 (m, 2 H), 10.16 (s, 1 H) | DMSO-d6 | 276.18 [M + H]+ |

Example 1

Methyl 4-[4-(1-methyl-4-oxo-2,3-dihydroquinazolin-2-yl)-1H-pyrazol-5-yl]benzoate

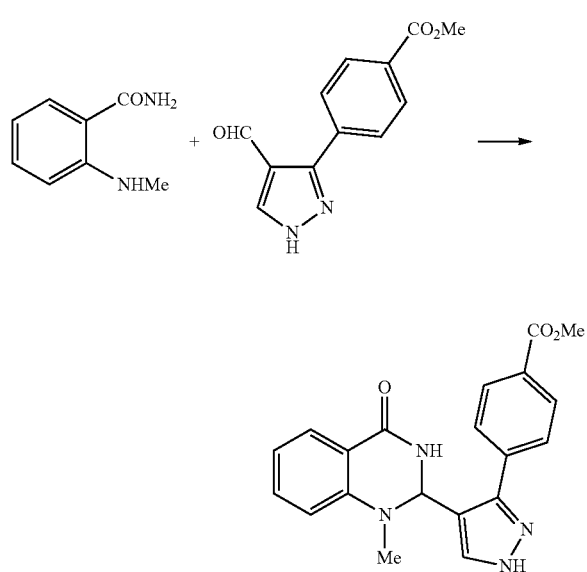

2-(Methylamino)benzamide (500 mg) and acetic acid (50 µL) were added to an ethanol solution (20 mL) of methyl 4-(4-formyl-1H-pyrazol-3-yl)benzoate (920 mg), and the mixture was refluxed under heating for 19 hours, and cooled to room temperature. Thereafter, the solvent was concentrated, and the residue was purified by silica gel chromatography (chloroform/methanol=99/1 to 95/5) to give the title compound (1.34 g) as a white solid.

$^1$H-NMR (270 MHz, DMSO-$d_6$) δ: 3.87 (s, 3H), 5.84 (brs, 1H), 6.71 (d, J=8.2 Hz, 1H), 6.84 (t, J=7.4 Hz, 1H), 7.24-7.50 (m, 1H), 7.57 (brs, 1H), 7.72-7.77 (m, 1H), 7.78-7.94 (m, 2H), 7.94-8.10 (m, 2H), 8.32 (s, 1H), 8.53 (brs, 1H).

MS (ESI) m/z: 363.24 [M+H]$^+$.

Example 2

4-[4-(1-Methyl-4-oxo-2,3-dihydroquinazolin-2-yl)-1H-pyrazol-5-yl]benzoic Acid

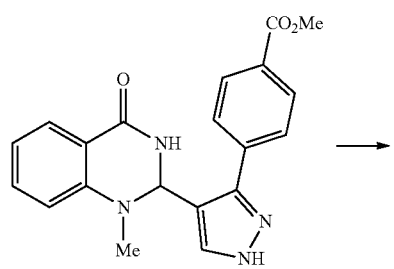

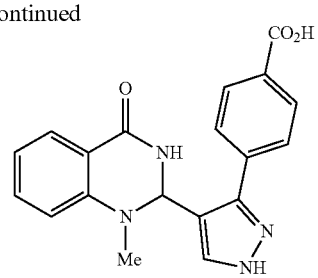

A 1 M potassium hydroxide solution (828 µL) was added to a methanol solution (4 mL) of methyl 4-[4-(1-methyl-4-oxo-2,3-dihydroquinazolin-2-yl)-1H-pyrazol-5-yl]benzoate (200 mg) at room temperature, and the mixture was stirred overnight, further heated to 60° C., stirred for 5 hours, and cooled to room temperature. Thereafter, 1 M hydrochloric acid (828 µL) was added dropwise to perform neutralization. Water (4 mL) was added, the mixture was stirred for 10 minutes, and the precipitated solid was then taken by filtration, washed with water, and then dried by heating under reduced pressure to give the title compound (140 mg) as a white solid.

$^1$H-NMR (270 MHz, DMSO-$d_6$) δ: 5.81 (brs, 1H), 6.71 (brd, J=8.2 Hz, 1H), 6.84 (t, J=7.4 Hz, 1H), 7.32-7.49 (m, 2H), 7.72-7.86 (m, 3H), 7.94-8.07 (m, 2H), 8.54 (brs, 1H), 13.12 (brs, 2H).

MS (ESI) m/z: 349.22 [M+H]$^+$.

Example 3

2-[3-(4-Aminophenyl)-1H-pyrazol-4-yl]-1-methyl-2,3-dihydroquinazolin-4-one

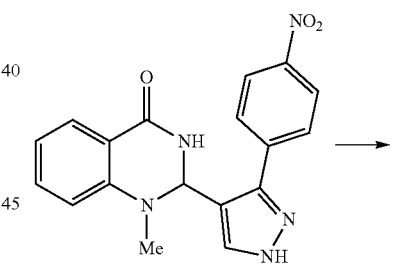

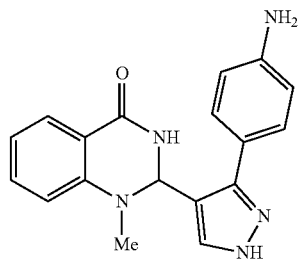

Ammonium chloride (61 mg) and iron powder (144 mg) were added to a mixture of 1-methyl-2-[3-(4-nitrophenyl)-1H-pyrazol-4-yl]-2,3-dihydroquinazolin-4-one (100 mg), ethanol (20 mL), water (7 mL) and tetrahydrofuran (5 mL), and the resulting mixture was refluxed under heating for 3 hours, and cooled to room temperature. Thereafter, the insoluble matter was separated by filtration through Celite, and washed with ethanol. The filtrate was concentrated, and the solid thus obtained was dissolved in a mixed solvent (30 mL) of chloroform/methanol (9/1), washed with brine (10 mL), and then dried over magnesium sulfate. The solvent was concentrated, and the residue thus obtained was purified by silica gel chromatography (chloroform/methanol=98/2 to 90/10) to give the title compound (73.7 mg) as a yellow solid.

$^1$H-NMR (270 MHz, DMSO-d$_6$) δ: 2.46 (s, 3H), 5.37 (brs, 2H), 5.60 (brs, 1H), 6.57-6.73 (m, 3H), 6.83 (t, J=7.4 Hz, 1H), 7.12 (brs, 1H), 7.19-7.32 (m, 2H), 7.39 (brt, J=7.1 Hz, 1H), 7.75 (brd, J=6.3 Hz, 1H), 8.46 (brs, 1H), 12.82 (brs, 1H).

MS (ESI) m/z: 320.29 [M+H]$^+$.

Example 4

N-[4-[4-(1-Methyl-4-oxo-2,3-dihydroquinazolin-2-yl)-1H-pirazol-3-yl]phenyl]benzamide

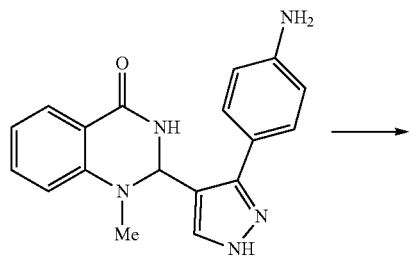

2-[3-(4-Aminophenyl)-1H-pyrazol-4-yl]-1-methyl-2,3-dihydroquinazolin-4-one (20.0 mg) and benzoic acid (9.18 mg) were dissolved in DMF (0.5 mL), 4-(4,6-dimethoxy-1,3,5-triazin-2-yl)-4-methylmorpholinium chloride (20.8 mg) was added, and the mixture was stirred overnight at room temperature. The solvent was concentrated, and the residue was purified by silica gel chromatography (chloroform/methanol=100/0 to 90/10) to give the title compound (21.6 mg) as a white solid.

$^1$H-NMR (270 MHz, DMSO-d$_6$) δ: 5.74 (brs, 1H), 6.71 (d, J=8.2 Hz, 1H), 6.85 (t, J=7.3 Hz, 1H), 7.23-7.68 (m, 7H), 7.76 (dd, J=7.6, 1.6 Hz, 1H), 7.84-8.02 (m, 4H), 8.44-8.59 (m, 1H), 10.38 (s, 1H).

MS (ESI) m/z: 424.41 [M+H]$^+$.

Example 5

1-[3-[4-(1-Methyl-4-oxo-2,3-dihydroquinazolin-2-yl)-1H-pyrazol-3-yl]phenyl]-3-phenylurea

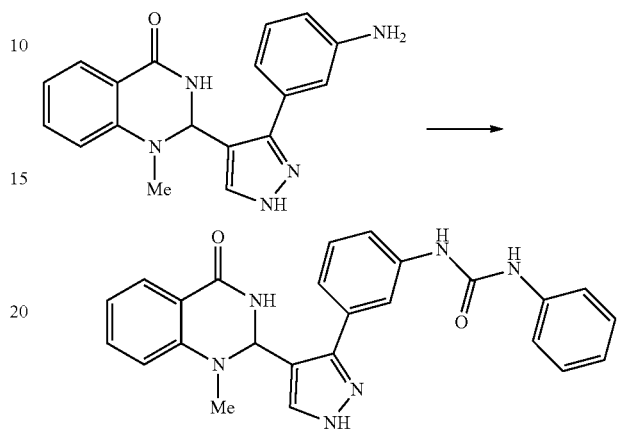

2-[3-(3-Aminophenyl)-1H-pyrazol-4-yl]-1-methyl-2,3-dihydroquinazolin-4-one (30 mg) was dissolved in tetrahydrofuran (1 mL), triethylamine (17.1 μL) was added, and the mixture was cooled with ice. To this solution was added phenyl isocyanate (11.2 μL), and the mixture was stirred at 0° C. for 3 hours. To the reaction mixture were added a mixed solvent (10 mL) of chloroform/methanol (9/1) and a 5% saline solution (10 mL), the mixture was stirred, and the insoluble matter was separated by filtration. The filtrate was concentrated, and the residue was purified by amino silica gel chromatography (chloroform/methanol=100/0 to 95/5) to give the title compound (12.5 mg) as a white solid.

$^1$H-NMR (270 MHz, CDCl$_3$) δ: 2.73 (s, 3H), 5.83 (d, J=3.3 Hz, 1H), 6.68 (d, J=8.2 Hz, 1H), 6.72-6.81 (m, 1H), 6.85-7.03 (m, 3H), 7.11-7.26 (m, 2H), 7.31-7.47 (m, 5H), 7.54-7.62 (m, 2H), 7.93 (dd, J=7.7, 1.5 Hz, 1H), 8.09 (s, 1H), 9.11 (s, 1H).

MS (ESI) m/z: 439.45 [M+H]$^+$.

Example 6

1-Methyl-2-[5-[4-[4-(4-methylpiperazin-1-yl)phenyl]phenyl]-1H-pirazol-4-yl]-2,3-dihydroquinazolin-4-one

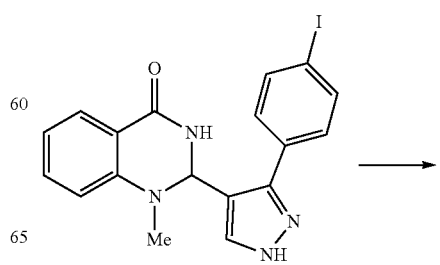

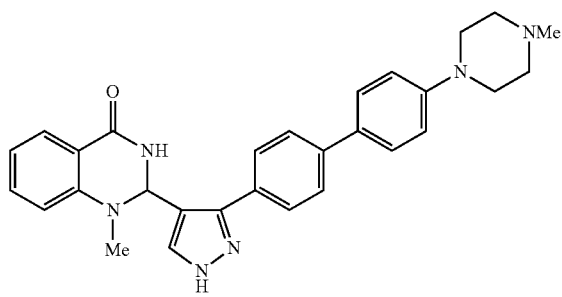

2-[3-(4-Iodophenyl)-1H-pyrazol]-4-yl]-1-methyl-2,3-dihydroquinazolin-4-one (50.0 mg), 4-(4-methylpiperazin-1-yl)phenylboronic acid, pinacol ester (45.7 mg) and a [1,1'-bis(diphenylphosphino)ferrocene]palladium (II) dichloride-dichloromethane adduct (4.8 mg) were suspended in a mixed solvent of ethanol (1.6 mL) and toluene (0.4 mL), a 2 M sodium carbonate aqueous solution (87 µL) was added, and the mixture was heated to 125° C. and reacted for 3 hours in a microwave reaction apparatus. The solvent was concentrated, and the residue was purified by silica gel chromatography (chloroform/methanol=99/1 to 92/8) to give the title compound (42.1 mg) as a brown solid.

$^1$H-NMR (270 MHz, DMSO-d$_6$) δ: 2.25 (s, 3H), 3.16-3.25 (m, 4H), 5.60-5.90 (m, 1H), 6.61-6.90 (m, 2H), 7.03 (brd, J=8.9 Hz, 2H), 7.15-7.33 (m, 1H), 7.36-7.46 (m, 1H), 7.55-7.80 (m, 7H), 8.54 (brs, 1H), 13.20 (brs, 1H).

MS (ESI) m/z: 479.66 [M+H]$^+$.

Example 7

1-Methyl-2-[4-[4-(4-morpholin-4-ylphenyl)phenyl]-2H-1,2,3-triazol-5-yl]-2,3-dihydroquinazolin-4-one

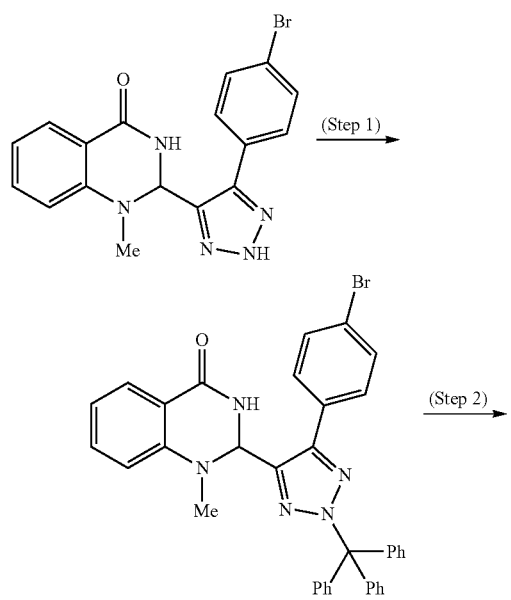

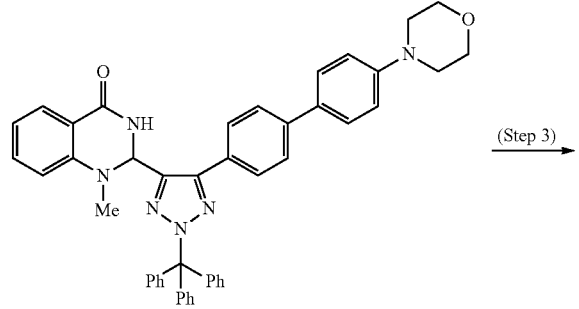

<Step 1>

2-[4-(4-Bromophenyl)-2H-1,2,3-triazol]-5-yl]-1-methyl-2,3-dihydroquinazolin-4-one (200 mg) was dissolved in tetrahydrofuran (4 mL), triethylamine (145 µL) was added, and the mixture was cooled with ice. To this solution was added trityl chloride (218 mg), and the mixture was then heated to room temperature, and stirred for 6 hours. Water (20 mL) was added, the mixture was extracted with ethyl acetate (20 mL), and the organic layers were washed with brine (20 mL). The aqueous layers were combined, and extracted with ethyl acetate (10 mL), and the organic layer was washed with brine (10 mL). Subsequently, the organic layers were combined, and dried over magnesium sulfate. The solvent was concentrated, and the residue was purified by silica gel column chromatography (hexane/ethyl acetate=70/30 to 50/50) to give 2-[4-(4-bromophenyl)-2-trityl-2H-1,2,3-triazol]-5-yl]-1-methyl-2,3-dihydroquinazolin-4-one (203 mg) as a white solid.

$^1$H-NMR (270 MHz, CDCl$_3$) δ: 2.63 (s, 3H), 6.02 (d, J=2.3 Hz, 1H), 6.36 (d, J=2.0 Hz, 1H), 6.66 (d, J=8.2 Hz, 1H), 6.92 (t, J=7.5 Hz, 1H), 7.03-7.12 (m, 5H), 7.22-7.33 (m, 10H), 7.33-7.40 (m, 1H), 7.41-7.48 (m, 2H), 7.56-7.65 (m, 2H), 7.88 (dd, J=7.6, 1.6 Hz, 1H).

MS (ESI) m/z: 626.29, 628.42 [M+H]$^+$.

<Step 2>

1-Methyl-2-[4-[4-(4-morpholin-4-ylphenyl)phenyl]-2-trityl-2H-1,2,3-triazol-5-yl]-2,3-dihydroquinazolin-4-one (61.9 mg) was prepared from 2-[4-(4-bromophenyl)-2-trityl-2H-1,2,3-triazol]-5-yl]-1-methyl-2,3-dihydroquinazolin-4-one (100 mg) in a manner similar to that of Example 6.

MS(ESI) m/z: 709.86 [M+H]$^+$

<Step 3>

1-Methyl-2-[4-[4-(4-morpholin-4-ylphenyl)phenyl]-2-trityl-2H-1,2,3-triazol-5-yl]-2,3-dihydroquinazolin-4-one (61.2 mg) was suspended in dichloromethane (1 mL), trifluoroacetic acid (0.5 mL) was added at room temperature, and the mixture was stirred overnight. The reaction mixture was diluted with ethyl acetate (20 mL), washed with saturated sodium bicarbonate water (20 mL) and brine (20 mL), and dried over magnesium sulfate. The solvent was concentrated, and the residue was purified by silica gel chromatography (chloroform/methanol=100/0 to 92/8) to give the title compound (17.1 mg) as a white solid.

$^1$H-NMR (270 MHz, DMSO-$d_6$) δ: 2.54-2.60 (m, 3H), 3.13-3.22 (m, 4H), 3.71-3.81 (m, 4H), 6.06 (d, J=3.0 Hz, 1H), 6.70 (d, J=8.6 Hz, 1H), 6.81 (t, J=7.4 Hz, 1H), 7.05 (d, J=8.9 Hz, 2H), 7.32-7.41 (m, 1H), 7.63 (d, J=8.9 Hz, 2H), 7.68-7.81 (m, 5H), 8.54 (d, J=3.0 Hz, 1H).

MS (ESI) m/z: 467.46 [M+H]$^+$.

Example 8

(2R)-2-[5-(4-Ethoxyphenyl)-2H-1,2,3-triazol-4-yl]-8-methyl-2,3-dihydro-1H-quinazolin-4-one

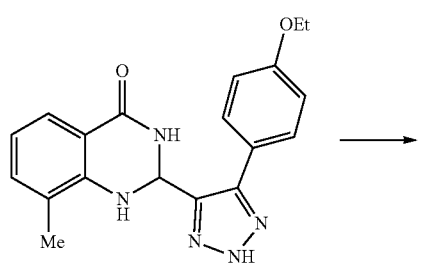

→

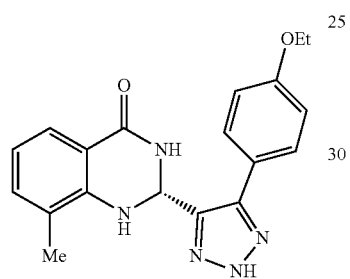

2-[5-(4-Ethoxyphenyl)-2H-1,2,3-triazol-4-yl]-8-methyl-2,3-dihydro-1H-quinazolin-4-one (136 mg) was optically resolved by high-performance liquid chromatography (methanol/TFA=100/0.05) with a chiral column (CHIRALPAC-IC; DAICEL) to give the title compound (59.4 mg; white solid) and an enantiomer thereof (2S)-2-[5-(4-ethoxyphenyl)-2H-1,2,3-triazol-4-yl]-8-methyl-2,3-dihydro-1H-quinazolin-4-one (60.1 mg; white solid)).

$^1$H-NMR (270 MHz, DMSO-$d_6$) δ: 1.33 (brt, J=6.9 Hz, 3H), 2.03 (brs, 3H), 3.96-4.16 (m, 2H), 6.07 (brs, 1H), 6.32 (brs, 1H), 6.68 (brs, 1H), 7.01 (brd, J=7.3 Hz, 2H), 7.15 (brd, J=6.9 Hz, 1H), 7.56 (brd, J=6.9 Hz, 1H), 7.62-7.86 (m, 2H), 8.20 (brs, 1H), 14.84 (brs, 1H).

MS (ESI) m/z: 350.26 [M+H]$^+$ $[α]_D^{24}$=−148° (C=0.1; MeOH)

The compounds of Examples 9 to 81 shown in Tables 3 to 18 below were prepared using the methods of Examples 1 to 8 and methods based thereon, and methods disclosed in literatures and methods based thereon.

TABLE 3

| Example | Compound Name | Structural formula | $^1$H NMR δ ppm | Solvent | ESI MS m/z |
|---|---|---|---|---|---|
| 9 | 2-(3-Phenyl-1H-pyrazol-4-yl)-2,3-dihydro-1H-quinazolin-4-one | | 5.49-6.02 (m, 1 H), 6.65-6.83 (m, 2 H), 6.92 (s, 1 H), 7.21-7.31 (m, 1 H), 7.34-7.84 (m, 6 H), 7.93-8.11 (m, 1 H), 8.16 (s, 1 H), 12.82-13.42 (m, 1 H) | DMSO-d6 | 291.22 [M + H]+ |
| 10 | 1-Methyl-2-(3-phenyl-1H-pyrazol-4-yl)-2,3-dihydroquinazolin-4-one | | 2.46 (s, 3 H), 5.55-5.88 (m, 1 H), 6.69 (d, J = 8.2 Hz, 1 H), 6.84 (t, J = 7.4 Hz, 1 H), 7.21 (br s, 1 H), 7.32-7.54 (m, 4 H), 7.56-7.71 (m, 2 H), 7.72-7.78 (m, 1 H), 8.52 (br s, 1 H), 12.78-13.41 (m, 1 H) | DMSO-d6 | 305.26 [M + H]+ |

TABLE 3-continued

| Example | Compound Name | Structural formula | ¹H NMR δ ppm | Solvent | ESI MS m/z |
|---|---|---|---|---|---|
| 11 | 1-Methyl-2-[3-(4-phenylmethoxyphenyl)-1H-pyrazol-4-yl]-2,3-dihydroquinazolin-4-one | | 2.46 (s, 3 H), 5.16 (s, 2 H), 5.66 (br s, 1 H), 6.70 (d, J = 8.2 Hz, 1 H), 6.85 (t, J = 7.6 Hz, 1 H), 7.12 (br d, J = 8.2 Hz, 2 H), 7.28-7.52 (m, 7 H), 7.58 (br d, J = 8.2 Hz, 2 H), 7.75 (dd, J = 7.6, 1.6 Hz, 1 H), 8.51 (br s, 1 H), 12.21-13.46 (m, 1H) | DMSO-d6 | 411.20 [M + H]+ |
| 12 | 1-Ethyl-2-[3-(4-methoxyphenyl)-1H-pyrazol-4-yl]-2,3-dihydroquinazolin-4-one | | 0.96 (t, J = 7.1 Hz, 3 H), 3.00-3.13 (m, 1 H), 3.27-3.41 (m, 1 H), 3.84 (s, 3 H), 5.86-5.89 (m, 1 H). 6.77 (d, J = 8.6 Hz, 1 H), 6.88 (t, J = 7.4 Hz, 1 H), 6.96 (d, J = 8.2 Hz, 2 H), 7.37-7.49 (m, 3 H), 7.54-7.66 (m, 1 H), 7.99 (dd, J = 7.6, 1.6 Hz, 1 H) | CDCl3 | 349.32 [M + H]+ |
| 13 | Methyl 4-[4-(1-ethyl-4-oxo-2,3-dihydroquinazolin-2-yl)-1H-pyrazol-3-yl]benzoate | | 0.93 (br t, J = 6.3 Hz, 3 H), 2.90-3.10 (m, 1 H), 3.13-3.39 (m, 1 H), 3.89 (s, 3 H), 5.90 (br s, 1 H), 6.73 (br d, J = 7.9 Hz, 1 H), 6.87 (br t, J = 7.3 Hz, 1 H), 7.33-7.64 (m, 5 H), 7.90-8.04 (m, 3 H) | CDCl3 | 377.34 [M + H]+ |

TABLE 4

| Example | Compound Name | Structural formula | ¹H NMR δ ppm | Solvent | ESI MS m/z |
|---|---|---|---|---|---|
| 14 | 1-(Cyclopropyl-methyl)-2-[5-(4-methoxyphenyl)-1H-pyrazol-4-yl]-2,3-dihydro-quinazolin-4-one | | −0.26--0.06 (m, 2 H), 0.11-0.29 (m, 2 H), 0.62-0.83 (m, 1 H), 3.67-4.06 (m, 5 H), 5.85 (br s, 1 H), 6.77-6.89 (m, 2 H), 6.99-7.09 (m, 2 H), 7.30-7.46 (m, 2 H), 7.51-7.61 (m, 2 H), 7.76 (br d, J = 7.3 Hz, 1 H), 8.58 (br s, 1 H) | DMSO-d6 | 375.28 [M + H]+ |

TABLE 4-continued

| Example | Compound Name | Structural formula | ¹H NMR δ ppm | Solvent | ESI MS m/z |
|---|---|---|---|---|---|
| 15 | 2-[5-(3-Methoxyphenyl)-1H-pyrazol-4-yl]-1-methyl-2,3-dihydroquinazolin-4-one | | 2.54 (s, 3 H), 3.68 (s, 3 H), 5.73 (d, J = 2.0 Hz, 1 H), 6.61 (d, J = 8.2 Hz, 1 H), 6.80-6.89 (m, 2 H), 6.96-7.08 (m, 2 H), 7.15-7.25 (m, 1 H), 7.29-7.42 (m, 2 H), 7.86-7.99 (m, 2 H) | CDCl3 | 335.26 [M + H]+ |
| 16 | 1-Methyl-2-[3-(4-nitrophenyl)-1H-pyrazol-4-yl]-2,3-dihydroquinazolin-4-one | | 2.55 (s, 3 H), 5.86 (d, J = 2.6 Hz, 1 H), 6.76 (d, J = 8.2 Hz, 1 H), 6.81-6.90 (m, 1 H), 7.38-7.46 (m, 1 H), 7.57 (br s, 1 H), 7.74 (dd, J = 7.6, 1.6 Hz, 1 H), 8.00 (d, J = 8.9 Hz, 2 H), 8.28 (d, J = 8.9 Hz, 2 H), 8.52 (d, J = 2.3 Hz, 1 H) | DMSO-d6 | 350.25 [M + H]+ |
| 17 | 1-Methyl-2-[3-(4-phenylphenyl)-1H-pyrazol-4-yl]-2,3-dihydroquinazolin-4-one | | 5.78 (br s, 1 H), 6.70-6.78 (m, 1 H), 6.79-6.93 (m, 1 H), 7.34-7.61 (m, 5 H), 7.67-7.88 (m, 7 H), 8.54 (br s, 1 H), 13.16 (br s, 1 H) | DMSO-d6 | 381.39 [M + H]+ |
| 18 | 1-Methyl-2-[3-(4-phenoxyphenyl)-1H-pyrazol-4-yl]-2,3-dihydroquinazolin-4-one | | 5.48-5.90 (m, 1 H), 6.71 (d, J = 8.2 Hz, 1 H), 6.84 (t, J = 7.4 Hz, 1 H), 6.94-7.30 (m, 6 H), 7.34-7.49 (m, 3 H), 7.64 (br s, 2 H), 7.74 (br d, J = 7.6 Hz, 1 H), 8.48 (br s, 1 H), 12.68-13.91 (m, 1 H) | DMSO-d6 | 397.89 [M + H]+ |

TABLE 5

| Example | Compound Name | Structural formula | ¹H NMR δ ppm | Solvent | ESI MS m/z |
|---|---|---|---|---|---|
| 19 | 2-[3-(4-Iodophenyl)-1H-pyrazol-4-yl]-1-methyl-2,3-dihydro-quinazolin-4-one | | 5.58-5.84 (m, 1 H), 6.67-6.77 (m, 1 H), 6.85 (t, J = 7.4 Hz, 1 H), 7.32-7.62 (m, 4 H), 7.75 (br t, J = 7.6 Hz, 2 H), 7.87 (br d, J = 8.6 Hz, 1 H), 8.40-8.58 (m, 1 H), 12.78-13.39 (m, 1 H) | DMSO-d6 | 431.31 [M + H]+ |
| 20 | 2-[3-(3-Bromophenyl)-1H-pyrazol-4-yl]-1-methyl-2,3-dihydro-quinazolin-4-one | | 5.59-5.83 (m, 1 H), 6.65-6.78 (m, 1 H), 6.85 (t, J = 7.4 Hz, 1 H), 7.31-7.97 (m, 7 H), 8.40-8.60 (m, 1 H), 12.97-13.36 (m, 1 H) | DMSO-d6 | 383.24, 385.22 [M + H]+ |
| 21 | 2-[3-(4-Fluorophenyl)-1H-pyrazol-4-yl]-1-methyl-2,3-dihydro-quinazolin-4-one | | 2.48 (br s, 3 H), 5.54-5.86 (m, 1 H), 6.71 (br d, J = 8.2 Hz, 1 H), 6.84 (td, J = 7.4, 1.0 Hz, 1 H), 7.15-7.81 (m, 7 H), 8.40-8.59 (m, 1 H), 12.71-13.37 (m, 1 H) | DMSO-d6 | 323.27 [M + H]+ |
| 22 | 1-Methyl-2-[3-(3-phenylphenyl)-1H-pyrazol-4-yl]-2,3-dihydroquinazolin-4-one | | 5.65-5.93 (m, 1 H), 6.74 (br s, 1 H), 6.86 (t, J = 7.4 Hz, 1 H), 7.21-7.51 (m, 5 H), 7.56-7.81 (m, 6 H), 7.87-8.16 (m, 1 H), 8.40-8.68 (m, 1 H), 12.85-13.46 (m, 1 H) | DMSO-d6 | 381.31 [M + H]+ |
| 23 | 1-Methyl-2-[5-[3-[4-(4-methylpiperazin-1-yl)phenyl]phenyl]-1H-pyrazol-4-yl]-2,3-dihydro-quinazolin-4-one | | 2.17-2.27 (m, 3 H), 2.48-2.53 (m, 7 H), 3.12-3.23 (m, 4 H), 5.62-5.94 (m, 1 H), 6.60-7.06 (m, 4 H), 7.20-8.04 (m, 9 H), 8.40-8.63 (m, 1 H), 12.85-13.36 (m, 1 H) | DMSO-d6 | 479.50 [M + H]+ |
| 24 | 2-[3-[4-(3-Hydroxyphenyl)phenyl]-1H-pyrazol-4-yl]-1-methyl-2,3-dihydro-quinazolin-4-one | | 5.76 (br s, 1 H), 6.68-6.92 (m, 3 H), 7.04-7.19 (m, 2 H), 7.22-7.34 (m, 1 H), 7.41 (br t, J = 7.1 Hz, 1 H), 7.49-7.91 (m, 6 H), 8.56 (br s, 1 H), 9.57 (br s, 1 H), 12.78-13.48 (m, 1 H) | DMSO-d6 | 397.38 [M + H]+ |

TABLE 6

| Example | Compound Name | Structural formula | ¹H NMR δ ppm | Solvent | ESI MS m/z |
|---|---|---|---|---|---|
| 25 | 1-Methyl-2-[5-[4-[4-[(4-methylpiperazin-1-yl)methyl]phenyl]phenyl]-1H-pyrazol-4-yl]-2,3-dihydroquinazolin-4-one | | 2.15 (s, 3 H), 2.23-2.47 (m, 8 H), 3.49 (s, 2 H), 5.62-5.90 (m, 1 H), 6.73 (br d, J = 8.2 Hz, 1 H), 6.85 (t, J = 7.6 Hz, 1 H), 7.17-7.48 (m, 4 H), 7.64-7.87 (m, 7 H), 8.55 (br s, 1 H), 12.82-13.40 (m, 1 H) | DMSO-d6 | 493.57 [M + H]+ |
| 26 | 1-Methyl-2-[5-[4-[3-[(4-methylpiperazin-1-yl)methyl]phenyl]phenyl]-1H-pyrazol-4-yl]-2,3-dihydroquinazolin-4-one | | 2.14 (s, 3 H), 2.20-2.49 (m, 8 H), 3.53 (s, 2 H), 5.78 (br s, 1 H), 6.73 (br d, J = 7.9 Hz, 1 H), 6.85 (br t, J = 7.4 Hz, 1 H), 7.17-7.53 (m, 4 H), 7.55-7.89 (m, 7 H), 8.56 (br s, 1 H), 12.73-13.46 (m, 1 H) | DMSO-d6 | 493.57 [M + H]+ |
| 27 | 1-Methyl-2-[3-(4-(2,2,2-trifluoromethoxy)phenyl]-1H-pyrazol-4-yl]-2,3-dihydroquinazolin-4-one | | 2.64 (s, 3 H), 4.31 (q, J = 7.7 Hz, 2 H), 5.75 (s, 1 H), 6.70 (br d, J = 8.1 Hz, 1 H), 6.84-6.98 (m, 3 H), 7.36 (br d, J = 8.6 Hz, 2 H), 7.40-7.55 (m, 3 H), 7.95 (dd, J = 7.7, 1.3 Hz, 1 H) | CDCl3 | 403.34 [M + H]+ |
| 28 | 2-[3-(3-Fluorophenyl)-1H-pyrazol-4-yl]-1-methyl-2,3-dihydroquinazolin-4-one | | 5.75 (br s, 1 H), 6.70 (br d, J = 8.1 Hz, 1 H), 6.83 (br t, J = 7.3 Hz, 1 H), 7.05-7.61 (m, 6 H), 7.72 (br d, J = 7.6 Hz, 1 H), 8.48 (br s, 1 H), 12.63-13.46 (m, 1 H) | DMSO-d6 | 323.28 [M + H]+ |
| 29 | 1-Methyl-2-[3-[4-(4-morpholin-4-yl)phenyl)phenyl]-1H-pyrazol-4-yl]-2,3-dihydroquinazolin-4-one | | 3.15-3.19 (m, 4 H), 3.51-3.77 (m, 4 H), 5.74 (br s, 1 H), 6.73 (d, J = 8.1 Hz, 1 H), 6.85 (t, J = 8.1 Hz, 1 H), 7.04 (d, J = 10.8 Hz, 2 H), 7.24 (br s, 1 H), 7.37-7.44 (m, 1 H), 7.61-7.78 (m, 7 H), 8.54 (br s, 1 H), 12.96-13.20 (m, 1 H) | DMSO-d6 | 466.40 [M + H]+ |

TABLE 7

| Example | Compound Name | Structural formula | ¹H NMR δ ppm | Solvent | ESI MS m/z |
|---|---|---|---|---|---|
| 30 | 1-Methyl-2-[3-[3-(4-morpholin-4-yl)phenyl)phenyl]-1H-pyrazol-4-yl]-2,3-dihydroquinazolin-4-one | | 3.15 (s, 4 H), 3.74-3.77 (m, 4 H), 5.78 (s, 1 H), 6.73 (d, J = 8.1 Hz, 1 H), 6.85 (t, J = 8.1 Hz, 1 H), 6.99 (d, J = 8.1 Hz, 2 H), 7.38-7.65 (m, 7 H), 7.75-7.78 (m, 1 H), 7.92 (br s, 1 H), 8.42 (s, 1 H) | DMSO-d6 | 466.37 [M + H]+ |
| 31 | 4-[4-(1-Methyl-4-oxo-2,3-dihydroquinazolin-2-yl)-1H-pyrazol-3-yl]benzonitrile | | 5.81 (d, J = 2.7 Hz, 1 H), 6.75 (d, J = 8.1 Hz, 1 H), 6.86 (t, J = 8.1 Hz, 1 H), 7.38-7.45 (m, 1 H), 7.54 (br s, 1 H), 7.74 (dd, J = 8.1, 2.7 Hz, 1 H), 7.90 (s, 4 H), 8.51 (d, J = 2.7 Hz, 1 H), 13.3 (br s, 1 H) | DMSO-d6 | 330.28 [M + H]+ |
| 32 | 1-Methyl-2-[5-[3-[4-[(4-methylpiperazin-1-yl)methylphenyl]phenyl]-1H-pyrazol-4-yl]-2,3-dihydroquinazolin-4-one | | 2.16 (s, 3 H), 2.36 (br s, 8 H), 3.47 (s, 2 H), 5.76 (br s, 1 H), 6.73 (d, J = 8.1 Hz, 1 H), 6.85 (t, J = 8.1 Hz, 1 H), 7.25-7.44 (m, 3 H), 7.50-7.78 (m, 7 H), 7.94-8.07 (m, 1 H), 8.54 (br s, 1 H), 13.04-13.28 (m, 1 H) | DMSO-d6 | 493.58 [M + H]+ |
| 33 | 1-Methyl-2-[5-[3-[3-[(4-methylpiperazin-1-yl)methylphenyl]phenyl]-1H-pyrazol-4-yl]-2,3-dihydroquinazolin-4-one | | 2.15 (s, 3 H), 2.35 (br s, 8 H), 3.51 (s, 2 H), 5.79 (br s, 1 H), 6.73-6.76 (m, 1 H), 6.86 (t, J = 8.1 Hz, 1 H), 7.25-7.78 (m, 10 H), 7.95-8.12 (m, 1 H), 8.53 (br s, 1 H), 13.06-13.31 (m, 1 H) | DMSO-d6 | 493.56 [M + H]+ |
| 34 | 2-[5-[4-[4-(Dimethylamino)phenyl]phenyl]-1H-pyrazol-4-yl]-1-methyl-2,3-dihydroquinazolin-4-one | | 2.95 (s, 6 H), 5.73 (br s, 1 H), 6.69-6.90 (m, 4 H), 7.41 (br t, J = 7.1 Hz, 2 H), 7.53-7.83 (m, 7 H), 8.55 (br s, 1 H), 12.72-13.37 (m, 1 H) | DMSO-d6 | 424.39 [M + H]+ |

TABLE 8

| Example | Compound Name | Structural formula | ¹H NMR δ ppm | Solvent | ESI MS m/z |
|---|---|---|---|---|---|
| 35 | 2-[5-[3-[4-(Dimethylamino)phenyl]phenyl]-1H-pyrazol-4-yl]-1-methyl-2,3-dihydroquinazolin-4-one | | 2.93 (s, 6 H), 5.76 (br s, 1 H), 6.66-6.91 (m, 4 H), 7.31-8.01 (m, 9 H), 8.54 (br s, 1 H), 12.69-13.56 (m, 1 H) | DMSO-d6 | 424.38 [M + H]+ |
| 36 | Ethyl 2-[4-[4-[4-(1-methyl-4-oxo-2,3-dihydroquinazolin-2-yl)-1H-pyrazol-5-yl]phenyl]phenyl]acetate | | 1.20 (t, J = 7.1 Hz, 3 H), 3.72 (s, 2 H), 4.10 (q, J = 6.9 Hz, 2 H), 5.65-5.89 (m, 1 H), 6.73 (br d, J = 7.9 Hz, 1 H), 6.85 (t, J = 7.4 Hz, 1 H), 7.32-7.47 (m, 3 H), 7.57 (br s, 1 H), 7.65-7.84 (m, 7 H), 8.55 (br d, J = 14.2 Hz, 1 H), 12.87-13.38 (m, 1 H) | DMSO-d6 | 467.41 [M + H]+ |
| 37 | Ethyl 2-[4-[3-[4-(1-methyl-4-oxo-2,3-dihydroquinazolin-2-yl)-1H-pyrazol-5-yl]phenyl]phenyl]acetate | | 1.20 (t, J = 7.3 Hz, 3 H), 3.70 (br d, J = 6.3 Hz, 2 H), 4.10 (q, J = 7.3 Hz, 2 H), 5.65-5.94 (m, 1 H), 6.73 (br s, 1 H), 6.86 (t, J = 7.3 Hz, 1 H), 7.25-7.80 (m, 10 H), 7.86-8.15 (m, 1 H), 8.38-8.66 (m, 1 H), 12.86-13.41 (m, 1 H) | DMSO-d6 | 467.40 [M + H]+ |
| 38 | 1-Methyl-2-[5-[4-[3-(4-methylpiperazin-1-yl)phenyl]phenyl]-1H-pyrazol-4-yl]-2,3-dihydroquinazolin-4-one | | 2.23 (s, 3 H), 3.15-3.27 (m, 4 H), 5.60-5.94 (m, 1 H), 6.73 (br d, J = 7.9 Hz, 1 H), 6.86 (t, J = 7.6 Hz, 1 H), 6.96 (br d, J = 6.9 Hz, 1 H), 7.06-7.47 (m, 5 H), 7.62-7.85 (m, 5 H), 8.55 (br d, J = 11.5 Hz, 1 H), 12.87-13.36 (m, 1 H) | DMSO-d6 | 479.47 [M + H]+ |

TABLE 9

| Example | Compound Name | Structural formula | ¹H NMR δ ppm | Solvent | ESI MS m/z |
|---|---|---|---|---|---|
| 39 | 1-Methyl-2-[3-[4-(1H-pyrrolo[2,3-b]pyridin-4-yl)phenyl]-1H-pyrazol-4-yl]-2,3-dihydroquinazolin-4-one | | 2.56 (s, 3 H), 5.63-5.99 (m, 1 H), 6.63-6.90 (m, 3 H), 7.08-8.02 (m, 10 H), 8.58 (br d, J = 11.2 Hz, 1 H), 11.84 (br s, 1 H), 12.89-13.41 (m, 1 H) | DMSO-d6 | 421.33 [M + H]+ |

TABLE 9-continued

| Example | Compound Name | Structural formula | ¹H NMR δ ppm | Solvent | ESI MS m/z |
|---|---|---|---|---|---|
| 40 | 1-Methyl-2-[3-(4-quinolin-4-ylphenyl)-1H-pyrazol-4-yl]-2,3-dihydroquinazolin-4-one | | 2.58 (s, 3 H), 5.72-5.96 (m, 1 H), 6.70-6.90 (m, 2 H), 7.35-8.00 (m, 11 H), 8.14 (br d, J = 8.2 Hz, 1 H), 8.60 (br d, J = 11.9 Hz, 1 H), 8.98 (br s, 1 H), 12.89-13.48 (m, 1 H) | DMSO-d6 | 432.33 [M + H]+ |
| 41 | 1-Methyl-2-[3-[4-(4-piperazin-1-yl)phenyl]phenyl]-1H-pyrazol-4-yl]-2,3-dihydroquinazolin-4-one | | 2.78-2.92 (m, 4 H), 3.03-3.17 (m, 4 H), 5.76 (br s, 1 H), 6.72 (br d, J = 7.9 Hz, 1 H), 6.85 (br t, J = 7.1 Hz, 1 H), 7.01 (br d, J = 7.9 Hz, 2 H), 7.23-7.87 (m, 9 H), 8.54 (br s, 1 H) | DMSO-d6 | 465.46 [M + H]+ |
| 42 | 2-[3-(3-Chlorophenyl)-1H-pyrazol-4-yl]-1-methyl-2,3-dihydroquinazolin-4-one | | 2.63 (s, 3 H), 5.75 (d, J = 2.3 Hz, 1 H), 6.68 (d, J = 8.2 Hz, 1 H), 6.91 (t, J = 7.5 Hz, 1 H), 7.33-7.54 (m, 6 H), 7.99 (dd, J = 7.6, 1.6 Hz, 1 H) | CDCl3 | 339.29 [M + H]+ |
| 43 | 2-[3-(4-Bromo-3-fluorophenyl)-1H-pyrazol-4-yl]-1-methyl-2,3-dihydroquinazolin-4-one | | 2.53 (s, 3 H), 5.80 (br s, 1 H), 6.75 (d, J = 8.2 Hz, 1 H), 6.85 (t, J = 7.4 Hz, 1 H), 7.33-7.62 (m, 3 H), 7.64-7.82 (m, 3 H), 8.50 (br s, 1 H), 13.18 (br s, 1 H) | DMSO-d6 | 401.18, 403.17 [M + H]+ |

TABLE 10

| Example | Compound Name | Structural formula | ¹H NMR δ ppm | Solvent | ESI MS m/z |
|---|---|---|---|---|---|
| 44 | 2-[5-[3-Fluoro-4-[4-(4-methylpiperazin-1-yl)phenyl]phenyl]-1H-pyrazol-4-yl]-1-methyl-2,3-dihydroquinazolin-4-one | | 2.23 (s, 3 H), 2.39-2.47 (m, 4 H), 2.54 (s, 3 H), 3.10-3.27 (m, 4 H), 5.66-5.91 (m, 1 H), 6.76 (br d, J = 3.6 Hz, 1 H), 6.86 (t, J = 7.4 Hz, 1 H), 7.04 (br d, J = 8.6 Hz, 2 H), 7.35-7.68 (m, 7 H), 7.75 (dd, J = 7.6, 1.6 Hz, 1 H), 8.52 (br s, 1 H), 12.78-13.47 (m, 1 H) | DMSO-d6 | 497.54 [M + H]+ |

TABLE 10-continued

| Example | Compound Name | Structural formula | ¹H NMR δ ppm | Solvent | ESI MS m/z |
|---|---|---|---|---|---|
| 45 | 2-[3-(3-Fluoro-4-phenylmethoxyphenyl)-1H-pyrazol-4-yl]-1-methyl-2,3-dihydroquinazolin-4-one | | 5.23 (s, 2 H), 5.71 (br s, 1 H), 6.72 (d, J = 8.2 Hz, 1 H), 6.85 (t, J = 6.9 Hz, 1 H), 7.30-7.59 (m, 10 H), 7.74 (dd, J = 7.6, 1.6 Hz, 1 H), 8.48 (br s, 1 H) | DMSO-d6 | 429.26 [M + H]+ |
| 46 | 2-[5-(4-Ethoxyphenyl)-1H-pyrazol-4-yl]-1-methyl-2,3-dihydroquinazolin-4-one | | 1.34 (t, J = 6.9 Hz, 3 H), 2.46 (s, 3 H), 4.07 (q, J = 6.9 Hz, 2 H), 5.61-5.70 (m, 1 H), 6.70 (d, J = 8.2 Hz, 1 H), 6.84 (t, J = 7.3 Hz, 1 H), 7.01 (d, J = 8.9 Hz, 2 H), 7.24-7.47 (m, 2 H), 7.54 (d, J = 8.6 Hz, 2 H), 7.75 (dd, J = 7.7, 1.5 Hz, 1 H), 8.47 (d, J = 2.6 Hz, 1 H), 12.98 (br s, 1 H) | DMSO-d6 | 349.46 [M + H]+ |
| 47 | 2-[3-(3,5-Difluorophenyl)-1H-pyrazol-4-yl]-1-methyl-2,3-dihydroquinazolin-4-one | | 2.53 (s, 3 H), 5.81 (br s, 1 H), 6.75 (d, J = 8.2 Hz, 1 H), 6.86 (t, J = 7.4 Hz, 1 H), 7.10-7.67 (m, 5 H), 7.74 (d, J = 6.3 Hz, 1 H), 8.48 (br s, 1 H), 12.62-13.75 (m, 1 H) | DMSO-d6 | 341.33 [M + H]+ |

TABLE 11

| Example | Compound Name | Structural formula | ¹H NMR δ ppm | Solvent | ESI MS m/z |
|---|---|---|---|---|---|
| 48 | 1-Methyl-2-[3-(4-(trifluoromethoxy)phenyl)-1H-pyrazol-4-yl]-2,3-dihydroquinazolin-4-one | | 5.75 (br s, 1 H), 6.73 (br d, J = 8.2 Hz, 1 H), 6.85 (t, J = 7.3 Hz, 1 H), 7.25-7.60 (m, 4 H), 7.65-7.88 (m, 3 H), 8.51 (br s, 1 H), 13.08 (br s, 1 H) | DMSO-d6 | 389.35 [M + H]+ |
| 49 | 2-[5-(3,5-Difluoro-4-methoxyphenyl)-1H-pyrazol-4-yl]-1-methyl-2,3-dihydroquinazolin-4-one | | 2.53 (s, 3 H), 3.96 (s, 3 H), 5.78 (br s, 1 H), 6.75 (d, J = 8.2 Hz, 1 H), 6.85 (t, J = 7.4 Hz, 1 H), 7.34-7.62 (m, 4 H), 7.73 (dd, J = 7.6, 1.6 Hz, 1 H), 8.48 (br s, 1 H), 13.12 (br s, 1 H) | DMSO-d6 | 371.30 [M + H]+ |

TABLE 11-continued

| Example | Compound Name | Structural formula | ¹H NMR δ ppm | Solvent | ESI MS m/z |
|---|---|---|---|---|---|
| 50 | 2-[5-(4-Methoxyphenyl)-1H-pyrazol-4-yl]-8-methyl-2,3-dihydro-1H-quinazolin-4-one | | 2.07 (s, 3 H), 3.78 (s, 3 H), 5.74 (br s, 1 H), 6.04 (br s, 1 H), 6.69 (t, J = 7.4 Hz, 1 H), 7.03 (br d, J = 6.3 Hz, 2 H), 7.16 (d, J = 6.6 Hz, 1 H), 7.56 (m, J = 7.6 Hz, 4 H), 8.15 (s, 1 H), 12.76-13.26 (m, 1 H) | DMSO-d6 | 335.27 [M + H]+ |
| 51 | 8-Methyl-2-[5-[4-[4-(4-methylpiperazin-1-yl)phenyl]phenyl]-1H-pyrazol-4-yl]-2,3-dihydro-1H-quinazolin-4-one | | 2.08 (s, 3 H), 2.22 (s, 3 H), 2.41-2.48 (m, 4 H), 3.14-3.24 (m, 4 H), 5.85 (br s, 1 H), 6.09 (br s, 1 H), 6.70 (t, J = 7.6 Hz, 1 H), 7.02 (br d, J = 8.9 Hz, 2 H), 7.17 (d, J = 6.6 Hz, 1 H), 7.53-7.80 (m, 8 H), 8.22 (s, 1 H), 12.96-13.28 (m, 1 H) | DMSO-d6 | 479.50 [M + H]+ |

TABLE 12

| Example | Compound Name | Structural formula | ¹H NMR δ ppm | Solvent | ESI MS m/z |
|---|---|---|---|---|---|
| 52 | 11-[5-(4-Methoxyphenyl)-1H-pyrazol-4-yl]-1,10-diazatricyclo[6.3.1.0$^{4,12}$]dodeca-4(12),5,7-trien-9-one | | 2.64-2.82 (m, 1 H), 2.83-3.01 (m, 2 H), 3.03-3.24 (m, 1 H), 3.77 (s, 3 H), 5.40 (br s, 1 H), 6.79 (br t, J = 7.4 Hz, 1 H), 7.01 (br s, 2 H), 7.25 (br d, J = 6.9 Hz, 1 H), 7.36 (br d, J = 7.6 Hz, 1 H), 7.45-7.85 (m, 3 H), 8.15 (s, 1 H), 12.86-13.27 (m, 1 H) | DMSO-d6 | 347.35 [M + H]+ |
| 53 | 2-[5-(4-Methoxyphenyl)-1H-pyrazol-4-yl]-1,7-dimethyl-2,3-dihydroquinazolin-4-one | | 2.28 (s, 3 H), 2.45 (s, 3 H), 3.80 (s, 3 H), 5.52-5.77 (m, 1 H), 6.52 (s, 1 H), 6.66 (d, J = 7.6 Hz, 1 H), 6.90-7.10 (m, 2 H), 7.12-7.31 (m, 1 H), 7.43-7.67 (m, 3 H), 8.40 (br s, 1 H), 12.64-13.17 (m, 1 H) | DMSO-d6 | 349.24 [M + H]+ |
| 54 | 8-Methyl-2-[3-(4-(2,2,2-trifluoroethoxy)phenyl)-1H-pyrazol-4-yl]-2,3-dihydro-1H-quinazolin-4-one | | 2.08 (s, 3 H), 4.79 (q, J = 8.9 Hz, 2 H), 5.75 (br s, 1 H), 6.06 (br s, 1 H), 6.69 (t, J = 7.6 Hz, 1 H), 7.03-7.25 (m, 3 H), 7.50-8.03 (m, 4 H), 8.17 (s, 1 H), 12.79-13.28 (m, 1 H) | DMSO-d6 | 403.25 [M + H]+ |

TABLE 12-continued

| Example | Compound Name | Structural formula | ¹H NMR δ ppm | Solvent | ESI MS m/z |
|---|---|---|---|---|---|
| 55 | 2-[5-(4-Ethoxyphenyl)-1H-pyrazol-4-yl]-8-methyl-2,3-dihydro-1H-quinazolin-4-one | | 1.33 (t, J = 6.9 Hz, 3 H), 2.07 (s, 3 H), 4.05 (q, J = 6.9 Hz, 2 H), 5.75 (s, 1 H), 6.02 (s, 1 H), 6.69 (t, J = 7.6 Hz, 1 H), 7.01 (br d, J = 8.6 Hz, 2 H), 7.16 (d, J = 6.6 Hz, 1 H), 7.51-7.62 (m, 3 H), 7.77 (br s, 1 H), 8.13 (s, 1 H), 12.99 (br s, 1 H) | DMSO-d6 | 349.40 [M + H]+ |

TABLE 13

| Example | Compound Name | Structural formula | ¹H NMR δ ppm | Solvent | ESI MS m/z |
|---|---|---|---|---|---|
| 56 | 2-[5-(3-Fluoro-4-methoxyphenyl)-1H-pyrazol-4-yl]-8-methyl-2,3-dihydro-1H-quinazolin-4-one | | 2.08 (s, 3 H), 3.86 (s, 3 H), 5.78 (s, 1 H), 6.06 (s, 1 H), 6.70 (t, J = 7.4 Hz, 1 H), 7.14-7.30 (m, 2 H), 7.45-7.60 (m, 3 H), 7.83 (br s, 1 H), 8.15 (s, 1 H), 13.07 (br s, 1 H) | DMSO-d6 | 353.40 [M + H]+ |
| 57 | 8-Ethyl-2-[3-(4-methoxyphenyl)-1H-pyrazol-4-yl]-2,3-dihydro-1H-quinazolin-4-one | | 1.05 (t, J = 7.4 Hz, 3 H), 2.38-2.47 (m, 2 H), 3.77 (s, 3 H), 5.67-5.80 (m, 1 H), 6.04-6.17 (m, 1 H), 6.73 (t, J = 7.6 Hz, 1 H), 6.94-7.10 (m, 2 H), 7.17 (dd, J = 7.4, 1.5 Hz, 1 H), 7.49-7.98 (m, 4 H), 8.17 (s, 1 H), 12.80-13.17 (m, 1 H) | DMSO-d6 | 349.36 [M + H]+ |
| 58 | 2-[5-(4-Methoxyphenyl)-2H-1,2,3-triazol-4-yl]-1-methyl-2,3-dihydro-quinazolin-4-one | | 3.80 (s, 3 H), 5.98 (d, J = 3.0 Hz, 1 H), 6.68 (d, J = 8.2 Hz, 1 H), 6.81 (t, J = 7.6 Hz, 1 H), 7.04 (d, J = 8.6 Hz, 2 H), 7.31-7.40 (m, 1 H), 7.61-7.75 (m, 3 H), 8.50 (d, J = 3.0 Hz, 1 H) | DMSO-d6 | 336.33 [M + H]+ |
| 59 | 2-[5-(4-Methoxyphenyl)-2H-1,2,3-triazol-4-yl]-2,3-dihydro-1H-quinazolin-4-one | | 3.78 (s, 3 H), 6.10 (s, 1 H), 6.67-6.81 (m, 2 H), 6.96-7.14 (m, 3 H), 7.27 (br t, J = 7.3 Hz, 1 H), 7.62-7.89 (m, 3 H), 8.24 (br s, 1 H) | DMSO-d6 | 322.24 [M + H]+ |

TABLE 13-continued

| Example | Compound Name | Structural formula | ¹H NMR δ ppm | Solvent | ESI MS m/z |
|---|---|---|---|---|---|
| 60 | 2-[4-(4-Bromophenyl)-2H-1,2,3-triazol-5-yl]-1-methyl-2,3-dihydroquinazolin-4-one | | 2.56 (s, 3 H), 6.04 (br s, 1 H), 6.69 (br d, J = 7.9 Hz, 1 H), 6.81 (br t, J = 7.1 Hz, 1 H), 7.28-7.56 (m, 2 H), 7.61-7.76 (m, 5 H), 8.53 (br s, 1 H) | DMSO-d6 | 384.19, 386.17 [M + H]+ |

TABLE 14

| Example | Compound Name | Structural formula | ¹H NMR δ ppm | Solvent | ESI MS m/z |
|---|---|---|---|---|---|
| 61 | 1-Methyl-2-[5-[3-[4-(4-methylpiperazin-1-yl)phenyl]phenyl]-2H-1,2,3-triazol-4-yl]-2,3-dihydroquinazolin-4-one | | 2.26 (s, 3 H), 2.56 (s, 3 H), 3.15-3.22 (m, 4 H), 6.08 (d, J = 2.6 Hz, 1 H), 6.71 (d, J = 7.9 Hz, 1 H), 6.82 (t, J = 7.3 Hz, 1 H), 6.95 (d, J = 8.9 Hz, 2 H), 7.35-7.75 (m, 7 H), 7.99 (s, 1 H), 8.54 (d, J = 2.6 Hz, 1 H) | DMSO-d6 | 480.49 [M + H]+ |
| 62 | 1-Methyl-2-[4-[3-(4-morpholin-4-ylphenyl)phenyl]-2H-1,2,3-triazol-5-yl]-2,3-dihydroquinazolin-4-one | | 2.55 (s, 3 H), 3.06-3.20 (m, 4 H), 3.66-3.86 (m, 4 H), 6.11 (br s, 1 H), 6.71 (br d, J = 7.9 Hz, 1 H), 6.83 (br t, J = 7.3 Hz, 1 H), 6.97 (br s, 2 H), 7.38 (br t, J = 6.9 Hz, 1 H), 7.47-7.79 (m, 6 H), 8.03 (br s, 1 H), 8.55 (br s, 1 H), 14.99 (br s, 1 H) | DMSO-d6 | 467.46 [M + H]+ |
| 63 | 2-[5-(4-Ethoxyphenyl)-2H-1,2,3-triazol-4-yl]-1-methyl-2,3-dihydroquinazolin-4-one | | 1.35 (t, J = 6.9 Hz, 3 H), 4.07 (q, J = 6.9 Hz, 2 H), 5.97 (d, J = 3.0 Hz, 1 H), 6.67 (d, J = 7.9 Hz, 1 H), 6.81 (t, J = 7.4 Hz, 1 H), 7.01 (d, J = 8.9 Hz, 2 H), 7.32-7.40 (m, 1 H), 7.63 (d, J = 8.9 Hz, 2 H), 7.71 (dd, J = 7.6, 1.6 Hz, 1 H), 8.48 (d, J = 3.3 Hz, 1 H) | DMSO-d6 | 350.34 [M + H]+ |
| 64 | 1-Methyl-2-[4-[4-(2,2,2-trifluoroethoxy)phenyl]-2H-1,2,3-triazol-5-yl]-2,3-dihydroquinazolin-4-one | | 2.53 (s, 3 H), 4.83 (q, J = 8.9 Hz, 2 H), 5.99 (d, J = 2.6 Hz, 1 H), 6.68 (d, J = 8.2 Hz, 1 H), 6.81 (t, J = 7.4 Hz, 1 H), 7.16 (d, J = 8.6 Hz, 2 H), 7.30-7.43 (m, 1 H), 7.63-7.78 (m, 3 H), 8.51 (d, J = 3.0 Hz, 1 H) | DMSO-d6 | 404.28 [M + H]+ |

TABLE 15

| Example | Compound Name | Structural formula | ¹H NMR δ ppm | Solvent | ESI MS m/z |
|---|---|---|---|---|---|
| 65 | 2-[5-(4-Methoxyphenyl)-2H-1,2,3-triazol-4-yl]-8-methyl-2,3-dihydro-1H-quinazolin-4-one | | 2.04 (s, 3 H), 3.79 (s, 3 H), 6.07 (s, 1 H), 6.35 (br s, 1 H), 6.69 (t, J = 7.4 Hz, 1 H), 7.03 (d, J = 8.9 Hz, 2 H), 7.15 (d, J = 7.3 Hz, 1 H), 7.56 (d, J = 6.9 Hz, 1 H), 7.74 (br d, J = 8.6 Hz, 2 H), 8.23 (br s, 1 H) | DMSO-d6 | 336.23 [M + H]+ |
| 66 | 2-[4-(4-Bromophenyl)-2H-1,2,3-triazol-5-yl]-8-methyl-2,3-dihydro-1H-quinazolin-4-one | | 2.03 (s, 3 H), 6.11 (s, 1 H), 6.39 (br s, 1 H), 6.69 (t, J = 7.4 Hz, 1 H), 7.15 (br d, J = 6.9 Hz, 1 H), 7.52-7.84 (m, 3 H), 8.26 (br s, 1 H) | DMSO-d6 | 384.27, 386.26 [M + H]+ |
| 67 | 8-Hydroxy-2-[5-(4-methoxyphenyl)-2H-1,2,3-triazol-4-yl]-2,3-dihydro-1H-quinazolin-4-one | | 3.79 (s, 3 H), 6.00 (br s, 1 H), 6.08 (s, 1 H), 6.59 (t, J = 7.9 Hz, 1 H), 6.81 (dd, J = 7.7, 1.2 Hz, 1 H), 7.03 (d, J = 8.6 Hz, 2 H), 7.18 (d, J = 7.6 Hz, 1 H), 7.75 (br d, J = 8.9 Hz, 2 H), 8.19 (br s, 1 H), 9.54 (br s, 1 H) | DMSO-d6 | 338.37 [M + H]+ |
| 68 | 2-[5-(4-Methoxyphenyl)-2H-1,2,3-triazol-4-yl]-10-oxa-1,3-diazatricyclo[7.3.1.0⁵,¹³]trideca-5,7,9(13)-trien-4-one | | 2.63-2.76 (m, 1 H), 2.88-2.99 (m, 1 H), 3.78 (s, 3 H), 3.97-4.12 (m, 1 H), 4.14-4.27 (m, 1 H), 5.93 (s, 1 H), 6.75 (t, J = 7.9 Hz, 1 H), 6.90 (br d, J = 7.6 Hz, 1 H), 7.03 (br d, J = 8.6 Hz, 2 H), 7.31 (br d, J = 7.8 Hz, 1 H), 7.77 (br d, J = 8.6 Hz, 2 H), 8.50 (br s, 1 H) | DMSO-d6 | 364.45 [M + H]+ |

TABLE 16

| Example | Compound Name | Structural formula | ¹H NMR δ ppm | Solvent | ESI MS m/z |
|---|---|---|---|---|---|
| 69 | 11-[5-(4-Methoxyphenyl)-2H-1,2,3-triazol-4-yl]-1,10-diazatricyclo[6.3.1.0⁴,¹²]dodeca-4(12),5,7-trien-9-one | | 2.82-3.12 (m, 4 H), 3.77 (s, 3 H), 5.82 (s, 1 H), 6.75-6.89 (m, 1 H), 6.93-7.11 (m, 2 H), 7.27 (br d, J = 7.3 Hz, 1 H), 7.37 (br d, J = 7.9 Hz, 1 H), 7.64-7.94 (m, 2 H), 8.16-8.27 (m, 1 H), 15.02 (br s, 1 H) | DMSO-d6 | 348.44 [M + H]+ |

TABLE 16-continued

| Example | Compound Name | Structural formula | ¹H NMR δ ppm | Solvent | ESI MS m/z |
|---|---|---|---|---|---|
| 70 | 2-[5-(4-Ethoxyphenyl)-2H-1,2,3-triazol-4-yl]-8-methyl-2,3-dihydro-1H-quinazolin-4-one | | 1.33 (t, J = 6.9 Hz, 3 H), 2.04 (s, 3 H), 4.06 (q, J = 6.9 Hz, 2 H), 6.06 (s, 1 H), 6.34 (br s, 1 H), 6.69 (t, J = 7.4 Hz, 1 H), 7.01 (d, J = 8.6 Hz, 2 H), 7.15 (d, J = 6.9 Hz, 1 H), 7.56 (d, J = 7.3 Hz, 1 H), 7.72 (d, J = 8.6 Hz, 2 H), 8.23 (br s, 1 H) | DMSO-d6 | 350.36 [M + H]+ |
| 71 | 2-[5-(4-Methoxyphenyl)-2H-1,2,3-triazol-4-yl]-8-(trifluoromethyl)-2,3-dihydro-1H-quinazolin-4-one | | 3.81 (s, 3 H), 6.08 (t, J = 3.3 Hz, 1 H), 6.85-6.97 (m, 2 H), 7.04 (d, J = 8.9 Hz, 2 H), 7.58-7.70 (m, 3 H), 7.97 (d, J = 7.3 Hz, 1 H), 8.62 (d, J = 2.6 Hz, 1 H) | DMSO-d6 | 390.33 [M + H]+ |
| 72 | 8-Methyl-2-[4-[4-(2,2,2-trifluoroethoxy)phenyl]-2H-1,2,3-triazol-5-yl]-2,3-dihydro-1H-quinazolin-4-one | | 2.04 (s, 3 H), 4.81 (q, J = 8.8 Hz, 2 H), 6.08 (s, 1 H), 6.37 (br s, 1 H), 6.69 (t, J = 7.4 Hz, 1 H), 7.10-7.22 (m, 3 H), 7.56 (br d, J = 7.3 Hz, 1 H), 7.79 (br d, J = 7.9 Hz, 2 H), 8.25 (br s, 1 H) | DMSO-d6 | 404.28 [M + H]+ |
| 73 | 2-[4-[4-(Difluoromethoxy)phenyl]-2H-1,2,3-triazol-5-yl]-8-methyl-2,3-dihydro-1H-quinazolin-4-one | | 2.03 (s, 3 H), 6.10 (s, 1 H), 6.41 (br s, 1 H), 6.69 (t, J = 7.4 Hz, 1 H), 6.99-7.35 (m, 4 H), 7.56 (br d, J = 9.6 Hz, 1 H), 7.87 (br d, J = 8.2 Hz, 2 H), 8.28 (br s, 1 H) | DMSO-d6 | 373.23 [M + H]+ |

TABLE 17

| Example | Compound Name | Structural formula | ¹H NMR δ ppm | Solvent | ESI MS m/z |
|---|---|---|---|---|---|
| 74 | 8-Methyl-2-[5-(4-propoxyphenyl)-2H-1,2,3-triazol-4-yl]-2,3-dihydro-1H-quinazolin-4-one | | 0.98 (t, J = 7.4 Hz, 3 H), 1.73 (sxt, J = 7.1 Hz, 2 H), 2.04 (s, 3 H), 3.96 (t, J = 6.6 Hz, 2 H), 6.06 (s, 1 H), 6.36 (br s, 1 H), 6.69 (t, J = 7.6 Hz, 1 H), 7.02 (d, J = 8.6 Hz, 2 H), 7.15 (d, J = 6.9 Hz, 1 H), 7.56 (d, J = 6.9 Hz, 1 H), 7.72 (br d, J = 8.6 Hz, 2 H), 8.25 (br s, 1 H) | DMSO-d6 | 364.26 [M + H]+ |
| 75 | 11-[5-(4-Ethoxyphenyl)-2H-1,2,3-triazol-4-yl]-1,10-diaza-tricyclo[6.3.1.0^{4,12}]dodeca-4(12),5,7-trien-9-one | | 1.32 (br t, J = 6.8 Hz, 3 H), 2.82-3.11 (m, 4 H), 3.97-4.13 (m, 2 H), 5.82 (br s, 1 H), 6.81 (br t, J = 7.6 Hz, 1 H), 6.91-7.10 (m, 2 H), 7.27 (br d, J = 7.3 Hz, 1 H), 7.37 (br d, J = 7.9 Hz, 1 H), 7.61-7.90 (m, 2 H), 8.26 (br s, 1 H), 15.03 (br s, 1 H) | DMSO-d6 | 362.24 [M + H]+ |
| 76 | 8-Methyl-2-[5-(4-propan-2-yloxyphenyl)-2H-1,2,3-triazol-4-yl]-2,3-dihydro-1H-quinazolin-4-one | | 1.27 (d, J = 5.9 Hz, 6 H), 2.03 (s, 3 H), 4.66 (spt, J = 6.0 Hz, 1 H), 6.06 (s, 1 H), 6.35 (br s, 1 H), 6.69 (t, J = 7.4 Hz, 1 H), 7.00 (d, J = 8.6 Hz, 2 H), 7.15 (d, J = 7.3 Hz, 1 H), 7.56 (d, J = 7.3 Hz, 1 H), 7.70 (br d, J = 8.6 Hz, 2 H), 8.24 (br s, 1 H) | DMSO-d6 | 364.30 [M + H]+ |
| 77 | 8-Methyl-2-[5-(4-trideuteriomethoxyphenyl)-2H-1,2,3-triazol-4-yl]-2,3-dihydro-1H-quinazolin-4-one | | 2.03 (s, 3 H), 6.07 (br s, 1 H), 6.34 (br s, 1 H), 6.69 (t, J = 7.9 Hz, 1 H), 7.02 (br d, J = 8.2 Hz, 2 H), 7.15 (br d, J = 7.3 Hz, 1 H), 7.56 (br d, J = 7.9 Hz, 1 H), 7.66-7.83 (m, 2 H), 8.22 (br s, 1 H), 14.86 (br s, 1 H) | DMSO-d6 | 339.28 [M + H]+ |

TABLE 18

| Example | Compound Name | Structural formula | ¹H NMR δ ppm | Solvent | ESI MS m/z |
|---|---|---|---|---|---|
| 78 | 2-[4-[4-(2,2-Difluoroethoxy)phenyl]-2H-1,2,3-triazol-5-yl]-8-methyl-2,3-dihydro-1H-quinazolin-4-one | | 2.03 (s, 3 H), 4.26-4.45 (m, 2 H), 6.08 (br s, 1 H), 6.16-6.79 (m, 3 H), 7.00-7.23 (m, 3 H), 7.56 (br d, J = 7.3 Hz, 1 H), 7.64-7.90 (m, 2 H), 8.22 (br s, 1 H), 14.90 (br s, 1 H) | DMSO-d6 | 386.27 [M + H]+ |
| 79 | Ethyl 2-[4-[4-(8-methyl-4-oxo-2,3-dihydro-1H-quinazolin-2-yl)-2H-1,2,3-triazol-5-yl]phenoxyacetate | | 1.21 (t, J = 7.3 Hz, 3 H), 2.02 (s, 3 H), 4.17 (q, J = 7.3 Hz, 2 H), 4.82 (s, 2 H), 6.07 (br s, 1 H), 6.33 (br s, 1 H), 6.61-6.75 (m, 1 H), 6.94-7.08 (m, 2 H), 7.15 (br d, J = 7.3 Hz, 1 H), 7.56 (br d, J = 7.6 Hz, 1 H), 7.68-7.87 (m, 2 H), 8.22 (br s, 1 H), 14.87 (br s, 1 H) | DMSO-d6 | 408.32 [M + H]+ |
| 80 | 2-[5-(4-Ethoxyphenyl)-2H-1,2,3-triazol-4-yl]-8-ethyl-2,3-dihydro-1H-quinazolin-4-one | | 1.01 (br t, J = 7.1 Hz, 3 H), 1.33 (t, J = 7.1 Hz, 3 H), 2.28-2.47 (m, 2 H), 4.06 (q, J = 6.9 Hz, 2 H), 6.05 (br s, 1 H), 6.38 (br s, 1 H), 6.72 (br t, J = 7.4 Hz, 1 H), 7.00 (br d, J = 7.9 Hz, 2 H), 7.15 (br d, J = 7.3 Hz, 1 H), 7.57 (br d, J = 7.3 Hz, 1 H), 7.63-7.83 (m, 2 H), 8.22 (br s, 1 H), 14.82 (br s, 1 H) | DMSO-d6 | 364.38 [M + H]+ |
| 81 | 8-Ethyl-2-[4-(4-methoxyphenyl)-2H-1,2,3-triazol-5-yl]-2,3-dihydro-1H-quinazolin-4-one | | 1.01 (br t, J = 7.4 Hz, 3 H), 2.30-2.17 (m, 2 H), 3.78 (s, 3 H), 6.05 (br s, 1 H), 6.39 (br s, 1 H), 6.72 (br t, J = 7.4 Hz, 1 H), 7.02 (br d, J = 8.2 Hz, 2 H), 7.15 (br d, J = 7.3 Hz, 1 H), 7.57 (d, J = 7.9 Hz, 1 H), 7.64-7.88 (m, 2 H), 8.22 (br s, 1 H), 14.84 (br s, 1 H) | DMSO-d6 | 350.35 [M + H]+ |

Example 82

2-[5-(4-Methoxyphenyl)-1H-pyrazol-4-yl]-2,3-dihydro-1H-quinazolin-4-one (CAS No. 1223730-46-8)

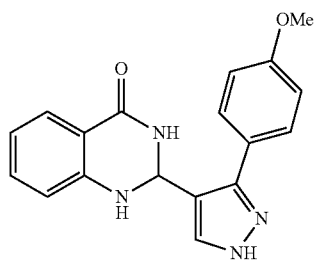 [SMILES: COc1ccc(-c2n[nH]cc2C2NC(=O)c3ccccc3N2)cc1]

The title compound was prepared using the method of Example 1.

Example 83

2-[5-(4-Methoxyphenyl)-1H-pyrazol-4-yl]-1-methyl-2,3-dihydroquinazolin-4-one (CAS No. 1252133-21-3)

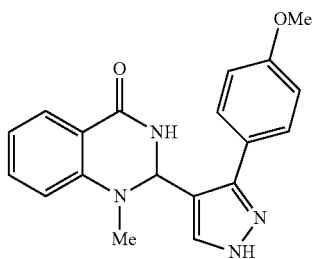 [SMILES: COc1ccc(-c2n[nH]cc2C2NC(=O)c3ccccc3N2C)cc1]

The title compound was prepared using the method of Example 1.

The compounds of Examples 84 to 87 shown in Table 19 below were prepared using the methods of Examples 1 to 8 and methods based thereon, and methods disclosed in literatures and methods based thereon.

TABLE 19

| Example | Compound Name | Structural formula | $^1$H NMR δ ppm | Solvent | ESI MS m/z |
|---|---|---|---|---|---|
| 84 | 11-[5-[4-(2,2-Difluoroethoxy)phenyl]-2H-1,2,3-triazol-4-yl]-1,10-diazatricyclo[6.3.1.0$^{4,12}$]dodeca-4(12),5,7-trien-9-one | | 2.84-3.07 (m, 4 H), 4.34 (td, J = 14.7, 3.6 Hz, 2 H), 5.81 (s, 1 H), 6.39 (tt, J = 54.4, 3.6 Hz, 1 H), 6.81 (t, J = 7.6 Hz, 1 H), 7.09 (d, J = 8.9 Hz, 2 H), 7.27 (d, J = 7.3 Hz, 1 H), 7.37 (d, J = 7.9 Hz, 1 H), 7.85 (d, J = 8.9 Hz, 2 H), 8.27 (br s, 1 H) | DMSO-d6 | 398.30 [M + H]+ |
| 85 | 2-[4-(4-Methoxyphenyl)-1H-pyrazol-3-yl]-2,3-dihydro-1H-quinazolin-4-one | | | | 321.27 [M + H]+ |
| 86 | 2-[4-(4-Methoxyphenyl)-1H-pyrazol-3-yl]-1-methyl-2,3-dihydro-1H-quinazolin-4-one | | | | 335.29 [M + H]+ |

TABLE 19-continued

| Example | Compound Name | Structural formula | $^1$H NMR δ ppm | Solvent | ESI MS m/z |
|---|---|---|---|---|---|
| 87 | 2-[4-(4-Methoxyphenyl)-1H-pyrazol-3-yl]-8-methyl-2,3-dihydro-1H-quinazolin-4-one | | | | 335.32 [M + H]+ |

(Test Example 1) Tankyrase Inhibitory Activity Test

The enzymatic activity of tankyrase 1 and the enzymatic activity of tankyrase 2 were measured by the ELISA method based on assessment of auto-poly(ADP-ribosyl)ation to evaluate the tankyrase inhibitory activity of the compound prepared in each of Examples (test compound) (inhibitory activity against tankyrase 1 (TNKS1) and inhibitory activity against tankyrase 2 (TNKS2)). First, Flag tagged tankyrase 1 (1,024-1,327aa, SAM+PARP) and tankyrase 2 (613-1, 116aa, ANK5+SAM+PARP) were synthesized with a cell-free protein expression system, and diluted with a Tris buffer solution (50 mM Tris-HCl (pH 8.0), 150 mM NaCl, 10% glycerol). 50 μL of the diluted tankyrase 1 or tankyrase 2 was added to a plate with an anti-FLAG M2 monoclonal antibody immobilized thereon (Anti-FLAG High-Sensitivity M2-Coated Plate) (Sigma-Aldrich), and the plate was left standing overnight at 4° C. Thereafter, the plate was washed four times with a PBS (PBST) buffer containing 0.1% Triton X-100. For Example 84, the Anti-FLAG High-Sensitivity M2-Coated Plate was replaced by an immunoplate (Thermo Fisher Scientific), tankyrase 1 or tankyrase 2 was immobilized on the immunoplate, and the immunoplate was then blocked with Blocking One (nacalai tesque), then washed with a PBS (PBST) buffer, and used as the following plate. With a control, this replacement was shown to have no impact on evaluation results.

Subsequently, the test compound diluted with an assay buffer (50 mM Tris-HCl (pH 8.0), 4 mM $MgCl_2$, 0.2 mM DTT) (DMSO was used as a control) was added to each well of the plate, and the plate was left standing at room temperature for 10 minutes. Thereafter, a biotin-labeled NAD solution (225 μM NAD, 25 μM 6-Biotin-17-NAD (Travigen, Inc.)) was added and mixed as a donor substrate, and the mixture was reacted at 30° C. for 45 minutes. To blank wells was added distilled water instead of the biotin-labeled NAD solution. After the reaction, the plate was washed with a PBST buffer four times. Thereafter, HRP (horseradish peroxidase)-labeled streptavidin (Travigen, Inc.) was diluted with a PBS buffer by 1,000 times, and added to each well, and the mixture was reacted at room temperature for 20 minutes. The plate was washed with a PBST buffer four times, a chemiluminescent substrate solution TACS-Sapphire (Travigen, Inc.) was then added to each well, the mixture was reacted at room temperature for 20 minutes, and the chemiluminescence intensity was measured using a chemiluminescence measuring apparatus. For Example 84, the streptavidin was diluted by 5,000 times, the chemiluminescent substrate solution TACS-Sapphire was replaced by an ELISA POD substrate TMB solution easy (nacalai tesque), the mixture was reacted at room temperature for 30 minutes, and the chemiluminescence intensity was measured using a chemiluminescence measuring apparatus. With a control, this replacement was shown to have no impact on evaluation results.

The residual enzymatic activity in the presence of the test compound was determined from the following expression. On the basis of the residual enzymatic activity at each of multiple concentrations of the test compound, the enzyme inhibitory activity was calculated in terms of a 50%-inhibition concentration ($IC_{50}$ value) using data analysis software Origin (LightStone Corp.).

Residual activity (%)={(chemiluminescence intensity with test compound added)−(chemiluminescence intensity of blank)}/{(chemiluminescence intensity of control)−(chemiluminescence intensity of blank)}

For the TNKS1 (inhibitory activity against tankyrase 1) and the TNKS2 (inhibitory activity against tankyrase 2) of each test compound as measured through the above-mentioned method, a test compound having an $IC_{50}$ value of less than 5 nM was rated "A", a test compound having an $IC_{50}$ value of 5 nM or more and less than 20 nM was rated "B", and a test compound having an $IC_{50}$ value of 20 nM or more and less than 50 nM was rated "C". Tables 20 to 23 below show the results.

(Test Example 2) Cell Proliferation Inhibitory Activity Test

The cell proliferation inhibitory activity of the compound, which had been prepared in each of Examples, against the human colorectal cancer cell line COLO-320DM was evaluated by Celltiter-Glo Luminescent Cell Viability Assay (Promega Corporation; G7573). COLO-320DM cells were cultured in RPMI-1640 medium containing 2 mM glutamine (Wako Pure Chemical Industries, Ltd; 189-02025) supplemented with 10% fetal bovine serum. The cultured cells were washed with PBS, and then dissociated with trypsin/EDTA, and a cell solution with $3 \times 10^4$ cells/mL was prepared.

Subsequently, the cell solution was seeded in a 96-well microplate (Thermo/Nunc Company; 136101) in an amount of 70 μL per well, and cultured overnight under the condition of 37° C. and 5% $CO_2$. Next day, a test compound solution obtained by diluting the test compound (DMSO solution) with a cell culture medium (final concentration of DMSO was 1%) was added in an amount of 10 μL per well, and the mixture was reacted under the condition of 37° C. and 5% $CO_2$ for 96 hours (a 1% DMSO solution was used as a control). Thereafter, a Celltiter-GloLuminescent Cell Viability Assay reagent (Promega Corporation; G7573) was added in an amount of 80 μL per well, the mixture was stirred with a shaker for 2 minutes while light was blocked with an aluminum foil, and the mixture was incubated at room temperature for 10 minutes.

Thereafter, a luminescence signal was measured with a luminometer (Biotech Company; Synergy). The ratio of cell proliferation in each compound addition group to cell proliferation in a control group containing no test compound solution, where cell proliferation in the control group is 100%, was calculated and the value of a compound concentration necessary for suppressing the amount of residual cells to 50% of that in the control (GI50) was calculated as the cytostatic activity. For the COLO-320DM (cell proliferation inhibitory activity against COLO-320DM) of each test compound as measured through the above-mentioned method, a test compound having a GI50 value of less than 1 μM was rated "A", a test compound having a GI50 value of 1 μM or more and less than 10 μM was rated "B", and a test compound having a GI50 value of 10 μM or more was rated "C". An unevaluated test compound was designated as "NT". Tables 20 to 23 show the results along with the results of the tankyrase inhibitory activity test.

TABLE 20

| Example | TNKS1 | TNKS2 | COLO-320DM |
|---|---|---|---|
| 1 | C | B | NT |
| 2 | A | A | NT |
| 3 | B | B | C |
| 4 | B | A | C |
| 5 | B | B | C |
| 6 | C | B | B |
| 7 | C | B | C |
| 8 | A | A | A |
| 9 | C | C | NT |
| 10 | B | A | C |
| 11 | B | A | C |
| 12 | C | B | B |
| 13 | C | C | C |
| 14 | C | C | C |
| 15 | B | C | C |
| 16 | C | C | C |
| 17 | C | A | C |
| 18 | C | A | C |
| 19 | B | A | C |
| 20 | C | B | C |
| 21 | C | B | C |
| 22 | A | A | C |
| 23 | C | C | B |
| 24 | B | B | C |
| 25 | B | C | C |

TABLE 21

| Example | TNKS1 | TNKS2 | COLO-320DM |
|---|---|---|---|
| 26 | C | B | C |
| 27 | A | B | C |
| 28 | A | B | B |
| 29 | B | B | B |
| 30 | B | B | B |
| 31 | B | B | C |
| 32 | C | C | C |
| 33 | C | C | C |
| 34 | C | C | B |
| 35 | C | C | C |
| 36 | C | C | C |
| 37 | C | C | C |
| 38 | C | C | B |
| 39 | C | C | C |
| 40 | C | C | C |
| 41 | C | B | B |
| 42 | C | B | B |
| 43 | A | A | C |
| 44 | B | B | B |
| 45 | A | A | B |
| 46 | A | A | B |
| 47 | C | B | C |
| 48 | C | B | B |
| 49 | C | B | C |
| 50 | B | B | C |

TABLE 22

| Example | TNKS1 | TNKS2 | COLO-320DM |
|---|---|---|---|
| 51 | C | C | B |
| 52 | A | B | C |
| 53 | B | B | C |
| 54 | B | A | B |
| 55 | B | A | B |
| 56 | B | B | C |
| 57 | B | A | B |
| 58 | B | A | B |
| 59 | C | A | B |
| 60 | B | B | B |
| 61 | B | B | C |
| 62 | B | B | C |
| 63 | B | B | B |
| 64 | C | B | C |
| 65 | B | A | A |
| 66 | B | A | C |
| 67 | B | B | C |
| 68 | B | B | B |
| 69 | B | B | B |
| 70 | B | A | A |
| 71 | C | C | B |
| 72 | B | B | B |
| 73 | C | C | C |
| 74 | B | B | B |
| 75 | B | B | B |

TABLE 23

| Example | TNKS1 | TNKS2 | COLO-320DM |
|---|---|---|---|
| 76 | C | B | B |
| 77 | B | B | A |
| 78 | B | A | B |
| 79 | B | B | C |
| 80 | B | B | A |
| 81 | B | A | B |
| 82 | B | B | C |
| 83 | B | B | B |
| 84 | B | B | C |
| 85 | B | A | B |
| 86 | A | A | B |
| 87 | A | A | B |

As shown in Tables 20 to 23, the compounds prepared in Examples 1 to 87 were all confirmed to have sufficient tankyrase inhibitory activity.

(Test Example 3) Microtubule Polymerization Inhibition Test

Using a microtubule polymerization reaction measurement kit (Cytoskeleton Inc.; BK011P), the microtubule polymerization inhibitory activity of the compound (test compound) prepared in each of Examples was evaluated on the basis of the standard protocol of the kit. Solutions with concentrations of 30 µM and 150 µM were prepared by dissolving the test compound in DMSO, and used as test compound solutions (with final concentrations of 3 µM and 15 µM, respectively). DMSO was used as a negative control solution, and vincristine (final concentration: 3 µM) was used as a positive control solution.

5 µL of the test compound solution or each control solution, and 50 µL of a microtubule-containing reaction mixture (1×Buffer 1; 1 mM GTP; 15% glycerol; and tubulin with a concentration of 2 mg/mL) were added to a 96-well plate (Corning Costar Company; #3686) warmed to 37° C., and a change in fluorescence of the reaction solution was measured over 1 hour. A higher fluorescence intensity means a higher degree of progression of polymerization of microtubules. The composition of Buffer 1 and the fluorescence measurement conditions employed in the analysis are shown below.

<1× Buffer 1 (pH 6.9)>

80 mM Piperazine-N,N'-bis[2-ethanesulfonic acid] sequisodium salt; 2.0 mM Magnesium chloride; 0.5 mM Ethylene glycol-bis (β-amino-ethyl ether)N,N,N',N'-tetra-acetic acid; 10 µM fluorescent reporter <Fluorescence Measurement Conditions>

Measurement wavelength: 360 nm (excitation wavelength) and 450 nm (emission wavelength)

Measurement time: 60 min (1 cycle/min)

Equipment used: Microplatereader SpectraMax M2 (Molecular Devices Company)

Figure 1B:
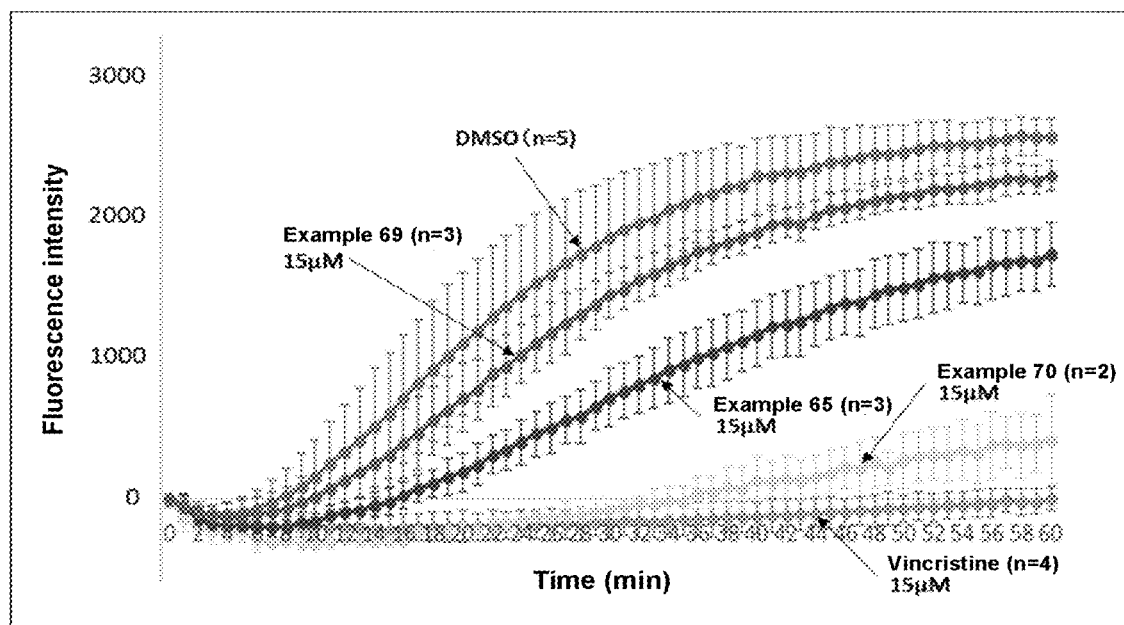
FIG. 1B shows the results of conducting a microtubule polymerization inhibition test of the compounds prepared in Examples 65, 69 and 70 (compound concentration: 15 µM).

FIGS. 1A and 1B shows the results of conducting a microtubule polymerization inhibition test of compounds (racemates) prepared in Examples 65, 69 and 70 (FIG. 1A shows the results of treatment at 3 µM and FIG. 1B shows the results of treatment at 15 µM). In FIGS. 1A and 1B, the abscissa represents a reaction time (minutes) and the ordinate represents a fluorescence intensity. FIGS. 1A and 1B indicate that after being mixed with the reaction mixture, the compounds (racemates) prepared in Examples 65, 69 and 70, as well as vincristine heretofore known as a microtubule polymerization inhibitor, showed a slower increase in fluorescence intensity as compared to the DMSO control. Thus, the compounds prepared in Examples 65, 69 and 70 were confirmed to have high microtubule polymerization inhibitory activity.

INDUSTRIAL APPLICABILITY

As described above, the present invention can provide a novel compound which has excellent tankyrase inhibitory activity and which is effective against diseases related to tankyrase and/or microtubules; a pharmacologically acceptable salt thereof; and a cell proliferation inhibitor, a tankyrase inhibitor, a microtubule inhibitor and a pharmaceutical composition which have excellent tankyrase inhibitory activity and/or microtubule inhibitory activity. The present invention can also provide a method for producing the novel compound and a pharmacologically acceptable salt thereof; and an intermediate compound useful for the production.

The invention claimed is:

1. A composition comprising a compound of the following formula (1) or a pharmaceutically acceptable salt thereof:

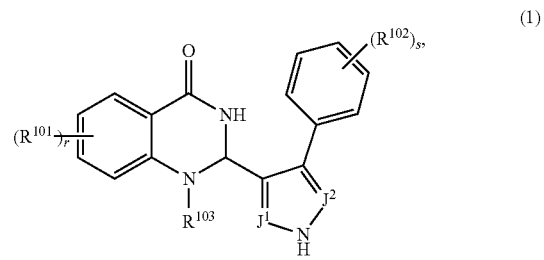

wherein $J^1$ is CH or N, and $J^2$ is N;

r represents 0 to 4;

each $R^{101}$ is the same or different when r is 2 or more, and represents a halogen atom, a $C_{1-6}$ alkyl group optionally substituted with a halogen atom, $OR^{111}$, or a group represented by the formula: $-N(R^{112a})-R^{112b}$, where $R^{111}$, $R^{112a}$ and $R^{112b}$ are each independently a hydrogen atom or a $C_{1-6}$ alkyl group;

s represents 0 to 5;

each $R^{102}$ is the same or different when s is 2 or more, and represents a halogen atom, a $C_{1-6}$ alkyl group, $OR^{113}$, a group represented by the formula: $-N(R^{114a})-R^{114b}$, a group represented by the formula: $-NH-C(=O)-R^{115}$, a group represented by the formula: $-C(=O)-R^{116}$, an optionally substituted aryl group, an optionally substituted heteroaryl group, a nitro group, or a cyano group, where $R^{113}$ is a hydrogen atom, an optionally substituted alkyl group, an optionally substituted aryl group, an optionally substituted arylalkyl group, or an optionally substituted heteroaryl group, $R^{114a}$ and $R^{114b}$ are each independently a hydrogen atom or a $C_{1-6}$ alkyl group, $R^{115}$ is an optionally substituted alkyl group, an optionally substituted aryl group, an optionally substituted heteroaryl group, or a group represented by the formula: $-NH-R^{121}$, $R^{116}$ is an optionally substituted alkyl group, an optionally substituted aryl group, an optionally substituted heteroaryl group, $OR^{122}$, or a group represented by the formula: $-N(R^{123a})-R^{123b}$, $R^{121}$ is an optionally substituted alkyl group, an optionally substituted aryl group, or an optionally substituted heteroaryl group, $R^{122}$ is a hydrogen atom, an optionally substituted alkyl group, an optionally substituted aryl group, or an optionally substituted heteroaryl group, and $R^{123a}$ and $R^{123b}$ are each independently a hydrogen atom, an optionally substituted alkyl group, an optionally substituted aryl group, or an optionally substituted heteroaryl group, or $R^{123a}$ and $R^{123b}$ are linked together to form a cyclic amine;

$R^{103}$ represents a hydrogen atom, a $C_{1-6}$ alkyl group, a $C_{3-6}$ cycloalkyl group, or a $C_{3-6}$ cycloalkyl $C_{1-6}$ alkyl group; and $R^{101}$ and $R^{103}$ are optionally linked together to form a five- to seven-membered hetero ring when $R^{101}$ is present at the 8-position; and a diluent or a pharmaceutically acceptable excipient.

2. The composition of claim 1, wherein the compound of the formula (1) is a compound of the following formula (1a):

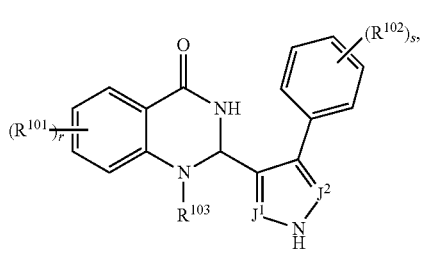

wherein $J^1$ is CH or N, and $J^2$ is N;
r represents 0 to 4;
each $R^{101}$ is the same or different when r is 2 or more, and represents a halogen atom, a $C_{1-6}$ alkyl group optionally substituted with a halogen atom, $OR^{111}$, or a group represented by the formula: —N($R^{112a}$)—$R^{112b}$,
where $R^{111}$, $R^{112a}$ and $R^{112b}$ are each independently a hydrogen atom or a $C_{1-6}$ alkyl group;
s represents 0 to 5;
each $R^{102}$ is the same or different when s is 2 or more, and represents a halogen atom, a $C_{1-6}$ alkyl group, $OR^{113}$, a group represented by the formula: —N($R^{114a}$)—$R^{114b}$, a group represented by the formula: —NH—C(=O)—$R^{115}$, a group represented by the formula: —C(=O)—$R^{116}$, an optionally substituted aryl group, an optionally substituted heteroaryl group, a nitro group, or a cyano group,
where $R^{113}$ is a hydrogen atom, an optionally substituted alkyl group, an optionally substituted aryl group, an optionally substituted arylalkyl group, or an optionally substituted heteroaryl group,
$R^{114a}$ and $R^{114b}$ are each independently a hydrogen atom or a $C_{1-6}$ alkyl group,
$R^{115}$ is an optionally substituted alkyl group, an optionally substituted aryl group, an optionally substituted heteroaryl group, or a group represented by the formula: —NH—$R^{121}$, $R^{116}$ is an optionally substituted alkyl group, an optionally substituted aryl group, an optionally substituted heteroaryl group, $OR^{122}$, or a group represented by the formula: —N($R^{123a}$)—$R^{123b}$,
$R^{121}$ is an optionally substituted alkyl group, an optionally substituted aryl group, or an optionally substituted heteroaryl group,
$R^{122}$ is a hydrogen atom, an optionally substituted alkyl group, an optionally substituted aryl group, or an optionally substituted heteroaryl group, and
$R^{123a}$ and $R^{123b}$ are each independently a hydrogen atom, an optionally substituted alkyl group, an optionally substituted aryl group, or an optionally substituted heteroaryl group, or $R^{123a}$ and $R^{123b}$ are linked together to form a cyclic amine;
$R^{103}$ represents a hydrogen atom, a $C_{1-6}$ alkyl group, a $C_{3-6}$ cycloalkyl group, or a $C_{3-6}$ cycloalkyl $C_{1-6}$ alkyl group; and
$R^{101}$ and $R^{103}$ are optionally linked together to form a five- to seven-membered hetero ring when $R^{101}$ is present at the 8-position,
with the exception of cases where $J^1$ represents CH, $J^2$ represents N, r is 0, $R^{103}$ is a hydrogen atom or a methyl group, $R^{102}$ is present at the p-position, and $R^{102}$ is a methoxy group.

3. The composition of claim 1, wherein in the formula (1), r is 0; or r is 1, $R^{101}$ is present at the 7-position or the 8-position and $R^{101}$ represents a $C_{1-3}$ alkyl group optionally substituted with a halogen atom, or a hydroxy group; or r is 1, $R^{101}$ is present at the 8-position and $R^{101}$ and $R^{103}$ are linked together to form a five- or six-membered hetero ring.

4. The composition of claim 1, wherein in the formula (1), $R^{103}$ represents a hydrogen atom, a $C_{1-3}$ alkyl group or a $C_{3-6}$ cycloalkyl $C_{1-3}$ alky group; or r is 1, $R^{101}$ is present at the 8-position and $R^{101}$ and $R^{103}$ are linked together to form a five- or six-membered hetero ring.

5. The composition of claim 1, wherein in the formula (1), s is 0; or s is 1 and $R^{102}$ represents a halogen atom, $OR^{113}$ in which $R^{113}$ is an optionally substituted $C_{1-3}$ alkyl group, or an optionally substituted aryl group.

6. The composition of claim 1, wherein in the formula (1), $J^1$ and $J^2$ each represent N.

7. A method for inhibiting cell proliferation, the method comprising contacting a cell with a compound of the following formula (1) or a pharmacologically acceptable salt thereof:

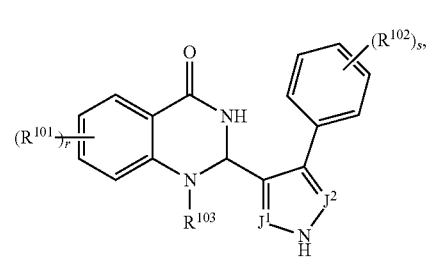

wherein $J^1$ is CH or N, and $J^2$ is N;
r represents 0 to 4;
each $R^{101}$ is the same or different when r is 2 or more, and represents a halogen atom, a $C_{1-6}$ alkyl group optionally substituted with a halogen atom, $OR^{111}$, or a group represented by the formula: —N($R^{112a}$)—$R^{112b}$,
where $R^{111}$, $R^{112a}$ and $R^{112b}$ are each independently a hydrogen atom or a $C_{1-6}$ alkyl group;
s represents 0 to 5;
each $R^{102}$ is the same or different when s is 2 or more, and represents a halogen atom, a $C_{1-6}$ alkyl group, $OR^{113}$, a group represented by the formula: —N($R^{114a}$)—$R^{114b}$, a group represented by the formula: —NH—C(=O)—$R^{115}$, a group represented by the formula: —C(=O)—$R^{116}$, an optionally substituted aryl group, an optionally substituted heteroaryl group, a nitro group, or a cyano group,
where $R^{113}$ is a hydrogen atom, an optionally substituted alkyl group, an optionally substituted aryl group, an optionally substituted arylalkyl group, or an optionally substituted heteroaryl group,
$R^{114a}$ and $R^{114b}$ are each independently a hydrogen atom or a $C_{1-6}$ alkyl group,
$R^{115}$ is an optionally substituted alkyl group, an optionally substituted aryl group, an optionally substituted heteroaryl group, or a group represented by the formula: —NH—$R^{121}$,
$R^{116}$ is an optionally substituted alkyl group, an optionally substituted aryl group, an optionally substituted heteroaryl group, $OR^{122}$, or a group represented by the formula: —N($R^{123a}$)—$R^{123b}$, $R^{121}$ is an optionally substituted alkyl group, an optionally substituted aryl group, or an optionally substituted heteroaryl group, $R^{122}$ is a hydrogen atom, an optionally substituted alkyl group, an optionally substituted aryl group, or an optionally substituted heteroaryl group, and $R^{123a}$ and $R^{123b}$ are each independently a hydrogen atom, an optionally substituted alkyl group, an optionally substituted aryl group, or an optionally substituted heteroaryl group, or $R^{123a}$ and $R^{123b}$ are linked together to form a cyclic amine;

$R^{103}$ represents a hydrogen atom, a $C_{1-6}$ alkyl group, a $C_{3-6}$ cycloalkyl group, or a $C_{3-6}$ cycloalkyl $C_{1-6}$ alkyl group; and $R^{101}$ and $R^{103}$ are optionally linked together to form a five- to seven-membered hetero ring when $R^{101}$ is present at the 8-position; and a diluent or a pharmaceutically acceptable excipient.

8. The method of claim 7, wherein the compound of the formula (1) is a compound of the following formula (1a):

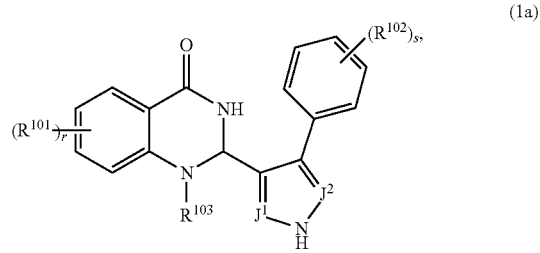

(1a)

wherein $J^1$ is CH or N, and $J^2$ is N;

r represents 0 to 4;

each $R^{101}$ is the same or different when r is 2 or more, and represents a halogen atom, a $C_{1-6}$ alkyl group optionally substituted with a halogen atom, $OR^{111}$, or a group represented by the formula: —N($R^{112a}$)—$R^{112b}$, where $R^{111}$, $R^{112a}$ and $R^{112b}$ are each independently a hydrogen atom or a $C_{1-6}$ alkyl group;

s represents 0 to 5;

each $R^{102}$ is the same or different when s is 2 or more, and represents a halogen atom, a $C_{1-6}$ alkyl group, $OR^{113}$, a group represented by the formula: —N($R^{114a}$)—$R^{114b}$, a group represented by the formula: —NH—C(=O)—$R^{115}$, a group represented by the formula: —C(=O)—$R^{116}$, an optionally substituted aryl group, an optionally substituted heteroaryl group, a nitro group, or a cyano group, where $R^{113}$ is a hydrogen atom, an optionally substituted alkyl group, an optionally substituted aryl group, an optionally substituted arylalkyl group, or an optionally substituted heteroaryl group, $R^{114a}$ and $R^{114b}$ are each independently a hydrogen atom or a $C_{1-6}$ alkyl group, $R^{115}$ is an optionally substituted alkyl group, an optionally substituted aryl group, an optionally substituted heteroaryl group, or a group represented by the formula: —NH—$R^{121}$, $R^{116}$ is an optionally substituted alkyl group, an optionally substituted aryl group, an optionally substituted heteroaryl group, $OR^{122}$, or a group represented by the formula: —N($R^{123a}$)—$R^{123b}$, $R^{121}$ is an optionally substituted alkyl group, an optionally substituted aryl group, or an optionally substituted heteroaryl group, $R^{122}$ is a hydrogen atom, an optionally substituted alkyl group, an optionally substituted aryl group, or an optionally substituted heteroaryl group, and $R^{123a}$ and $R^{123b}$ are each independently a hydrogen atom, an optionally substituted alkyl group, an optionally substituted aryl group, or an optionally substituted heteroaryl group, or $R^{123a}$ and $R^{123b}$ are linked together to form a cyclic amine;

$R^{103}$ represents a hydrogen atom, a $C_{1-6}$ alkyl group, a $C_{3-6}$ cycloalkyl group, or a $C_{3-6}$ cycloalkyl $C_{1-6}$ alkyl group; and $R^{101}$ and $R^{103}$ are optionally linked together to form a five- to seven-membered hetero ring when $R^{101}$ is present at the 8-position, with the exception of cases where $J^1$ represents CH, $J^2$ represents N, r is 0, $R^{103}$ is a hydrogen atom or a methyl group, $R^{102}$ is present at the p-position, and $R^{102}$ is a methoxy group.

9. The method of claim 7, wherein in the formula (1), r is 0; or r is 1, $R^{101}$ is present at the 7-position or the 8-position and $R^{101}$ represents a $C_{1-3}$ alkyl group optionally substituted with a halogen atom, or a hydroxy group; or r is 1, $R^{101}$ is present at the 8-position and $R^{101}$ and $R^{103}$ are linked together to form a five- or six-membered hetero ring.

10. The method of claim 7, wherein in the formula (1), $R^{103}$ represents a hydrogen atom, a $C_{1-3}$ alkyl group or a $C_{3-6}$ cycloalkyl $C_{1-3}$ alky group; or r is 1, $R^{101}$ is present at the 8-position and $R^{101}$ and $R^{103}$ are linked together to form a five- or six-membered hetero ring.

11. The method of claim 7, wherein in the formula (1), s is 0; or s is 1 and $R^{102}$ represents a halogen atom, $OR^{113}$ in which $R^{113}$ is an optionally substituted $C_{1-3}$ alkyl group, or an optionally substituted aryl group.

12. The method of claim 7, wherein in the formula (1), $J^1$ and $J^2$ each represent N.

13. The method of claim 7, comprising inhibiting tankyrase by administering the compound of the formula (1) or a pharmacologically acceptable salt thereof to a patient in need thereof.

14. The method of claim 8, comprising inhibiting tankyrase by administering the compound of the formula (1a) or a pharmacologically acceptable salt thereof to a patient in need thereof.

15. The method of claim 7, comprising inhibiting microtubules by administering the compound of the formula (1) or a pharmacologically acceptable salt thereof to a patient in need thereof.

16. The method of claim 8, comprising inhibiting microtubules by administering the compound of the formula (1a) or a pharmacologically acceptable salt thereof to a patient in need thereof.

17. The method of claim 7, comprising treating a disease attributable to tankyrase and/or microtubules by administering the compound of the formula (1) or a pharmacologically acceptable salt thereof to a patient in need thereof.

18. The method of claim 8, comprising treating a disease attributable to tankyrase and/or microtubules by administering the compound of the formula (1a) or a pharmacologically acceptable salt thereof to a patient in need thereof.

19. The method of claim 17, wherein the disease is selected from the group consisting of malignant tumor, Herpes simplex virus infection, Epstein-Barr virus infection, pulmonary fibrosis, multiple sclerosis and amyotrophic lateral sclerosis.

20. A compound of the following formula (1a) or a pharmacologically acceptable salt thereof:

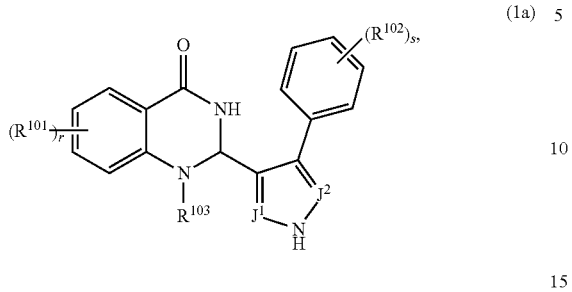

wherein $J^1$ is N, and $J^2$ is CH;

r represents 0 to 4;

each $R^{101}$ is the same or different when r is 2 or more, and represents a halogen atom, a $C_{1-6}$ alkyl group optionally substituted with a halogen atom, $OR^{111}$, or a group represented by the formula: $-N(R^{112a})-R^{112b}$, where $R^{111}$, $R^{112a}$ and $R^{112b}$ are each independently a hydrogen atom or a $C_{1-6}$ alkyl group;

s represents 0 to 5;

each $R^{102}$ is the same or different when s is 2 or more, and represents a halogen atom, a $C_{1-6}$ alkyl group, $OR^{113}$, a group represented by the formula: $-N(R^{114a})-R^{114b}$, a group represented by the formula: $-NH-C(=O)-R^{115}$, a group represented by the formula: $-C(=O)-R^{116}$ an optionally substituted aryl group, an optionally substituted heteroaryl group, a nitro group, or a cyano group, where $R^{113}$ is a hydrogen atom, an optionally substituted alkyl group, an optionally substituted aryl group, an optionally substituted arylalkyl group, or an optionally substituted heteroaryl group, $R^{114a}$ and $R^{114b}$ are each independently a hydrogen atom or a $C_{1-6}$ alkyl group, $R^{115}$ is an optionally substituted alkyl group, an optionally substituted aryl group, an optionally substituted heteroaryl group, or a group represented by the formula: $-NH-R^{121}$, $R^{116}$ is an optionally substituted alkyl group, an optionally substituted aryl group, an optionally substituted heteroaryl group, $OR^{122}$, or a group represented by the formula: $-N(R^{123a})-R^{123b}$, $R^{121}$ is an optionally substituted alkyl group, an optionally substituted aryl group, or an optionally substituted heteroaryl group, $R^{122}$ is a hydrogen atom, an optionally substituted alkyl group, an optionally substituted aryl group, or an optionally substituted heteroaryl group, and $Ru^{123a}$ and $R^{123b}$ are each independently a hydrogen atom, an optionally substituted alkyl group, an optionally substituted aryl group, or an optionally substituted heteroaryl group, or $R^{123a}$ and $R^{123b}$ are linked together to form a cyclic amine;

$R^{103}$ represents a hydrogen atom, a $C_{1-6}$ alkyl group, a $C_{3-6}$ cycloalkyl group, or a $C_{3-6}$ cycloalkyl $C_{1-6}$ alkyl group; and $R^{101}$ and $R^{103}$ are optionally linked together to form a five- to seven-membered hetero ring when $R^{101}$ is present at the 8-position.

21. A composition comprising a compound of the following formula (1) or a pharmacologically acceptable salt thereof:

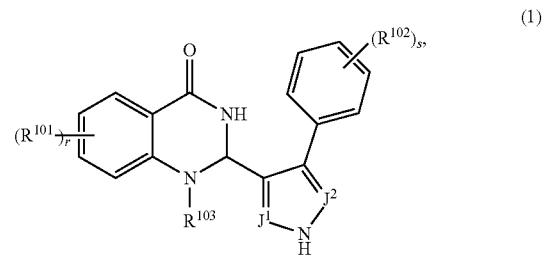

wherein $J^1$ is N, and $J^2$ is CH;

r represents 0 to 4;

each $R^{101}$ is the same or different when r is 2 or more, and represents a halogen atom, a $C_{1-6}$ alkyl group optionally substituted with a halogen atom, $OR^{111}$, or a group represented by the formula: $-N(R^{112a})-R^{112b}$), where $R^{111}$, $R^{112a}$ and $R^{112b}$ are each independently a hydrogen atom or a $C_{1-6}$ alkyl group;

s represents 0 to 5;

each $R^{102}$ is the same or different when s is 2 or more, and represents a halogen atom, a $C_{1-6}$ alkyl group, $OR^{113}$, a group represented by the formula: $-N(R^{114a})-R^{114b}$, a group represented by the formula: $-NH-C(=O)-R^{115}$, a group represented by the formula: $-C(=O)-R^{116}$, an optionally substituted aryl group, an optionally substituted heteroaryl group, a nitro group, or a cyano group, where $R^{113}$ is a hydrogen atom, an optionally substituted alkyl group, an optionally substituted aryl group, an optionally substituted arylalkyl group, or an optionally substituted heteroaryl group, $R^{114a}$ and $R^{114b}$ are each independently a hydrogen atom or a $C_{1-6}$ alkyl group, $R^{115}$ is an optionally substituted alkyl group, an optionally substituted aryl group, an optionally substituted heteroaryl group, or a group represented by the formula: $-NH-R^{121}$, $R^{116}$ is an optionally substituted alkyl group, an optionally substituted aryl group, an optionally substituted heteroaryl group, $OR^{122}$, or a group represented by the formula: $-N(R^{123a})-R^{123b}$, $R^{121}$ is an optionally substituted alkyl group, an optionally substituted aryl group, or an optionally substituted heteroaryl group, $R^{122}$ is a hydrogen atom, an optionally substituted alkyl group, an optionally substituted aryl group, or an optionally substituted heteroaryl group, and $R^{123a}$ and $R^{123b}$ are each independently a hydrogen atom, an optionally substituted alkyl group, an optionally substituted aryl group, or an optionally substituted heteroaryl group, or $R^{123a}$ and $R^{123b}$) are linked together to form a cyclic amine;

$R^{103}$ represents a hydrogen atom, a $C_{1-6}$ alkyl group, a $C_{3-6}$ cycloalkyl group, or a $C_{3-6}$ cycloalkyl $C_{1-6}$ alkyl group; and $R^{101}$ and $R^{103}$ are optionally linked together to form a five- to seven-membered hetero ring when $R^{101}$ is present at the 8-position; and a diluent or a pharmaceutically acceptable excipient.

22. A compound of the following formula (1a) or a pharmacologically acceptable salt thereof:

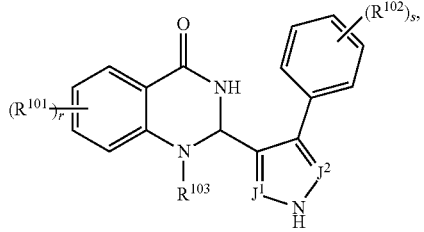

wherein $J^1$ is CH or N, and $J^2$ is N;
r represents 0 to 4;
each $R^{101}$ is the same or different when r is 2 or more, and represents a halogen atom, a $C_{1-6}$ alkyl group optionally substituted with a halogen atom, $OR^{111}$, or a group represented by the formula: $-N(R^{112a})-R^{112b}$,
where $R^{111}$, $R^{112a}$ and $R^{112b}$ are each independently a hydrogen atom or a $C_{1-6}$ alkyl group;
s represents 0 to 5;
each $R^{102}$ is the same or different when s is 2 or more, and represents a halogen atom, a $C_{1-6}$ alkyl group, $OR^{113}$, a group represented by the formula: $-N(R^{114a})-R^{114b}$, a group represented by the formula: $-NH-C(=O)-R^{115}$, a group represented by the formula: $-C(=O)-R^{116}$, an optionally substituted aryl group, an optionally substituted heteroaryl group, a nitro group, or a cyano group,
where $R^{113}$ is a hydrogen atom, an optionally substituted alkyl group, an optionally substituted aryl group, an optionally substituted arylalkyl group, or an optionally substituted heteroaryl group,
$R^{114a}$ and $R^{114b}$ are each independently a hydrogen atom or a $C_{1-6}$ alkyl group,
$R^{115}$ is an optionally substituted alkyl group, an optionally substituted aryl group, an optionally substituted heteroaryl group, or a group represented by the formula: $-NH-R^{121}$,
$R^{116}$ is an optionally substituted alkyl group, an optionally substituted aryl group, an optionally substituted heteroaryl group, $OR^{122}$, or a group represented by the formula: $-N(R^{123a})-R^{123b}$,
$R^{121}$ is an optionally substituted alkyl group, an optionally substituted aryl group, or an optionally substituted heteroaryl group,
$R^{122}$ is a hydrogen atom, an optionally substituted alkyl group, an optionally substituted aryl group, or an optionally substituted heteroaryl group, and
$R^{123a}$ and $R^{123b}$ are each independently a hydrogen atom, an optionally substituted alkyl group, an optionally substituted aryl group, or an optionally substituted heteroaryl group, or $R^{123a}$ and $R^{123b}$ are linked together to form a cyclic amine;
$R^{103}$ represents a hydrogen atom, a $C_{1-6}$ alkyl group, a $C_{3-6}$ cycloalkyl group, or a $C_{3-6}$ cycloalkyl $C_{1-6}$ alkyl group; and
$R^{101}$ and $R^{103}$ are optionally linked together to form a five- to seven-membered hetero ring when $R^{101}$ is present at the 8-position,
with the exception of the case wherein $J^1$ represents CH, $J^2$ represents N, r is 0, $R^{103}$ is a hydrogen atom or a methyl group, and $R^{102}$ is present at the p-position and is a methyl group, a methoxy group, a chlorine atom, or a fluorine atom, or $R^{102}$ is present at the m-position and is a methoxy group.

23. A method for inhibiting cell proliferation, the method comprising contacting a cell with a compound of the following formula (1) or a pharmacologically acceptable salt thereof:

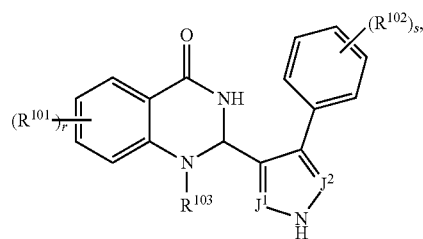

wherein $J^1$ is N, and $J^2$ is CH;
r represents 0 to 4;
each $R^{101}$ is the same or different when r is 2 or more, and represents a halogen atom, a $C_{1-6}$ alkyl group optionally substituted with a halogen atom, $OR^{111}$, or a group represented by the formula: $-N(R^{112a})-R^{112b}$,
where $R^{111}$, $R^{112a}$ and $R^{112b}$ are each independently a hydrogen atom or a $C_{1-6}$ alkyl group;
s represents 0 to 5;
each $R^{102}$ is the same or different when s is 2 or more, and represents a halogen atom, a $C_{1-6}$ alkyl group, $OR^{113}$, a group represented by the formula: $-N(R^{114a})-R^{114b}$, a group represented by the formula: $-NH-C(=O)-R^{115}$, a group represented by the formula: $-C(=O)-R^{116}$, an optionally substituted aryl group, an optionally substituted heteroaryl group, a nitro group, or a cyano group,
where $R^{113}$ is a hydrogen atom, an optionally substituted alkyl group, an optionally substituted aryl group, an optionally substituted arylalkyl group, or an optionally substituted heteroaryl group,
$R^{114a}$ and $R^{114b}$ are each independently a hydrogen atom or a $C_{1-6}$ alkyl group,
$R^{115}$ is an optionally substituted alkyl group, an optionally substituted aryl group, an optionally substituted heteroaryl group, or a group represented by the formula: $-NH-R^{121}$,
$R^{116}$ is an optionally substituted alkyl group, an optionally substituted aryl group, an optionally substituted heteroaryl group, $OR^{122}$, or a group represented by the formula: $-N(R^{123a})-R^{123b}$,
$R^{121}$ is an optionally substituted alkyl group, an optionally substituted aryl group, or an optionally substituted heteroaryl group,
$R^{122}$ is a hydrogen atom, an optionally substituted alkyl group, an optionally substituted aryl group, or an optionally substituted heteroaryl group, and $R^{123a}$ and $R^{123b}$ are each independently a hydrogen atom, an optionally substituted alkyl group, an optionally substituted aryl group, or an optionally substituted heteroaryl group, or $R^{123a}$ and $R^{123b}$ are linked together to form a cyclic amine;
$R^{103}$ represents a hydrogen atom, a $C_{1-6}$ alkyl group, a $C_{3-6}$ cycloalkyl group, or a $C_{3-6}$ cycloalkyl $C_{1-6}$ alkyl group; and $R^{101}$ and $R^{103}$ are optionally linked together to form a five- to seven-membered hetero ring when $R^{101}$ is present at the 8-position; and a diluent or a pharmaceutically acceptable excipient.

24. A compound of the following formula (1a) or a pharmacologically acceptable salt thereof:

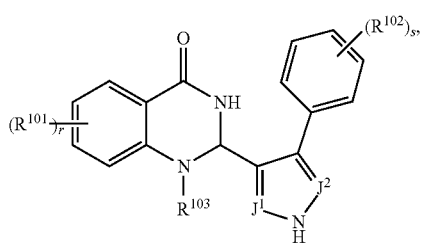

wherein $J^1$ is N, and $J^2$ is N;

r represents 0 to 4;

each $R^{101}$ is the same or different when r is 2 or more, and represents a halogen atom, a $C_{1-6}$ alkyl group optionally substituted with a halogen atom, $OR^{111}$, or a group represented by the formula: $-N(R^{112a})-R^{112b}$, where $R^{111}$, $R^{112a}$ and $R^{112b}$ are each independently a hydrogen atom or a $C_{1-6}$ alkyl group;

s represents 0 to 5;

each $R^{102}$ is the same or different when s is 2 or more, and represents a halogen atom, a $C_{1-6}$ alkyl group, $OR^{113}$, a group represented by the formula: $-N(R^{114a})-R^{114b}$, a group represented by the formula: $-NH-C(=O)-R^{115}$, a group represented by the formula: $-C(=O)-R^{116}$, an optionally substituted aryl group, an optionally substituted heteroaryl group, a nitro group, or a cyano group, where $R^{113}$ is a hydrogen atom, an optionally substituted alkyl group, an optionally substituted aryl group, an optionally substituted arylalkyl group, or an optionally substituted heteroaryl group, $R^{114a}$ and $R^{114b}$ are each independently a hydrogen atom or a $C_{1-6}$ alkyl group, $R^{115}$ is an optionally substituted alkyl group, an optionally substituted aryl group, an optionally substituted heteroaryl group, or a group represented by the formula: $-NH-R^{121}$, $R^{116}$ is an optionally substituted alkyl group, an optionally substituted aryl group, an optionally substituted heteroaryl group, $OR^{122}$, or a group represented by the formula: $-N(R^{123a})-R^{123b}$, $R^{121}$ is an optionally substituted alkyl group, an optionally substituted aryl group, or an optionally substituted heteroaryl group, $R^{122}$ is a hydrogen atom, an optionally substituted alkyl group, an optionally substituted aryl group, or an optionally substituted heteroaryl group, and $R^{123a}$ and $R^{123b}$ are each independently a hydrogen atom, an optionally substituted alkyl group, an optionally substituted aryl group, or an optionally substituted heteroaryl group, or $R^{123a}$ and $R^{123b}$ are linked together to form a cyclic amine;

$R^{103}$ represents a hydrogen atom, a $C_{1-6}$ alkyl group, a $C_{3-6}$ cycloalkyl group, or a $C_{3-6}$ cycloalkyl $C_{1-6}$ alkyl group; and $R^{101}$ and $R^{103}$ are optionally linked together to foiin a five- to seven-membered hetero ring when $R^{101}$ is present at the 8-position.

* * * * *

UNITED STATES PATENT AND TRADEMARK OFFICE
CERTIFICATE OF CORRECTION

PATENT NO. : 11,566,017 B2
APPLICATION NO. : 16/958066
DATED : January 31, 2023
INVENTOR(S) : Yoshida et al.

It is certified that error appears in the above-identified patent and that said Letters Patent is hereby corrected as shown below:

In the Claims

Column 78, Claim 1, Line 5, Formula (1), the portion of the formula reading --$(R^{102})_s,$-- should read --$(R^{102})_s$--.

Column 79, Claim 2, Line 5, Formula (1a), the portion of the formula reading --$(R^{102})_s,$-- should read --$(R^{102})_s$--.

Column 80, Claim 7, Line 25, Formula (1), the portion of the formula reading --$(R^{102})_s,$-- should read --$(R^{102})_s$--.

Column 81, Claim 8, Line 25, Formula (1a), the portion of the formula reading --$(R^{102})_s,$-- should read --$(R^{102})_s$--.

Column 83, Claim 20, Line 5, Formula (1a), the portion of the formula reading --$(R^{102})_s,$-- should read --$(R^{102})_s$--.

Column 84, Claim 21, Line 5, Formula (1), the portion of the formula reading --$(R^{102})_s,$-- should read --$(R^{102})_s$--.

Column 85, Claim 22, Line 5, Formula (1a), the portion of the formula reading --$(R^{102})_s,$-- should read --$(R^{102})_s$--.

Column 86, Claim 22, Line 2, delete "in-position" and insert --m-position--.

Column 86, Claim 23, Line 10, Formula (1), the portion of the formula reading --$(R^{102})_s,$-- should read --$(R^{102})_s$--.

Signed and Sealed this
Nineteenth Day of September, 2023

Katherine Kelly Vidal
*Director of the United States Patent and Trademark Office*

Column 87, Claim 24, Line 10, Formula (1a), the portion of the formula reading --$(R^{102})_s$,-- should read --$(R^{102})_s$--.

Column 88, Claim 24, Line 30, delete "foiin" and insert --form--.